US011149294B2

United States Patent
Cuero Rengifo et al.

(10) Patent No.: US 11,149,294 B2
(45) Date of Patent: *Oct. 19, 2021

(54) DNA CONSTRUCTS AND BIOLOGICAL DEVICES FOR PRODUCING CARBO SUGARS

(71) Applicant: Bio Capital Holdings, LLC, Houston, TX (US)

(72) Inventors: Raul Cuero Rengifo, Cypress, TX (US); Juliana Londoño Murillo, Manizales (CO); Mariana Sanchez Londoño, Manizales (CO); Daniel Agudelo Valencia, Manizales (CO); Juan Miguel Sanchez Bustamante, Manizales (CO); Mario Antonio Franco Jimenez, Manizales (CO); Lina Clemencia Sanchez Bustamante, Bogota (CO)

(73) Assignee: BIOCAPITAL HOLDINGS, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,483

(22) Filed: Apr. 30, 2019

(65) Prior Publication Data

US 2019/0338326 A1 Nov. 7, 2019

Related U.S. Application Data

(60) Provisional application No. 62/664,991, filed on May 1, 2018.

(51) Int. Cl.

| *C12P 19/04* | (2006.01) |
| *C12N 9/10* | (2006.01) |
| *C12N 15/81* | (2006.01) |
| *C12N 15/72* | (2006.01) |
| *C12N 1/20* | (2006.01) |
| *C12N 1/16* | (2006.01) |
| *C09K 8/80* | (2006.01) |
| *C08G 18/08* | (2006.01) |
| *C02F 1/68* | (2006.01) |

(52) U.S. Cl.
CPC ............... *C12P 19/04* (2013.01); *C12N 1/16* (2013.01); *C12N 1/20* (2013.01); *C12N 9/1059* (2013.01); *C12N 15/72* (2013.01); *C12N 15/815* (2013.01); *C02F 1/681* (2013.01); *C08G 18/08* (2013.01); *C09K 8/80* (2013.01)

(58) Field of Classification Search
None
See application file for complete search history.

(56) References Cited

U.S. PATENT DOCUMENTS

| 5,550,262 | A | 8/1996 | Iqbal et al. |
| 2006/0206964 | A1 | 9/2006 | Chiang et al. |
| 2007/0092957 | A1 | 4/2007 | Donaldson et al. |
| 2007/0283461 | A1 | 12/2007 | Dhugga et al. |
| 2010/0154075 | A1* | 6/2010 | McCarthy .......... C12N 15/8246 800/278 |
| 2011/0092393 | A1 | 4/2011 | Faust, Jr. et al. |
| 2012/0184004 | A1* | 7/2012 | Kay ........................ C12N 9/88 435/134 |
| 2013/0030067 | A1 | 1/2013 | Mooney et al. |
| 2014/0033360 | A1* | 1/2014 | Rengifo ............. C12N 15/8243 800/278 |
| 2016/0017362 | A1 | 1/2016 | Cuero Rengifo et al. |

FOREIGN PATENT DOCUMENTS

| CN | 1611600 | 5/2005 |
| WO | 2012101220 | 8/2012 |
| WO | 2016010525 | 1/2016 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession A9QXC7. Feb. 5, 2008 (Year: 2008).*
Accession Q564G7. Feb. 26, 2008 (Year: 2008).*
Accession AY268069. Oct. 4, 2003 (Year: 2003).*
Sun et al. Preparation and activity validation of PP7 bacteriophage-like particles displaying PAP114-128 peptide. Xi Bao Yu Fen Zi Mian Yi Xue Za Zhi. Oct. 2016;32(10):1356-1361. Abstract. (Year: 2016).*
Invitrogen pYES2 User Manual. Dec. 5, 2008 (Year: 2008).*
Lee et al. Biomed Res Int. vol. 2015, Article ID 820575, 9 pages. Epub Jun. 9, 2015 (Year: 2015).*
Sambrook et al. Molecular cloning A Laboratory Manual, 2nd edition, Cold Spring Harbor, N.Y. 1989, pp. 8.46-8.52 and pp. 11.2-11.19 (Year: 1989).*
International Search Report and Written Opinion for PCT/US2017/058940 dated Feb. 5, 2018, 16pp.

* cited by examiner

*Primary Examiner* — Christian L Fronda
(74) *Attorney, Agent, or Firm* — Thomas|Horstemeyer, LLP

(57) ABSTRACT

Described herein are biological devices and methods for using the same to produce carbo sugars. The biological devices include microbial cells transformed with a DNA construct containing genes for producing a cellulose synthase and galactomannan galactosyltransferase. In some instances, the biological devices also include a gene for lipase. Methods for altering the viscosity of petroleum oil using the carbo sugars are also described herein. Finally, methods for degreasing or decontaminating water mixed with petroleum oil or other fatty substances or a surface coated with petroleum oil or other fatty substances using the carbo sugars are described herein.

17 Claims, 31 Drawing Sheets

Specification includes a Sequence Listing.

1.

T7 Promoter ➡ Cellulose Synthase ➡ Galactomannan's ➡ Yellow Reporter + STOP ➡ T7 Terminator Sub-cloned Device in pYES2 vector

2.

Gal1 Promoter from pYES2 ➡ Cellulose Synthase ➡ Galactomannan's ➡ Yellow Reporter + STOP ➡ CYC1 Terminator from pYES2

Sub-cloned Device in pYES2 vector

3.

GAL1 Promoter from pYES2 ➡ Cellulose Synthase ➡ CYC1 terminator + Gal1 Prom ➡ Galactomannan's ➡ CYC1 terminator + Gal1 Prom ➡ Yellow Reporter Sub-cloned Device in pYES2 vector

FIGURE 2

*The original API of the petroleum oil were 20 API, but its final API were 12 after measuring them

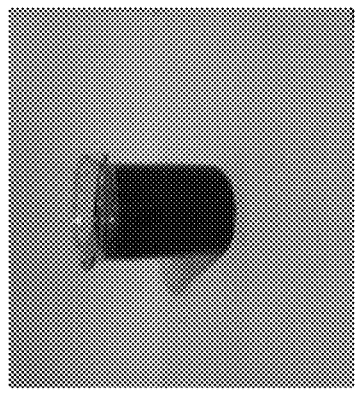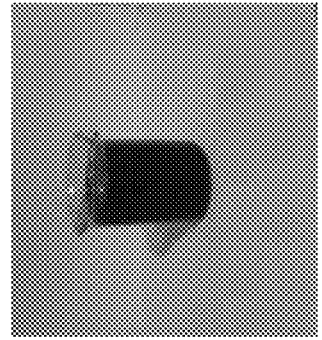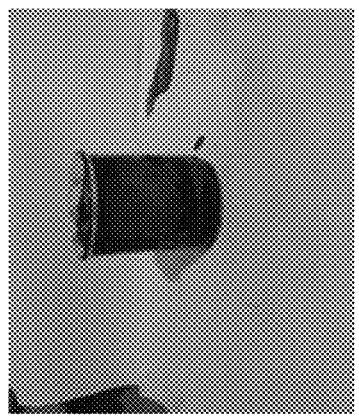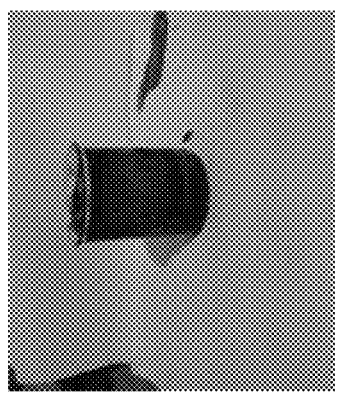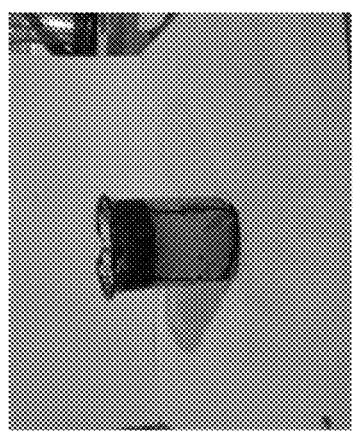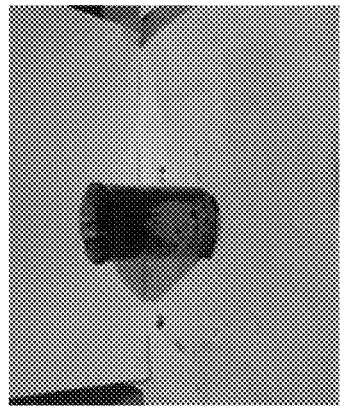
FIGURE 15A
FIGURE 15B

SEQUENCE LISTING

<160> NUMBER OF SEQ ID NOS: 11

<210> SEQ ID NO 1
<211> LENGTH: 2328
<212> TYPE: DNA
<213> ORGANISM: Pyropia yezoensis

<400> SEQUENCE: 1

| | | | | | | |
|---|---|---|---|---|---|---|
| ggatccggta | ccatggagac | tgttcgtcca | ggttgttttc | gtgctgttgt | ttctgttcca | 60 |
| ctgggtcgtc | tgacttactc | tttcctggtg | gacggtcagc | cgaagtacaa | cccggactgt | 120 |
| ccgactctgg | ttaacgaagc | tggcgtgcgt | gtgaacgtac | gccacggtgg | ttctgacggt | 180 |
| gattgcgacg | tgaagctga | cgaagaatgg | ggtaaaggtc | gtccaagccg | tgctcgtcgc | 240 |
| gtgctgagcc | aggtttctgg | cctggacctg | tactctcagc | actccaccag | cgacatcgtt | 300 |
| tctatgctgg | tgttccgttt | cttctacctg | gctatgattc | cagctggtgc | ctactacttc | 360 |
| ttctggctga | gcgttcgtgg | tggtaatcgc | caggctccag | tttgctgggt | ggtgttcgtt | 420 |
| atgagcgaaa | tcctgtcttt | cgttagcgcg | ctgatttccc | tgtttggcat | gtggaagccg | 480 |
| atcaaacgtc | gttggcgctc | tctggacgct | ctgcgtccag | ctctgccagt | tgcagattgg | 540 |
| ccaactgtag | acgtgatcat | ttgccactac | aaagaggaca | ccgaacagct | gcgtcagact | 600 |
| attcgtgcag | cgatgaaact | ggattaccca | gcccatctgc | tgcacattct | gattgccgac | 660 |
| gatggcttct | tcccaaccct | caagatggta | gagcgttctg | atattggtct | ggctctgtac | 720 |
| cagacctgtg | ttgaggaagc | gggttatgat | ccgctgctgg | aagaaaccat | gaatgaacgt | 780 |
| ggtctggttg | aacactatac | tgttaaggca | ggtgacgacc | tgccgcgtca | tgattgcgcg | 840 |
| gttgaagctc | accagttcga | gtttggtccg | tatggtgcgg | acatgtacgg | tccaggtgcc | 900 |
| ctgccacgtc | tgtccctggt | tgctcgtgtg | aagccggctg | acgctcacaa | caaggcaggc | 960 |
| aacatcaaca | acgtactgtc | caactctaac | gcagaaggta | agattgttct | gttcctggat | 1020 |
| gctgacatga | agccggtaga | atcttacctg | ctgcgtgttc | tgccactgat | gctggaagag | 1080 |
| cagcgttccg | atagcctgca | gagccaactg | atccaggcag | aggacccaga | gctgggtgct | 1140 |
| ggtacttcta | agagctggca | aatcaaccgt | gacattggct | tcgttggctg | cccacaacgc | 1200 |
| ttcgcgaacg | tatccggtga | ccatccggat | tactgtgctc | accgtaacgc | gatctactac | 1260 |
| gacggtatct | gcactggtcg | tgatggtttc | ggtatgaccg | acttcgttgg | cactaacgcg | 1320 |
| tgttggcgtc | gcgaagttct | gaacgagatc | ggtggcttcg | tttatggtag | cgtgactgaa | 1380 |
| gacaccctga | ctagcaacga | agttcatcgc | cgtggctaca | ttagccgcta | cgctgacgaa | 1440 |
| gacctgtgct | ggggtgaagc | accagttacc | gttgcagcag | ctctgctgca | gcgtcaacgt | 1500 |
| tgggctaaag | gtgccatcat | gaacggtatg | cgtatcttca | aaggtgctgc | taaagaacgc | 1560 |
| aaagaaatgc | tgctgagccg | tgagaaaccg | tctgaactgt | ctgagttcta | cgcatatcgt | 1620 |
| cgtcagcagc | gtaaaccaaa | caacactttc | gtttctacca | tgttctggct | ggattctact | 1680 |
| ctgtacccac | tgctggggttg | gggtgctttc | ggttacgtgt | tctgtgctat | cttccacctg | 1740 |
| atcaccgctc | aggcaccgat | ctctccgacc | tctactcaga | gcctggctgg | tgcgtttgtg | 1800 |
| acctactatc | tgattcgtta | cggtgcattc | ttctctgcct | tctatgaagt | gaacatgacc | 1860 |
| gacgttctgc | gctctcagca | gtgttggttc | tcttactcct | tcgcccacac | tgtgggtgta | 1920 |
| tgggatgctc | tgttttggtgg | tgccaagttt | ggctgggttg | ctaacactgg | ccaacgtcat | 1980 |
| cgccgtagct | ggctggaatg | gttcaacatc | ctgactctgg | gtgctctgct | gtccggcatt | 2040 |
| gtgtggcgtc | tgttcgcgtt | cattgttatc | gaagaagcgt | gttctccgta | cgagaacttc | 2100 |

```
ggtgctgttg cattcggcgg ttacgtagcg tggatgatgg ctccagttgc tctggttagc    2160
ctgaacgaac gcctgtcttc cgctgacgaa tccgagcgtg aaggtaaacc gatgccagtg    2220
ccgactccga tcatcgctgc tgccctgact atcctgggtg ttgtgttcct gtctggttgg    2280
gcaaacgctc gttgtggtat cgaagctcgc ggttaaaagc ttctcgag                 2328

<210> SEQ ID NO 2
<211> LENGTH: 1367
<212> TYPE: DNA
<213> ORGANISM: Oryza japonica

<400> SEQUENCE: 2
ctcgagaagc ttttagctgg tagtggagat cttagctttc acatccaggt tctctttatc     60
atcgatcggt ttggtagtct ggttgcgaac acgcttgatc ttcggagact ccaggccttt    120
gtgagcgaaa ccgtacagac gcagaacctg gttgtcagca aagttgaacg cacgctccat    180
agaacgcaga caacgttcaa ccggatagtc gccgtaagaa ccgcacggtt tgcagcccac    240
gaagtgagtc acaaatggcc agcgttcgtc acccagacct gggtggtggt tttccatcat    300
ttcttcgtac ttatctacca gacctgccca gaagccgtgc aggtagtagc tgttttcgat    360
aaacactttg ttcatccact tctccttctg gctcagcagc aggtagatca gggcagactg    420
gtcatccgcc tcgaacgctg gacgacccct caggttcgcg gtcagaatct tgcctgcttc    480
atcacggata aacctttcg gacccatcgg ggcccacgcg tccagcagat ccagggacca    540
ctggcagttg cggaacagga aggaaccggt gttcagagca atccaggaat gcttttcaaa    600
cagcagatcc tggtaaccgt gaataatcag gttgcgatcc tggtaacgag acagcggcag    660
ttcgaaagcc atgtcagtga acagtgcgtc gctgtccatc caccagatcc attcaacttc    720
cgggtgagac agcatcaggc gacgcagcag tggcagtttc gcccagtagc ctgccagttc    780
ggtgtccagg tgtgccaggt tatgtacgat ctcgatacca tgcagacgac agtaatcaat    840
tttgttctta gtagttttca gcagatagtg atcacccagt gggttgtcgc atggacctgg    900
ctggagccaa gtcaccagca ggatacgcgg tttgccacca gccacagtgg acggaaagcc    960
tggattctga cgcagccaac gacgacgctg accatcccaa tcagaaatct ttggacccag   1020
tgcatagcgt tccactgcag atgcgtacgc tgcagcagcc tcagtagcgt tcagcgcggt   1080
cgcgttgaag ctgcctgcca gatcgcctgc agccgctgca tcgtcgtcgg caccaccgtc   1140
agagcggatc tcacgcagaa tgcgatcgat atcttcaacc gcctttgcac ctgccagagc   1200
gtctgcatcg gttggctggt ttggcaggct caggttcaga ccaatggtgc cacgcagtac   1260
cagaatagta accagaccac acagaacagt gatcttaacg ttgttgaagg tgcgatgaat   1320
cttacgagaa cgatgatggt gaccgtggga gctcagcgga gatgcac                 1367

<210> SEQ ID NO 3
<211> LENGTH: 1365
<212> TYPE: DNA
<213> ORGANISM: Medicago trunculata

<400> SEQUENCE: 3
ctcgagaagc ttttacggct gcggatagtc aaacggcaga gaagaaacac cgttgtcacc     60
cagatcctta tgaacgaagc cgaatttgcg cataacctgg ttatctgcaa agttcagggc    120
tttcttcatg ccgttccagc aagcgtccgc agtgtacatt tcgttatact tgccagaaca    180
cggctgacag ccagtgaagt gagtcacgaa tggacgacgc cagctgcctt taccatagcc    240
```

```
tgcatctttc aggtattctt cacggataac accatacgct tcggatactt tctcagcgta    300
gcgacgacgc agtttcggtt ccaccttctc gatgtcctcg tatttcttgc tgatgttgga    360
gaaagtttcc acgatctctt cccagtaacc ttcgaagtag tattcgcctt ccaggtagat    420
tttatcaccc cacttctctt tctcgatggc gatcaggtat gccagaccgg tttgatcatc    480
agattccggg aagaacttgt cttttgaaagt gctacgcagg gtcttacccc attcttcgta    540
gtctggagac tgtggaccca tgccagccca tgcctccatg aagtccaggc tccattgaca    600
gttacgaatc aggaacacac ctgcgttcag accggtccag ctgcgtttct cgtggatcag    660
gtgtggccag ccgtgtacca ccaggttatg gtccttgtaa cgtttcagtg gcagcttgaa    720
atccatgtca gtgaacagcg catcgctatc caccccaccaa atccattcag cttctgggtg    780
agccatcata gcggctttca ctaccggata ctttgcccaa tacgcaaaca ttttcggatg    840
cagcagtgca ttgttgtaga agatgtcgta gccgtggatg cgggagtaat ctactttgtt    900
cttgaagaag cgcagcagca gatggtcacc aatcggattc ttacacgagg acggttggga    960
gccagtcacc atcagcacgc gttctttttgc acctgcagag aaagacgggt ggtgtttcag   1020
ccattcttca cgcttctcat cccagtcttc cagtttcacg acatggtat attccatttc    1080 cggatcgtcg tagaaggtct ggtccggtgg gtcgaaacgc aggtccggag tagagtaaga   1140
tacaacattg ttcttatggc tcttcagagt caggttgtcg ttcgggatcg gattagtgaa   1200
agaggagaag ccccaaacca gcagcagtgc gctgaatgca ccacccagga acaggaaacc   1260
atcagacaga aagatgctgg aagatttgtt acgcgggatc ggtttcgcca tgatgctgct   1320
gaagtgagaa tgagacagtt cggtagtaac catggtaccg gatcc             1365
```

<210> SEQ ID NO 4
<211> LENGTH: 1332
<212> TYPE: DNA
<213> ORGANISM: Cyamopsis tetragonoloba

<400> SEQUENCE: 4

```
ggatccggta ccatggcgaa gtttggtagc cgtaataagt ctccgaagtg gatctctaac     60
ggctgctgct tcctgctggg tgcctttact gctctgctgc tgctgtgggg tctgtgctcc    120
tttattatcc cgattccgaa caccgatccg aagctgaact ctgtagcgac ctctctgcgt    180
tctctgaact tcccgaagaa cccagcagct accctgccac cgaacctgca gcatgatcca    240
ccggatacta ctttctacga cgatccggaa acctcttata ctatggataa accgatgaag    300
aactgggacg agaaacgtaa ggaatggctg ctgcatcacc cgtccttcgg cgcagctgct    360
cgtgacaaga tcctgctggt aaccggttcc cagccgaaac gctgtcacaa cccgattggt    420
gatcacctgc tgctgcgttt ctttaagaac aaagtggatt actgccgtct gcataattac    480
gatatcatct ataacaacgc actgctgcac ccgaaaatga actcctattg ggctaagtac    540
ccagtgatcc gtgctgcaat gatggctcat ccggaagttg aatgggtgtg gtgggttgac    600
tctgacgctg tattcactga catggagttt aaactgccac tgaaacgcta taagaaccac    660
aatctggtgg tgcatggttg ggaaggtctg gtacgtctga ccactcctg gactggtctg    720 aacgcaggtg tattcctgat ccgtaattgc caatggagcc tggagttcat ggatgtatgg    780
gttagcatgg gtccacaaac tccagaatac gagaaatggg gtgagcgtct cgcgcgaaacc    840 ttcaaagata aagttctgcc agactctgat gaccagactg cactggcata cctgatcgca    900
accgataaca agacctg gcgtgagaaa atcttcctgg aaagcgagta ctacttcgaa    960
ggctattggc tggaaatcgt aaagacttac gagaacatct ccgaacgtta cgatgaagtt   1020
```

```
gaacgcaaag tagaaggtct gcgtcgtcgc cacgctgaga aggttagcga gaaatacggt    1080
gcaatgcgtg aagaatacct gaaagataac aaacgtcgtc cgttcatcac ccatttcact    1140
ggttgccagc cgtgcaacgg tcaccataac ccagcataca atgcgaacga ctgttggaat    1200
ggtatggaac gtgcactgaa ctttgcagat aaccagatcc tgcgtaccta cggttaccat    1260
cgtcagaatc tgctggacaa gtccgtttct ccactgccgt tcggttatcc agcagcttaa    1320
aagcttctcg ag                                                       1332

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
taatacgact cactataggg                                                 20

<210> SEQ ID NO 6
<211> LENGTH: 1386
<212> TYPE: DNA
<213> ORGANISM: Artificial Sequence
<220> FEATURE:
<223> OTHER INFORMATION: Synthetic Construct

<400> SEQUENCE: 6
ctcgaggaat tctcactgga acagcgcgtc actcgacagg ccattcttct ccagaatctc      60
ccgcaggcgc ttcagcgcct cgacctggat ctgacgaacc cgctcgcggg tcaggccgat     120
ttcctggccg acctcttcca gcgtgctgct ttcgtgaccg cgcaagccga agcggcgaat     180
caccacctca cgctgcttgt cggtgagttc cgtcagctgc tttcgctgag atcgtcatcc     240
tgcagcagct cgcacggatc ggtggggcga tcgtcggtga gcgtatccag cagggtcttg     300
tccgagtccg gaccaagaga gacgtctacc gaagtcaccc gttcgttcag gccgagcatg     360
cgcttgacct cggcgaccgg cttctccagc aggttggcga tttcttcggg tgaaggttcg     420
tggtcgagct tgtgggtcag ttcccgcgcc gcacgcaggt agacgttgag ctccttgacc     480
acatggatcg gcaagcgaat ggtccgggtc tggttcatga tggcccgctc gatggtctgg     540
cggatccacc aggtggcgta ggtcgagaac cggaatccgc gctccggatc gaacttctcc     600
acggcgcgga tcaggcctag gttgccttcc tcgatcaggt cgagcaggga cagtccgcga     660
ttgacatagc gccgggcgat cttcaccacc aaccgcaggt tgctctcgat catccgcttc     720
cgaccagcgg gatcgccctt ctgcgccaga cgagcgaagt ggacttcctc ttcgggcgtc     780
aacaggggcg agaaaccgat tcgttgaga tacagctgcg ttgcgtccaa cgcgcgcgtg      840
tagtcgatgt gcttgtgttg tttggaagag aaggaagtgg tggcttttgg agttgcccgg     900
ggagaaggct gctcgtcggc agacgactcg tccagcatga tgcccgggctc caggaggagc    960 acttcatcat cgtggtcaaa ctccggccct tcttttttga gtgccatgtc gttatccctt    1020
gcatgagttc gactcaagcc cgggcgattc ctttcccgct ggacacgccc ggacccgctc    1080
acctacatga tgtgggcggg cgaactcccg gtcagcgacg tggcaaatat tgcagtggat    1140
cgacaggctt accctggcgg cgaatctcga agtgcagctt cacccgatcg gttcctgtgg    1200
agcccatctc ggcaatcgat tgccctacct tgacctgttg cccttcccgc accagcagcc    1260
tgcggttgtg accgtaggca ctcacgtagg tctcgttgtg tttgatgatg accaactcgc    1320
```

```
cgtagccccg caaaccacta ccggcgtata caacggtccc accagacgca gccaggtacc    1380
aagctt                                                               1386

<210> SEQ ID NO 7
<211> LENGTH: 890
<212> TYPE: DNA
<213> ORGANISM: Artificial Sequence
<220> FEATURE:
<223> OTHER INFORMATION: Synthetic Construct

<400> SEQUENCE: 7
ggattcaaag aggagaaata ctagatggtg agcaagggcg aggagctgtt caccggggtg      60
gtgcccatcc tggtcgagct ggacggcgac gtaaacggcc acaagttcag cgtgtccggc     120
gagggcgagg gcgatgccac ctacggcaag ctgaccctga agttcatctg caccaccggc     180
aagctgcccg tgccctggcc caccctcgtg accaccttcg gctacggcct gcaatgcttc     240
gcccgctacc ccgaccacat gaagctgcac gacttcttca gtccgccat gcccgaaggc     300 tacgtccagg agcgcaccat cttcttcaag gacgacggca actacaagac ccgcgccgag     360
gtgaagttcg agggcgacac cctggtgaac cgcatcgagc tgaagggcat cgacttcaag     420
gaggacggca acatcctggg gcacaagctg gagtacaact acaacagcca caacgtctat     480
atcatggccg acaagcagaa gaacggcatc aaggtgaact tcaagatccg ccacaacatc     540
gaggacggca gcgtgcagct cgccgaccac taccagcaga cacccccat cggcgacggc     600 cccgtgctgc tgcccgacaa ccactacctg agctaccagt ccgccctgag caaagacccc     660
aacgagaagc gcgatcacat ggtcctgctg gagttcgtga ccgccgccgg gatcactctc     720
ggcatggacg agctgtacaa gtaataatac tagagccagg catcaaataa acgaaaggc      780 tcagtcgaaa gactgggcct ttcgttttat ctgttgtttg tcggtgaacg ctctctacta     840
gagtcacact ggctcacctt cgggtgggcc tttctgcgtt tataaagctt                890

<210> SEQ ID NO 8
<211> LENGTH: 11513
<212> TYPE: DNA
<213> ORGANISM: Artificial Sequence
<220> FEATURE:
<223> OTHER INFORMATION: Synthetic Construct

<400> SEQUENCE: 8
acggattaga agccgccgag cgggtgacag ccctccgaag gaagactctc ctccgtgcgt      60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caatgtaat aaaagtatca acaaaaaatt gttaatatac     420
ctctatactt taacgtcaag gagaaaaaac cccggatcgg actactagca gctgtaatac    480
gactcactat agggaatatt aagcttacca tggagactgt cgtccaggt tgttttcgtg    540 ctgttgtttc tgttccactg ggtcgtctga cttactcttt cctggtggac ggtcagccga    600
agtacaaccc ggactgtccg actctggtta acgaagctgg cgtgcgtgtg aacgtacgcc    660
acggtggttc tgacgtgat tgcgacggtg aagctgacga agaatggggt aaaggtcgtc    720
caagccgtgc tcgtcgcgtg ctgagccagg tttctggcct ggacctgtac tctcagcact    780
```

```
ccaccagcga catcgtttct atgctggtgt tccgtttctt ctacctggct atgattccag        840
ctggtgccta ctacttcttc tggctgagcg ttcgtggtgg taatcgccag gctccagttt        900
gctgggtggt gttcgttatg agcgaaatcc tgtctttcgt tagcgcgctg atttccctgt        960
ttggcatgtg aagccgatc aaacgtcgtt ggcgctctct ggacgctctg cgtccagctc        1020
tgccagttgc agattggcca actgtagacg tgatcatttg ccactacaaa gaggacaccg       1080
aacagctgcg tcagactatt cgtgcagcga tgaaactgga ttacccagcc catctgctgc       1140
acattctgat tgccgacgat ggcttcttcc caacctccaa gatggtagag cgttctgata       1200
ttggtctggc tctgtaccag acctgtgttg aggaagcggg ttatgatccg ctgctggaag       1260
aaaccatgaa tgaacgtggt ctggttgaac actatactgt taaggcaggt gacgacctgc       1320
cgcgtcatga ttgcgcggtt gaagctcacc agttcgagtt tggtccgtat ggtgcggaca       1380
tgtacggtcc aggtgccctg ccacgtctgt ccctggttgc tcgtgtgaag ccggctgacg       1440
ctcacaacaa ggcaggcaac atcaacaacg tactgtccaa ctctaacgca gaaggtaaga       1500
ttgttctgtt cctggatgct gacatgaagc cggtagaatc ttacctgctg cgtgttctgc       1560
cactgatgct ggaagagcag cgttccgata gcctgcagag ccaactgatc caggcagagg       1620
acccagagct gggtgctggt acttctaaga gctggcaaat caaccgtgac attggcttcg       1680
ttggctgccc acaacgcttc gcgaacgtat ccggtgacca tccggattac tgtgctcacc       1740
gtaacgcgat ctactacgac ggtatctgca ctggtcgtga tggtttcggt atgaccgact       1800
tcgttggcac taacgcgtgt tggcgtcgcg aagttctgaa cgagatcggt ggcttcgttt       1860
atggtagcgt gactgaagac accctgacta gcaacgaagt tcatcgccgt ggctacatta       1920
gccgctacgc tgacgaagac ctgtgctggg gtgaagcacc agttaccgtt gcagcagctc       1980
tgctgcagcg tcaacgttgg gctaaaggtg ccatcatgaa cggtatgcgt atcttcaaag       2040
gtgctgctaa gaacgcaaa gaaatgctgc tgagccgtga gaaaccgtct gaactgtctg       2100
agttctacgc atatcgtcgt cagcagcgta accaaacaa cactttcgtt tctaccatgt       2160
tctggctgga ttctactctg tacccactgc tgggttgggg tgcttccggt tacgtgttct       2220
gtgctatctt ccacctgatc accgctcagg caccgatctc tccgacctct actcagagcc       2280
tggctggtgc gtttgtgacc tactatctga ttcgttacgg tgcattcttc tctgccttct       2340
atgaagtgaa catgaccgac gttctgcgct ctcagcagtg ttggttctct tactccttcg       2400
cccacactgt gggtgtatgg gatgctctgt ttggtggtgc caagtttggc tgggttgcta       2460
acactggcca acgtcatcgc cgtagctggc tggaatggtt caacatcctg actctgggtg       2520
ctctgctgtc cggcattgtg tggcgtctgt tcgcgttcat tgttatcgaa gaagcgtgtt       2580
ctccgtacga gaacttcggt gctgttgcat tcggcggtta cgtagcgtgg atgatggctc       2640
cagttgctct ggttagcctg aacgaacgcc tgtcttccgc tgacgaatcc gagcgtgaag       2700
gtaaaccgat gccagtgccg actccgatca tcgctgctgc cctgactatc ctgggtgttg       2760
tgttcctgtc tggttgggca acgctcgtt gtggtatcga agctcgcggt taaggtacct       2820
catgtaatta gttatgtcac gcttacattc acgccctccc cccacatccg ctctaaccga       2880
aaaggaagga gttagacaac ctgaagtcta ggtccctatt tatttttta tagttatgtt       2940
agtattaaga acgttattta tatttcaat tttctttttt tttctgtaca gacgcgtgta       3000
cgcatgtaac attatactga aaaccttgct tgagaaggtt ttgggacgct cgaaggcttt       3060
aatttgccgg attagaagcc gccgagcggg tgacagccct ccgaaggaag actctcctcc       3120
```

```
gtgcgtcctc gtcttcaccg gtcgcgttcc tgaaacgcag atgtgcctcg cgccgcactg    3180
ctccgaacaa taaagattct acaatactag cttttatggt tatgaagagg aaaaattggc    3240
agtaacctgg ccccacaaac cttcaaatga acgaatcaaa ttaacaacca taggatgata    3300
atgcgattag ttttttagcc ttatttctgg ggtaattaat cagcgaagcg atgattttg     3360
atctattaac agatatataa atgcaaaaac tgcataacca ctttaactaa tactttcaac    3420
attttcggtt tgtattactt cttattcaaa tgtaataaaa gtatcaacaa aaaattgtta    3480
atatacctct atactttaac gtcaaggagg gatccatggc gaagtttggt agccgtaata    3540
agtctccgaa gtggatctct aacggctgct gcttcctgct gggtgccttt actgctctgc    3600
tgctgctgtg gggtctgtgc tcctttatta tcccgattcc gaacaccgat ccgaagctga    3660
actctgtagc gacctctctg cgttctctga acttcccgaa gaacccagca gctaccctgc    3720
caccgaacct gcagcatgat ccaccggata ctactttcta cgacgatccg gaaacctctt    3780
atactatgga taaaccgatg aagaactggg acgagaaacg taaggaatgg ctgctgcatc    3840
acccgtcctt cggcgcagct gctcgtgaca agatcctgct ggtaaccggt tcccagccga    3900
aacgctgtca aacccgatt ggtgatcacc tgctgctgcg tttctttaag aacaaagtgg     3960
attactgccg tctgcataat tacgatatca tctataacaa cgcactgctg cacccgaaaa    4020
tgaactccta tgggctaag tacccagtga tccgtgctgc aatgatggct catccggaag     4080
ttgaatgggt gtggtgggtt gactctgacg ctgtattcac tgcatggag tttaaactgc     4140
cactgaaacg ctataagaac cacaatctgg tggtgcatgg ttgggaaggt ctggtacgtc    4200
tgaaccactc ctggactggt ctgaacgcag gtgtattcct gatccgtaat tgccaatgga    4260
gcctggagtt catggatgta tgggttagca tgggtccaca aactccagaa tacgagaaat    4320
ggggtgagcg tctgcgcgaa accttcaaag ataaagttct gccagactct gatgaccaga    4380
ctgcactggc atacctgatc gcaaccgata acaaagacac ctggcgtgag aaaatcttcc    4440
tggaaagcga gtactacttc gaaggctatt ggctggaaat cgtaaagact tacgagaaca    4500
tctccgaacg ttacgatgaa gttgaacgca agtagaagg tctgcgtcgt cgccacgctg     4560
agaaggttag cgagaaatac ggtgcaatgc gtgaagaata cctgaaagat aacaaacgtc    4620
gtccgttcat cacccattc actggttgcc agccgtgcaa cggtcaccat aacccagcat     4680
acaatgcgaa cgactgttgg aatggtatgg aacgtgcact gaactttgca gataaccaga    4740
tcctgcgtac ctacggttac catcgtcaga atctgctgga caagtccgtt tctccactgc    4800
cgttcggtta tccagcagct taagaattct catgtaatta gttatgtcac gcttacattc    4860
acgccctccc cccacatccg ctctaaccga aaaggaagga gttagacaac ctgaagtcta    4920
ggtccctatt tattttttta tagttatgtt agtattaaga acgttattta tatttcaaat    4980
ttttcttttt tttctgtaca gacgcgtgta cgcatgtaac attatactga aaaccttgct    5040
tgagaaggtt ttgggacgct cgaaggcttt aatttgccgg attagaagcc gccgagcggg    5100
tgacagccct ccgaaggaag actctcctcc gtgcgtcctc gtcttcaccg gtcgcgttcc    5160
tgaaacgcag atgtgcctcg cgccgcactg ctccgaacaa taaagattct acaatactag    5220
cttttatggt tatgaagagg aaaaattggc agtaacctgg ccccacaaac cttcaaatga    5280
acgaatcaaa ttaacaacca taggatgata atgcgattag ttttttagcc ttatttctgg    5340
ggtaattaat cagcgaagcg atgattttg atctattaac agatatataa atgcaaaaac     5400
tgcataacca ctttaactaa tactttcaac attttcggtt tgtattactt cttattcaaa    5460
tgtaataaaa gtatcaacaa aaaattgtta atatacctct atactttaac gtcaaggagg    5520
```

```
cggccgccat ggtgagcaag ggcgaggagc tgttcaccgg ggtggtgccc atcctggtcg    5580
agctggacgg cgacgtaaac ggccacaagt tcagcgtgtc cggcgagggc gagggcgatg    5640
ccacctacgg caagctgacc ctgaagttca tctgcaccac cggcaagctg cccgtgccct    5700
ggcccaccct cgtgaccacc ttcggctacg gcctgcaatg cttcgcccgc taccccgacc    5760
acatgaagct gcacgacttc ttcaagtccg ccatgcccga aggctacgtc caggagcgca    5820
ccatcttctt caaggacgac ggcaactaca agacccgcgc cgaggtgaag ttcgagggcg    5880
acaccctggt gaaccgcatc gagctgaagg gcatcgactt caaggaggac ggcaacatcc    5940
tggggcacaa gctggagtac aactacaaca gccacaacgt ctatatcatg gccgacaagc    6000
agaagaacgg catcaaggtg aacttcaaga tccgccacaa catcgaggac ggcagcgtgc    6060
agctcgccga ccactaccag cagaacaccc ccatcggcga cggccccgtg ctgctgcccg    6120
acaaccacta cctgagctac cagtccgccc tgagcaaaga ccccaacgag aagcgcgatc    6180
acatggtcct gctggagttc gtgaccgccg ccgggatcac tctcggcatg gacgagctgt    6240
acaagtaata atctagaggg ccgcatcatg taattagtta tgtcacgctt acattcacgc    6300
cctcccccca catccgctct aaccgaaaag gaaggagtta gacaacctga agtctaggtc    6360
cctatttatt ttttatagt tatgttagta ttaagaacgt tatttatatt tcaaattttt    6420
cttttttttc tgtacagacg cgtgtacgca tgtaacatta tactgaaaac cttgcttgag    6480
aaggttttgg gacgctcgaa ggctttaatt tgcggccctg cattaatgaa tcggccaacg    6540
cgcggggaga ggcggtttgc gtattgggcg ctcttccgct tcctcgctca ctgactcgct    6600
gcgctcggtc gttcggctgc ggcgagcggt atcagctcac tcaaaggcgg taatacggtt    6660
atccacagaa tcaggggata acgcaggaaa gaacatgtga gcaaaaggcc agcaaaagcc    6720
caggaaccgt aaaaaggccg cgttgctggc gtttttccat aggctccgcc ccctgacga    6780 gcatcacaaa aatcgacgct caagtcagag gtggcgaaac ccgacaggac tataaagata    6840
ccaggcgttt ccccctggaa gctccctcgt gcgctctcct gttccgaccc tgccgcttac    6900
cggatacctg tccgcctttc tcccttcggg aagcgtggcg ctttctcata gctcacgctg    6960
taggtatctc agttcggtgt aggtcgttcg ctccaagctg ggctgtgtgc acgaacccc    7020 cgttcagccc gaccgctgcg ccttatccgg taactatcgt cttgagtcca acccggtaag    7080
acacgactta tcgccactgg cagcagccac tggtaacagg attagcagag cgaggtatgt    7140
aggcggtgct acagagttct tgaagtggtg gcctaactac ggctacacta aaggacagt    7200 atttggtatc tgcgctctgc tgaagccagt taccttcgga aaaagagttg gtagctcttg    7260
atccggcaaa caaaccaccg ctggtagcgg tggttttttt gtttgcaagc agcagattac    7320
gcgcagaaaa aaggatctc aagaagatcc tttgatcttt tctacggggt ctgacgctca    7380
gtggaacgaa aactcacgtt aagggatttt ggtcatgaga ttatcaaaaa ggatcttcac    7440
ctagatcctt ttaaattaaa aatgaagttt taaatcaatc taaagtatat atgagtaaac    7500
ttggtctgac agttaccaat gcttaatcag tgaggcacct atctcagcga tctgtctatt    7560
tcgttcatcc atagttgcct gactccccgt cgtgtagata actacgatac gggagcgctt    7620
accatctggc cccagtgctg caatgatacc gcgagaccca cgctcaccgg ctccagattt    7680
atcagcaata aaccagccag ccggaagggc cgagcgcaga agtggtcctg caactttatc    7740
cgcctccatc cagtctatta attgttgccg ggaagctaga gtaagtagtt cgccagttaa    7800
tagtttgcgc aacgttgttg gcattgctac aggcatcgtg gtgtcactct cgtcgtttgg    7860
```

```
tatggcttca ttcagctccg gttcccaacg atcaaggcga gttacatgat cccccatgtt    7920
gtgcaaaaaa gcggttagct ccttcggtcc tccgatcgtt gtcagaagta agttggccgc    7980
agtgttatca ctcatggtta tggcagcact gcataattct cttactgtca tgccatccgt    8040
aagatgcttt tctgtgactg gtgagtactc aaccaagtca ttctgagaat agtgtatgcg    8100
gcgaccgagt tgctcttgcc cggcgtcaat acgggataat agtgtatcac atagcagaac    8160
tttaaaagtg ctcatcattg gaaaacgttc ttcggggcga aaactctcaa ggatcttacc    8220
gctgttgaga tccagttcga tgtaacccac tcgtgcaccc aactgatctt cagcatcttt    8280
tactttcacc agcgtttctg ggtgagcaaa aacaggaagg caaaatgccg caaaaaaggg    8340
aataagggcg acacggaaat gttgaatact catactcttc cttttcaat gggtaataac     8400 tgatataatt aaattgaagc tctaatttgt gagtttagta tacatgcatt tacttataat    8460
acagtttttt agttttgctg ccgcatcttc tcaaatatg cttcccagcc tgcttttctg     8520
taacgttcac cctctacctt agcatcccctt ccctttgcaa atagtcctct tccaacaata   8580
ataatgtcag atcctgtaga gaccacatca tcccacgttc tatactgttg acccaatgcg    8640
tctcccttgt catctaaacc cacaccgggt gtcataatca accaatcgta accttcatct    8700
cttccaccca tgtctctttg agcaataaag ccgataacaa aatctttgtc gctcttcgca    8760
atgtcaacag tacccttagt atattctcca gtagataggg agcccttgca tgacaattct    8820
gctaacatca aaaggcctct aggttccttt gttacttctt ctgccgcctg cttcaaaccg    8880
ctaacaatac ctgggcccac cacaccgtgt gcattcgtaa tgtctgccca ttctgctatt    8940
ctgtatacac ccgcagagta ctgcaatttg actgtattac caatgtcagc aaattttctg    9000
tcttcgaaga gtaaaaaatt gtacttggcg gataatgcct ttagcggctt aactgtgccc    9060
tccatggaaa aatcagtcaa gatatccaca tgtgttttta gtaaacaaat tttgggacct    9120
aatgcttcaa ctaactccag taattccttg gtggtacgaa catccaatga agcacacaag    9180
tttgtttgct tttcgtgcat gatattaaat agcttggcag caacaggact aggatgagta    9240
gcagcacgtt ccttatatgt agctttcgac atgatttatc ttcgtttcct gcaggttttt    9300
gttctgtgca gttgggttaa gaatactggg caatttcatg tttcttcaac actacatatg    9360
cgtatatata ccaatctaag tctgtgctcc ttccttcgtt cttccttctg ttcggagatt    9420
accgaatcaa aaaatttca aagaaaccga aatcaaaaaa aagaataaaa aaaaatgat     9480 gaattgaatt gaaaagctag cttatcgatg ataagctgtc aaagatgaga attaattcca    9540
cggactatag actatactag atactccgtc tactgtacga tacacttccg ctcaggtcct    9600
tgtcctttaa cgaggcctta ccactctttt gttactctat tgatccagct cagcaaaggc    9660
agtgtgatct aagattctat cttcgcgatg tagtaaaact agctagaccg agaaagagac    9720
tagaaatgca aaaggcactt ctacaatggc tgccatcatt attatccgat gtgacgctgc    9780
agcttctcaa tgatattcga atacgctttg aggagataca gcctaatatc cgacaaactg    9840
ttttacagat ttacgatcgt acttgttacc catcattgaa ttttgaacat ccgaacctgg    9900
gagttttccc tgaaacagat agtatatttg aacctgtata ataatatata gtctagcgct    9960
ttacggaaga caatgtatgt atttcggttc ctggagaaac tattgcatct attgcatagg   10020
taatcttgca cgtcgcatcc ccggttcatt ttctgcgttt ccatcttgca cttcaatagc   10080
atatctttgt taacgaagca tctgtgcttc attttgtaga acaaaaatgc aacgcgagag   10140
cgctaatttt tcaaacaaag aatctgagct gcatttttac agaacagaaa tgcaacgcga   10200
aagcgctatt ttaccaacga agaatctgtg cttcattttt gtaaaacaaa aatgcaacgc   10260
```

-continued

```
gacgagagcg ctaattttc  aaacaaagaa tctgagctgc attttacag  aacagaaatg  10320
caacgcgaga gcgctatttt accaacaaag aatctatact tcttttttgt tctacaaaaa  10380
tgcatcccga gagcgctatt tttctaacaa agcatcttag attactttt  ttctcctttg  10440
tgcgctctat aatgcagtct cttgataact ttttgcactg taggtccgtt aaggttagaa  10500
gaaggctact ttggtgtcta ttttctcttc cataaaaaaa gcctgactcc acttcccgcg  10560
tttactgatt actagcgaag ctgcgggtgc attttttcaa gataaaggca tccccgatta  10620
tattctatac cgatgtggat tgcgcatact ttgtgaacag aaagtgatag cgttgatgat  10680
tcttcattgg tcagaaaatt atgaacggtt tcttctattt tgtctctata tactacgtat  10740
aggaaatgtt tacattttcg tattgttttc gattcactct atgaatagtt cttactacaa  10800
ttttttgtc  taaagagtaa tactagagat aaacataaaa aatgtagagg tcgagtttag  10860
atgcaagttc aaggagcgaa aggtggatgg gtaggttata tagggatata gcacagagat  10920
atatagcaaa gagatacttt tgagcaatgt ttgtggaagc ggtattcgca atgggaagct  10980
ccaccccggt tgataatcag aaaagcccca aaaacaggaa gattgtataa gcaaatattt  11040
aaattgtaaa cgttaatatt ttgttaaaat tcgcgttaaa ttttttgttaa atcagctcat  11100
tttttaacga atagcccgaa atcggcaaaa tcccttataa atcaaaagaa tagaccgaga  11160
tagggttgag tgttgttcca gtttccaaca agagtccact attaaagaac gtggactcca  11220
acgtcaaagg gcgaaaaagg gtctatcagg gcgatggccc actacgtgaa ccatcaccct  11280
aatcaagttt tttggggtcg aggtgccgta aagcagtaaa tcggaagggt aaacggatgc  11340
ccccatttag agcttgacgg ggaaagccgg cgaacgtggc gagaaaggaa gggaagaaag  11400
cgaaaggagc gggggctagg gcggtgggaa gtgtaggggt cacgctgggc gtaaccacca  11460
caccccgccgc gcttaatggg gcgctacagg gcgcgtgggg atgatccact agt         11513
```

<210> SEQ ID NO 9
<211> LENGTH: 1237
<212> TYPE: DNA
<213> ORGANISM: Micrococcus sp. HL-2003

<400> SEQUENCE: 9

```
ggatccggta ccatggtgtt tatcgtcaat cttttctcct gcaccttatc tgaaaccacg    60
gttagctcaa taaaatctga agctacggtt agctcaacat ttactgccgt cacggccctg   120
caattggtgg ctgagggtaa gttgcagtcg gcgaagggtt tcggtggtgg tacgattcac   180
tacccaaccc tcgcggccga agcacccttgg tggacgccgg gccaaggcca tggttacgag   240
gcgatcacct acggctggct ggtcggcgaa ctgctgcgcc gcgccgatgg gcgtgggcct   300
ggtctgttag gcgctattgc cgtggttcct ggttacgttt cttacgagaa ctctatcaag   360
tggtggggac cgcgtctggc ttcttggggc tttgtcgttg cacggccgtt gggcctggac   420
tttcatgtgg gcctggcgga tgaagagttt atcgtgttg  cccatatagc gcgcagcaaa   480
gccaatgcag cactagataa cattgctgat gacaccgtcg gcagtataga tcctaagcgg   540
ttgggcgcta ttggctggtc aggtggcggc ggcgcgctta aactggcaac ggagcgcagc   600
acagtacgag ccattttgac cagtactaat aaacctgaat ggcgacgctt cgataaattc   660
ttatgtgcct gcgaggatga ccggattgct gagactaaga aatatgccaa cgcgttttat   720
aaaaatgccg acatgctcga agagttgacc cgtgaacaca gtatcgggcc ggataaaaca   780
ttattgacac aaactcggtt tggcttgggg tgcttggatc aaccgcaagc aggggttaaa   840
```

```
attcattttg aagagtacct tgatcaaacc catggattta tcaatttgac gccagtttca    900
cataaggcga gagcaaatct gattcagatg cctaatgcca cattcggcct tggcccgcgt    960
gcttttgggc atcctggtgc aggtggatcg gtaggttttg ccgaccccga acacgatgta   1020
gcgtttggtt tcgtgactaa tacattgggg ccttatgtag ttgagtttaa aagccgtcat   1080
ccctcatttt atgcatataa agatggattg gtgctgactg gaaatgacgt cgactatgtg   1140
actgattact atgcaacaaa gcatgctgta catttagatg atccacgtgc acagaagttg   1200
gtcggaatat tggccggttg tctgtaagct tctcgag                            1237

<210> SEQ ID NO 10
<211> LENGTH: 13440
<212> TYPE: DNA
<213> ORGANISM: Artificial Sequence
<220> FEATURE:
<223> OTHER INFORMATION: Synthetic construct

<400> SEQUENCE: 10
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caatgtaat aaaagtatca acaaaaaatt gttaatatac     420
ctctatactt taacgtcaag gagaaaaaac cccggatcgg actactagca gctgtaatac    480
gactcactat agggaatatt aagcttgcca ccatggtgtt tatcgtcaat ctttctcct    540 gcaccttatc tgaaaccacg gttagctcaa taaaatctga agctacggtt agctcaacat    600
ttactgccgt cacggccctg caattggtgg ctgagggtaa gttgcagtcg gcgaagggtt    660
tcggtggtgg tacgattcac tacccaaccc tcgcggccga agcaccctgg tggacgccgg    720
gccaaggcca tggttacgag gcgatcacct acggctggct ggtcggcgaa ctgctgcgcc    780
gcgccgatgg gcgtgggcct ggtctgttag gcgctattgc cgtggttcct ggttacgttt    840
cttacgagaa ctctatcaag tggtggggac gcgtctggc ttcttggggc tttgtcgttg     900
cacggccgtt gggcctggac tttcatgtgg gcctggcgga tgaagagttt tatcgtgttg    960
cccatatagc gcgcagcaaa gccaatgcag cactagataa cattgctgat gacaccgtcg   1020
gcagtataga tcctaagcgg ttgggcgcta ttggctggtc aggtggcggc ggcgcgctta   1080
aactggcaac ggagcgcagc acagtacgag ccattttgac cagtactaat aaacctgaat   1140
ggcgacgctt cgataaattc ttatgtgcct gcgaggatga ccggattgct gagactaaga   1200
aatatgccaa cgcgttttat aaaaatgccg acatgctcga agagttgacc cgtgaacaca   1260
gtatcgggcc ggataaaaca ttattgacac aaactcggtt tggcttgggg tgcttggatc   1320
aaccgcaagc aggggttaaa attcattttg aagagtacct tgatcaaacc catggattta   1380
tcaatttgac gccagtttca cataaggcga gagcaaatct gattcagatg cctaatgcca   1440
cattcggcct tggcccgcgt gcttttgggc atcctggtgc aggtggatcg gtaggttttg   1500
ccgaccccga acacgatgta gcgtttggtt tcgtgactaa tacattgggg ccttatgtag   1560
ttgagtttaa aagccgtcat ccctcatttt atgcatataa agatggattg gtgctgactg   1620
gaaatgacgt cgactatgtg actgattact atgcaacaaa gcatgctgta catttagatg   1680
```

```
atccacgtgc acagaagttg gtcggaatat tggccggttg tctgtaaccc gggtaatcat    1740
gtaattagtt atgtcacgct tacattcacg ccctccccccc acatccgctc taaccgaaaa    1800
ggaaggagtt agacaacctg aagtctaggt ccctatttat tttttttatag ttatgttagt    1860
attaagaacg ttatttatat ttcaaatttt tcttttttttt ctgtacagac gcgtgtacgc    1920
atgtaacatt atactgaaaa ccttgcttga aaggttttg ggacgctcga aggctttaat    1980
ttgccggatt agaagccgcc gagcgggtga cagccctccg aaggaagact ctcctccgtg    2040
cgtcctcgtc ttcaccggtc gcgttcctga acgcagatg tgcctcgcgc cgcactgctc    2100
cgaacaataa agattctaca atactagctt ttatggttat gaagaggaaa aattggcagt    2160
aacctggccc cacaaaccctt caaatgaacg aatcaaatta caaccatag gatgataatg    2220
cgattagttt tttagcctta tttctggggt aattaatcag cgaagcgatg attttgatc    2280
tattaacaga tatataaatg caaaaactgc ataaccactt taactaatac tttcaacatt    2340
ttcggtttgt attacttctt attcaaatgt aataaaagta tcaacaaaaa attgttaata    2400
tacctctata ctttaacgtc aaggaggcgc gccaccatgg agactgttcg tccaggttgt    2460
tttcgtgctg ttgtttctgt tccactgggg cgtctgactt actctttcct ggtggacggt    2520
cagccgaagt acaacccgga ctgtccgact ctggttaacg aagctggcgt gcgtgtgaac    2580
gtacgccacg gtggttctga cggtgattgc gacggtgaag ctgacgaaga atggggtaaa    2640
ggtcgtccaa gccgtgctcg tcgcgtgctg agccaggttt ctggcctgga cctgtactct    2700
cagcactcca ccagcgacat cgtttctatg ctggtgttcc gtttcttcta cctggctatg    2760
attccagctg gtgcctacta cttcttctgg ctgagcgttc gtggtggtaa tcgccaggct    2820
ccagtttgct gggtggtgtt cgttatgagc gaaatcctgt cttttcgttag cgcgctgatt    2880
tccctgtttg gcatgtggaa gccgatcaaa cgtcgttggc gctctctgga cgctctgcgt    2940
ccagctctgc cagttgcaga ttggccaact gtagacgtga tcatttgcca ctacaaagag    3000
gacaccgaac agctgcgtca gactattcgt gcagcgatga aactggatta cccagcccat    3060
ctgctgcaca ttctgattgc cgacgatggc ttcttcccaa cctccaagat ggtagagcgt    3120
tctgatattg gtctggctct gtaccagacc tgtgttgagg aagcgggtta tgatccgctg    3180
ctggaagaaa ccatgaatga acgtggtctg gttgaacact atactgttaa ggcaggtgac    3240
gacctgccgc gtcatgattg cgcggttgaa gctcaccagt tcgagtttgg tccgtatggt    3300
gcggacatgt acgtccagg tgccctgcca cgtctgtccc tggttgctcg tgtgaagccg    3360
gctgacgctc acaacaaggc aggcaacatc aacaacgtac tgtccaactc taacgcagaa    3420
ggtaagattg ttctgttcct ggatgctgac atgaagccgg tagaatctta cctgctgcgt    3480
gttctgccac tgatgctgga agagcagcgt tccgatagcc tgcagagcca actgatccag    3540
gcagaggacc cagagctggg tgctggtact tctaagagct ggcaaatcaa ccgtgacatt    3600
ggcttcgttg gctgcccaca acgcttcgcg aacgtatccg gtgaccatcc ggattactgt    3660
gctcaccgta acgcgatcta ctacgacggt atctgcactg tcgtgatgg tttcggtatg    3720
accgacttcg ttggcactaa cgcgtgttgg cgtcgcgaag ttctgaacga gatcggtggc    3780
ttcgtttatg gtagcgtgac tgaagacacc ctgactagca acgaagttca tcgccgtggc    3840
tacattagcc gctacgctga cgaagacctg tgctggggtg aagcaccagt taccgttgca    3900
gcagctctgc tgcagcgtca acgtttgggct aaaggtgcca tcatgaacgg tatgcgtatc    3960
ttcaaaggtg ctgctaaaga acgcaaagaa atgctgctga gccgtgagaa accgtctgaa    4020
```

```
ctgtctgagt tctacgcata tcgtcgtcag cagcgtaaac caaacaacac tttcgtttct    4080
accatgttct ggctggattc tactctgtac ccactgctgg gttggggtgc tttcggttac    4140
gtgttctgtg ctatcttcca cctgatcacc gctcaggcac cgatctctcc gacctctact    4200
cagagcctgg ctggtgcgtt tgtgacctac tatctgattc gttacggtgc attcttctct    4260
gccttctatg aagtgaacat gaccgacgtt ctgcgctctc agcagtgttg gttctcttac    4320
tccttcgccc acactgtggg tgtatgggat gctctgtttg gtggtgccaa gtttggctgg    4380
gttgctaaca ctggccaacg tcatcgccgt agctggctgg aatggttcaa catcctgact    4440
ctgggtgctc tgctgtccgg cattgtgtgg cgtctgttcg cgttcattgt tatcgaagaa    4500
gcgtgttctc cgtacgagaa cttcggtgct gttgcattcg gcggttacgt agcgtggatg    4560
atggctccag ttgctctggt tagcctgaac gaacgcctgt cttccgctga cgaatccgag    4620
cgtgaaggta aaccgatgcc agtgccgact ccgatcatcc tgctgccct gactatcctg     4680
ggtgttgtgt tcctgtctgg ttgggcaaac gctcgttgtg gtatcgaagc tcgcggttaa    4740
ggtacctcat gtaattagtt atgtcacgct tacattcacg ccctcccccc acatccgctc    4800
taaccgaaaa ggaaggagtt agacaacctg aagtctaggt ccctatttat tttttttatag   4860
ttatgttagt attaagaacg ttatttatat ttcaaatttt tctttttttt ctgtacagac    4920
gcgtgtacgc atgtaacatt atactgaaaa ccttgcttga aaggttttg gacgctcga     4980
aggctttaat ttgccggatt agaagccgcc gagcgggtga cagccctccg aaggaagact    5040
ctcctccgtg cgtcctcgtc ttcaccggtc gcgttcctga aacgcagatg tgcctcgcgc    5100
cgcactgctc cgaacaataa agattctaca atactagctt ttatggttat gaagaggaaa    5160
aattggcagt aacctggccc cacaaacctt caaatgaacg aatcaaatta caaccatag    5220
gatgataatg cgattagttt tttagcctta tttctggggt aattaatcag cgaagcgatg    5280
attttgatc tattaacaga tatataaatg caaaaactgc ataaccactt taactaatac    5340
tttcaacatt ttcggtttgt attacttctt attcaaatgt aataaaagta tcaacaaaaa    5400
attgttaata tacctctata ctttaacgtc aaggagggat ccatggcgaa gtttggtagc    5460
cgtaataagt ctccgaagtg gatctctaac ggctgctgct tcctgctggg tgcctttact    5520
gctctgctgc tgctgtgggg tctgtgctcc tttattatcc cgattccgaa caccgatccg    5580
aagctgaact ctgtagcgac ctctctgcgt tctctgaact cccgaagaa cccagcagct    5640
accctgccac cgaacctgca gcatgatcca ccggatacta ctttctacga cgatccggaa    5700
acctcttata ctatggataa accgatgaag aactgggacg agaaacgtaa ggaatggctg    5760
ctgcatcacc cgtccttcgg cgcagctgct cgtgacaaga tcctgctggt aaccggttcc    5820
cagccgaaac gctgtcacaa cccgattggt gatcacctgc tgctgcgttt ctttaagaac    5880
aaagtggatt actgccgtct gcataattac gatatcatct ataacaacgc actgctgcac    5940
ccgaaaatga actcctattg ggctaagtac ccagtgatcc gtgctgcaat gatggctcat    6000
ccggaagttg aatgggtgtg gtgggttgac tctgacgctg tattcactga catggagttt    6060
aaactgccac tgaaacgcta taagaaccac aatctggtgg tgcatggttg ggaaggtctg    6120
gtacgtctga ccactcctg gactggtctg aacgcaggtg tattcctgat ccgtaattgc    6180
caatggagcc tggagttcat ggatgtatgg gttagcatgg gtccacaaac tccagaatac    6240
gagaaatggg gtgagcgtct gcgcgaaacc ttcaaagata agttctgcc agactctgat    6300
gaccagactg cactggcata cctgatcgca accgataaca aagacacctg gcgtgagaaa    6360
atcttcctgg aaagcgagta ctacttcgaa ggctattggc tggaaatcgt aaagacttac    6420
```

```
gagaacatct ccgaacgtta cgatgaagtt gaacgcaaag tagaaggtct gcgtcgtcgc    6480
cacgctgaga aggttagcga gaaatacggt gcaatgcgtg aagaatacct gaaagataac    6540
aaacgtcgtc cgttcatcac ccatttcact ggttgccagc cgtgcaacgg tcaccataac    6600
ccagcataca atgcgaacga ctgttggaat ggtatggaac gtgcactgaa ctttgcagat    6660
aaccagatcc tgcgtaccta cggttaccat cgtcagaatc tgctggacaa gtccgtttct    6720
ccactgccgt tcggttatcc agcagcttaa gaattctcat gtaattagtt atgtcacgct    6780
tacattcacg ccctccccc acatccgctc taaccgaaaa ggaaggagtt agacaacctg     6840
aagtctaggt ccctatttat ttttttatag ttatgttagt attaagaacg ttatttatat    6900
ttcaaatttt tctttttttt ctgtacagac gcgtgtacgc atgtaacatt atactgaaaa    6960
ccttgcttga aaggttttg gacgctcga aggctttaat ttgccggatt agaagccgcc       7020
gagcgggtga cagccctccg aaggaagact ctcctcgtg cgtcctcgtc ttcaccggtc      7080
gcgttcctga aacgcagatg tgcctcgcgc cgcactgctc cgaacaataa agattctaca    7140
atactagctt ttatggttat gaagaggaaa aattggcagt aacctggccc cacaaacctt    7200
caaatgaacg aatcaaatta acaaccatag gatgataatg cgattagttt tttagcctta   7260
tttctggggt aattaatcag cgaagcgatg atttttgatc tattaacaga tatataaatg    7320
caaaaactgc ataaccactt taactaatac tttcaacatt ttcggtttgt attacttctt    7380
attcaaatgt aataaaagta tcaacaaaaa attgttaata tacctctata ctttaacgtc    7440
aaggaggcgg ccgccatggt gagcaagggc gaggagctgt tcaccggggt ggtgcccatc    7500
ctggtcgagc tggacggcga cgtaaacggc cacaagttca gcgtgtccgg cgagggcgag    7560
ggcgatgcca cctacggcaa gctgaccctg aagttcatct gcaccaccgg caagctgccc    7620
gtgccctggc ccaccctcgt gaccaccttc ggctacggcc tgcaatgctt cgcccgctac    7680
cccgaccaca tgaagctgca cgacttcttc aagtccgcca tgcccgaagg ctacgtccag    7740
gagcgcacca tcttcttcaa ggacgacggc aactacaaga cccgcgccga ggtgaagttc    7800
gagggcgaca ccctggtgaa ccgcatcgag ctgaagggca tcgacttcaa ggaggacggc    7860
aacatcctgg ggcacaagct ggagtacaac tacaacagcc acaacgtcta tatcatggcc    7920
gacaagcaga gaacggcat caaggtgaac ttcaagatcc gccacaacat cgaggacggc      7980
agcgtgcagc tcgccgacca ctaccagcag aacaccccca tcggcgacgg ccccgtgctg    8040
ctgcccgaca ccactacct gagctaccag tccgccctga gcaaagaccc caacgagaag     8100
cgcgatcaca tggtcctgct ggagttcgtg accgccgccg ggatcactct cggcatggac    8160
gagctgtaca agtaataatc tagagggccg catcatgtaa ttagttatgt cacgcttaca    8220
ttcacgccct ccccccacat ccgctctaac cgaaaaggaa ggagttagac aacctgaagt    8280
ctaggtccct atttattttt ttatagttat gttagtatta agaacgttat ttatatttca    8340 aattttctt tttttctgt acagacgcgt gtacgcatgt aacattatac tgaaaacctt      8400
gcttgagaag gttttgggac gctcgaaggc tttaatttgc ggccctgcat taatgaatcg    8460
gccaacgcgc ggggagaggc ggtttgcgta ttgggcgctc ttccgcttcc tcgctcactg    8520
actcgctgcg ctcggtcgtt cggctgcggc gagcggtatc agctcactca aaggcggtaa    8580
tacggttatc cacagaatca ggggataacg caggaaagaa catgtgagca aaaggccagc    8640
aaaagcccag gaaccgtaaa aaggccgcgt tgctggcgtt tttccatagg ctccgccccc    8700
ctgacgagca tcacaaaaat cgacgctcaa gtcagaggtg gcgaaacccg acaggactat    8760
```

```
aaagatacca ggcgtttccc cctggaagct ccctcgtgcg ctctcctgtt ccgaccctgc    8820
cgcttaccgg atacctgtcc gcctttctcc cttcgggaag cgtggcgctt tctcatagct    8880
cacgctgtag gtatctcagt tcggtgtagg tcgttcgctc caagctgggc tgtgtgcacg    8940
aaccccccgt tcagcccgac cgctgcgcct tatccggtaa ctatcgtctt gagtccaacc    9000
cggtaagaca cgacttatcg ccactggcag cagccactgg taacaggatt agcagagcga    9060
ggtatgtagg cggtgctaca gagttcttga agtggtggcc taactacggc tacactagaa    9120
ggacagtatt tggtatctgc gctctgctga agccagttac cttcggaaaa agagttggta    9180
gctcttgatc cggcaaacaa accaccgctg gtagcggtgg ttttttttgtt tgcaagcagc    9240 agattacgcg cagaaaaaaa ggatctcaag aagatccttt gatcttttct acggggtctg    9300
acgctcagtg gaacgaaaac tcacgttaag ggattttggt catgagatta tcaaaaagga    9360
tcttcaccta gatccttttta aattaaaaat gaagttttaa atcaatctaa agtatatatg    9420
agtaaacttg gtctgacagt taccaatgct taatcagtga ggcacctatc tcagcgatct    9480
gtctatttcg ttcatccata gttgcctgac tccccgtcgt gtagataact acgatacggg    9540
agcgcttacc atctggcccc agtgctgcaa tgataccgcg agacccacgc tcaccggctc    9600
cagatttatc agcaataaac cagccagccg gaagggccga gcgcagaagt ggtcctgcaa    9660
ctttatccgc ctccatccag tctattaatt gttgccggga agctagagta agtagttcgc    9720
cagttaatag tttgcgcaac gttgttggca ttgctacagg catcgtggtg tcactctcgt    9780
cgtttggtat ggcttcattc agctccggtt cccaacgatc aaggcgagtt acatgatccc    9840
ccatgttgtg caaaaaagcg gttagctcct tcggtcctcc gatcgttgtc agaagtaagt    9900
tggccgcagt gttatcactc atggttatgg cagcactgca taattctctt actgtcatgc    9960
catccgtaag atgcttttct gtgactggtg agtactcaac caagtcattc tgagaatagt   10020
gtatgcggcg accgagttgc tcttgcccgg cgtcaatacg ggataatagt gtatcacata   10080
gcagaacttt aaaagtgctc atcattggaa aacgttcttc ggggcgaaaa ctctcaagga   10140
tcttaccgct gttgagatcc agttcgatgt aacccactcg tgcacccaac tgatcttcag   10200
catcttttac tttcaccagc gtttctgggt gagcaaaaac aggaaggcaa aatgccgcaa   10260
aaaagggaat aagggcgaca cggaaatgtt gaatactcat actcttcctt tttcaatggg   10320
taataactga tataattaaa ttgaagctct aatttgtgag tttagtatac atgcatttac   10380
ttataataca gttttttagt tttgctggcc gcatcttctc aaatatgctt cccagcctgc   10440
ttttctgtaa cgttcaccct ctaccttagc atcccttccc tttgcaaata gtcctcttcc   10500
aacaataata atgtcagatc ctgtagagac cacatcatcc acggttctat actgttgacc   10560
caatgcgtct cccttgtcat ctaaacccac accgggtgtc ataatcaacc aatcgtaacc   10620
ttcatctctt ccacccatgt ctctttgagc aataaagccg ataacaaaat ctttgtcgct   10680
cttcgcaatg tcaacagtac ccttagtata ttctccagta gatagggagc ccttgcatga   10740
caattctgct aacatcaaaa ggcctctagg ttcctttgtt acttcttctg ccgcctgctt   10800
caaaccgcta acaatacctg ggcccaccac accgtgtgca ttcgtaatgt ctgcccattc   10860
tgctattctg tatacacccg cagagtactg caatttgact gtattaccaa tgtcagcaaa   10920
ttttctgtct tcgaagagta aaaaattgta cttggcggat aatgccttta gcggcttaac   10980
tgtgccctcc atggaaaaat cagtcaagat atccacatgt gttttagta aacaaatttt   11040 gggacctaat gcttcaacta actccagtaa ttccttggtg gtacgaacat ccaatgaagc   11100
acacaagttt gtttgctttt cgtgcatgat attaaatagc ttggcagcaa caggactagg   11160
```

```
atgagtagca gcacgttcct tatatgtagc tttcgacatg atttatcttc gtttcctgca    11220 ggttttgtt ctgtgcagtt gggttaagaa tactgggcaa tttcatgttt cttcaacact     11280
acatatgcgt atatatacca atctaagtct gtgctccttc cttcgttctt ccttctgttc    11340
ggagattacc gaatcaaaaa aatttcaaag aaaccgaaat caaaaaaaag aataaaaaaa    11400
aaatgatgaa ttgaattgaa aagctagctt atcgatgata agctgtcaaa gatgagaatt    11460
aattccacgg actatagact atactagata ctccgtctac tgtacgatac acttccgctc    11520
aggtccttgt cctttaacga ggccttacca ctcttttgtt actctattga tccagctcag    11580
caaaggcagt gtgatctaag attctatctt cgcgatgtag taaaactagc tagaccgaga    11640
aagagactag aaatgcaaaa ggcacttcta caatggctgc catcattatt atccgatgtg    11700
acgctgcagc ttctcaatga tattcgaata cgctttgagg agatacagcc taatatccga    11760
caaactgttt tacagattta cgatcgtact tgttacccat cattgaattt tgaacatccg    11820
aacctgggag ttttccctga aacagatagt atatttgaac ctgtataata atatatagtc    11880
tagcgcttta cggaagacaa tgtatgtatt tcggttcctg agaaactat tgcatctatt      11940 gcataggtaa tcttgcacgt cgcatccccg gttcattttc tgcgtttcca tcttgcactt    12000
caatagcata tctttgttaa cgaagcatct gtgcttcatt ttgtagaaca aaaatgcaac    12060
gcgagagcgc taattttca aacaaagaat ctgagctgca ttttacaga acagaaatgc       12120 aacgcgaaag cgctatttta ccaacgaaga atctgtgctt cattttgta aacaaaaat       12180 gcaacgcgac gagagcgcta attttcaaa caaagaatct gagctgcatt tttacagaac     12240
agaaatgcaa cgcgagagcg ctattttacc aacaaagaat ctatacttct tttttgttct    12300
acaaaaatgc atcccgagag cgctattttt ctaacaaagc atcttagatt acttttttc      12360 tcctttgtgc gctctataat gcagtctctt gataactttt tgcactgtag gtccgttaag    12420
gttagaagaa ggctactttg gtgtctattt tctcttccat aaaaaaagcc tgactccact    12480
tcccgcgttt actgattact agcgaagctg cgggtgcatt ttttcaagat aaaggcatcc    12540
ccgattatat tctataccga tgtggattgc gcatactttg tgaacagaaa gtgatagcgt    12600
tgatgattct tcattggtca gaaaattatg aacggtttct tctattttgt ctctatatac    12660
tacgtatagg aaatgtttac attttcgtat tgttttcgat tcactctatg aatagttctt    12720
actacaattt ttttgtctaa agagtaatac tagagataaa cataaaaaat gtagaggtcg    12780
agtttagatg caagttcaag gagcgaaagg tggatgggta ggttatatag ggatatagca    12840
cagagatata tagcaaagag atactttga gcaatgtttg tggaagcggt attcgcaatg      12900
ggaagctcca ccccggttga taatcagaaa agccccaaaa acaggaagat tgtataagca    12960
aatatttaaa ttgtaaacgt taatattttg ttaaaattcg cgttaaattt ttgttaaatc    13020
agctcatttt ttaacgaata gcccgaaatc ggcaaaatcc cttataaatc aaaagaatag    13080
accgagatag ggttgagtgt tgttccagtt tccaacaaga gtccactatt aaagaacgtg    13140
gactccaacg tcaaagggcg aaaaagggtc tatcagggcg atggcccact acgtgaacca    13200
tcaccctaat caagtttttt ggggtcgagg tgccgtaaag cagtaaatcg aagggtaaa     13260 cggatgcccc catttagagc ttgacgggga agccggcga acgtggcgag aaaggaaggg     13320
aagaaagcga aaggagcggg ggctagggcg gtgggaagtg tagggtcac gctgggcgta     13380 accaccacac ccgccgcgct taatggggcg ctacagggcg cgtggggatg atccactagt    13440
```

<210> SEQ ID NO 11

<211> LENGTH: 10123
<212> TYPE: DNA
<213> ORGANISM: Artificial sequence
<220> FEATURE:
<223> OTHER INFORMATION: Synthetic construct

<400> SEQUENCE: 11

| | | | | | |
|---|---|---|---|---|---|
| ggggaattgt | gagcggataa | caattcccct | ctagaaataa | ttttgtttaa | ctttaagaag | 60 |
| gagatatacc | atggtgttta | tcgtcaatct | tttctcctgc | accttatctg | aaaccacggt | 120 |
| tagctcaata | aaatctgaag | ctacggttag | ctcaacattt | actgccgtca | cggccctgca | 180 |
| attggtggct | gagggtaagt | tgcagtcggc | gaagggtttc | ggtggtggta | cgattcacta | 240 |
| cccaaccctc | gcggccgaag | caccctggtg | gacgccgggc | caaggccatg | gttacgaggc | 300 |
| gatcacctac | ggctggctgg | tcggcgaact | gctgcgccgc | gccgatgggc | gtgggcctgg | 360 |
| tctgttaggc | gctattgccg | tggttcctgg | ttacgtttct | tacgagaact | ctatcaagtg | 420 |
| gtggggaccg | cgtctggctt | cttggggctt | tgtcgttgca | cggccgttgg | gcctggactt | 480 |
| tcatgtgggc | ctggcggatg | aagagtttta | tcgtgttgcc | catatagcgc | gcagcaaagc | 540 |
| caatgcagca | ctagataaca | ttgctgatga | caccgtcggc | agtatagatc | ctaagcggtt | 600 |
| gggcgctatt | ggctggtcag | gtggcggcgg | cgcgcttaaa | ctggcaacgg | agcgcagcac | 660 |
| agtacgagcc | attttgacca | gtactaataa | acctgaatgg | cgacgcttcg | ataaattctt | 720 |
| atgtgcctgc | gaggatgacc | ggattgctga | gactaagaaa | tatgccaacg | cgttttataa | 780 |
| aaatgccgac | atgctcgaag | agttgacccg | tgaacacagt | atcgggccgg | ataaaacatt | 840 |
| attgacacaa | actcggtttg | gcttggggtg | cttggatcaa | ccgcaagcag | gggttaaaat | 900 |
| tcattttgaa | gagtaccttg | atcaaaccca | tggatttatc | aatttgacgc | agtttcaca | 960 |
| taaggcgaga | gcaaatctga | ttcagatgcc | taatgccaca | ttcggccttg | cccgcgtgc | 1020 |
| ttttgggcat | cctggtgcag | gtggatcggt | aggttttgcc | gaccccgaac | acgatgtagc | 1080 |
| gtttggtttc | gtgactaata | cattgggggcc | ttatgtagtt | gagtttaaaa | gccgtcatcc | 1140 |
| ctcattttat | gcatataaag | atggattggt | gctgactgga | aatgacgtcg | actatgtgac | 1200 |
| tgattactat | gcaacaaagc | atgctgtaca | tttagatgat | ccacgtgcac | agaagttggt | 1260 |
| cggaatattg | gccggttgtc | tgtaaggatc | cgaattcgag | ctcggcgcgc | ctgcaggtcg | 1320 |
| acaagcttgc | ggccgcataa | tgcttaagtc | gaacagaaag | taatcgtatt | gtacacggcc | 1380 |
| gcataatcga | aattaatacg | actcactata | ggggaattgt | gagcggataa | caattcccca | 1440 |
| tcttagtata | ttagttaagt | ataagaagga | gatatacata | tggagactgt | tcgtccaggt | 1500 |
| tgttttcgtg | ctgttgtttc | tgttccactg | ggtcgtctga | cttactcttt | cctggtggac | 1560 |
| ggtcagccga | agtacaaccc | ggactgtccg | actctggtta | acgaagctgg | cgtgcgtgtg | 1620 |
| aacgtacgcc | acggtggttc | tgacggtgat | tgcgacggtg | aagctgacga | agaatggggt | 1680 |
| aaaggtcgtc | caagccgtgc | tcgtcgcgtg | ctgagccagg | tttctggcct | ggacctgtac | 1740 |
| tctcagcact | ccaccagcga | catcgtttct | atgctggtgt | tccgtttctt | ctacctggct | 1800 |
| atgattccag | ctggtgccta | ctacttcttc | tggctgagcg | ttcgtggtgg | taatcgccag | 1860 |
| gctccagttt | gctgggtggt | gttcgttatg | agcgaaatcc | tgtctttcgt | tagcgcgctg | 1920 |
| atttccctgt | ttggcatgtg | gaagccgatc | aaacgtcgtt | ggcgctctct | ggacgctctg | 1980 |
| cgtccagctc | tgccagttgc | agattggcca | actgtagacg | tgatcatttg | ccactacaaa | 2040 |
| gaggacaccg | aacagctgcg | tcagactatt | cgtgcagcga | tgaaactgga | ttcccagcc | 2100 |
| catctgctgc | acattctgat | tgccgacgat | ggcttcttcc | caacctccaa | gatggtagag | 2160 |

```
cgttctgata ttggtctggc tctgtaccag acctgtgttg aggaagcggg ttatgatccg   2220
ctgctggaag aaaccatgaa tgaacgtggt ctggttgaac actatactgt taaggcaggt   2280
gacgacctgc cgcgtcatga ttgcgcggtt gaagctcacc agttcgagtt tggtccgtat   2340
ggtgcggaca tgtacggtcc aggtgccctg ccacgtctgt ccctggttgc tcgtgtgaag   2400
ccggctgacg ctcacaacaa ggcaggcaac atcaacaacg tactgtccaa ctctaacgca   2460
gaaggtaaga ttgttctgtt cctggatgct gacatgaagc cggtagaatc ttacctgctg   2520
cgtgttctgc cactgatgct ggaagagcag cgttccgata gcctgcagag ccaactgatc   2580
caggcagagg acccagagct gggtgctggt acttctaaga gctggcaaat caaccgtgac   2640
attggcttcg ttggctgccc acaacgcttc gcgaacgtat ccggtgacca tccggattac   2700
tgtgctcacc gtaacgcgat ctactacgac ggtatctgca ctggtcgtga tggtttcggt   2760
atgaccgact tcgttggcac taacgcgtgt tggcgtcgcg aagttctgaa cgagatcggt   2820
ggcttcgttt atggtagcgt gactgaagac accctgacta gcaacgaagt tcatcgccgt   2880
ggctacatta gccgctacgc tgacgaagac ctgtgctggg gtgaagcacc agttaccgtt   2940
gcagcagctc tgctgcagcg tcaacgttgg gctaaaggtg ccatcatgaa cggtatgcgt   3000
atcttcaaag gtgctgctaa agaacgcaaa gaaatgctgc tgagccgtga gaaaccgtct   3060
gaactgtctg agttctacgc atatcgtcgt cagcagcgta aaccaaacaa cactttcgtt   3120
tctaccatgt tctggctgga ttctactctg tacccactgc tgggttgggg tgctttcggt   3180
tacgtgttct gtgctatctt ccacctgatc accgctcagg caccgatctc tccgacctct   3240
actcagagcc tggctggtgc gtttgtgacc tactatctga ttcgttacgg tgcattcttc   3300
tctgccttct atgaagtgaa catgaccgac gttctgcgct tcagcagtg ttggttctct   3360 tactccttcg cccacactgt gggtgtatgg gatgctctgt ttggtggtgc caagtttggc   3420
tgggttgcta acactggcca acgtcatcgc cgtagctggc tggaatggtt caacatcctg   3480
actctgggtg ctctgctgtc cggcattgtg tggcgtctgt tcgcgttcat tgttatcgaa   3540
gaagcgtgtt ctccgtacga gaacttcggt gctgttgcat tcggcggtta cgtagcgtgg   3600
atgatggctc cagttgctct ggttagcctg aacgaacgcc tgtcttccgc tgacgaatcc   3660
gagcgtgaag gtaaaccgat gccagtgccg actccgatca tcgctgctgc cctgactatc   3720
ctgggtgttg tgttcctgtc tggttgggca acgctcgtt gtggtatcga agctcgcggt   3780
taaggtacca gaataatttt tgtttaactt taagaaggag actcgagatg gcgaagtttg   3840
gtagccgtaa taagtctccg aagtggatct ctaacggctg ctgcttcctg ctgggtgcct   3900
ttactgctct gctgctgctg tggggtctgt gctcctttat tatcccgatt ccgaacaccg   3960
atccgaagct gaactctgta gcgacctctc tgcgttctct gaacttcccg aagaacccag   4020
cagctaccct gccaccgaac ctgcagcatg atccaccgga tactactttc tacgacgatc   4080
cggaaacctc ttatactatg gataaaccga tgaagaactg ggacgagaaa cgtaaggaat   4140
ggctgctgca tcacccgtcc ttcggcgcag ctgctcgtga caagatcctg ctggtaaccg   4200
gttcccagcc gaaacgctgt cacaacccga ttggtgatca cctgctgctg cgttttcttta   4260 agaacaaagt ggattactgc cgtctgcata attacgatat catctataac aacgcactgc   4320
tgcacccgaa aatgaactcc tattgggcta agtacccagt gatccgtgct gcaatgatgg   4380
ctcatccgga agttgaatgg gtgtggtggg ttgactctga cgctgtattc actgacatgg   4440
agtttaaact gccactgaaa cgctataaga accacaatct ggtggtgcat ggttgggaag   4500
```

-continued

```
gtctggtacg tctgaaccac tcctggactg gtctgaacgc aggtgtattc ctgatccgta    4560
attgccaatg gagcctggag ttcatggatg tatgggttag catgggtcca caaactccag    4620
aatacgagaa atggggtgag cgtctgcgcg aaaccttcaa agataaagtt ctgccagact    4680
ctgatgacca gactgcactg gcatacctga tcgcaaccga taacaaagac acctggcgtg    4740
agaaaatctt cctggaaagc gagtactact tcgaaggcta ttggctggaa atcgtaaaga    4800
cttacgagaa catctccgaa cgttacgatg aagttgaacg caaagtagaa ggtctgcgtc    4860
gtcgccacgc tgagaaggtt agcgagaaat acggtgcaat gcgtgaagaa tacctgaaag    4920
ataacaaacg tcgtccgttc atcacccatt tcactggttg ccagccgtgc aacggtcacc    4980
ataacccagc atacaatgcg aacgactgtt ggaatggtat ggaacgtgca ctgaactttg    5040
cagataacca gatcctgcgt acctacggtt accatcgtca gaatctgctg gacaagtccg    5100
tttctccact gccgttcggt tatccagcag cttaacctag gctgctgcca ccgctgagca    5160
ataactagca taaccccttg gggcctctaa acgggtcttg aggggttttt tgctgaaagg    5220
aggaactata tccggattgg cgaatgggac gcgccctgta gcggcgcatt aagcgcggcg    5280
ggtgtggtgg ttacgcgcag cgtgaccgct acacttgcca gcgccctagc gcccgctcct    5340
ttcgctttct tcccttcctt tctcgccacg ttcgccggct ttccccgtca gctctaaat    5400 cgggggctcc ctttagggtt ccgatttagt gctttacggc acctcgaccc caaaaaactt    5460
gattagggtg atggttcacg tagtgggcca tcgccctgat agacggtttt tcgccctttg    5520
acgttggagt ccacgttctt taatagtgga ctcttgttcc aaactggaac aacactcaac    5580
cctatctcgg tctattcttt tgatttataa gggattttgc cgatttcggc ctattggtta    5640
aaaaatgagc tgatttaaca aaaatttaac gcgaatttta acaaaatatt aacgtttaca    5700
atttctggcg gcacgatggc atgagattat caaaaaggat cttcacctag atccttttaa    5760
attaaaaatg aagttttaaa tcaatctaaa gtatatatga gtaaacttgg tctgacagtt    5820
accaatgctt aatcagtgag gcacctatct cagcgatctg tctatttcgt tcatccatag    5880
ttgcctgact ccccgtcgtg tagataacta cgatacggga gggcttacca tctggcccca    5940
gtgctgcaat gataccgcga gacccacgct caccggctcc agatttatca gcaataaacc    6000
agccagccgg aagggccgag cgcagaagtg gtcctgcaac tttatccgcc tccatccagt    6060
ctattaattg ttgccgggaa gctagagtaa gtagttcgcc agttaatagt ttgcgcaacg    6120
ttgttgccat tgctacaggc atcgtggtgt cacgctcgtc gtttggtatg gcttcattca    6180
gctccggttc ccaacgatca aggcgagtta catgatcccc catgttgtgc aaaaaagcgg    6240
ttagctcctt cggtcctccg atcgttgtca gaagtaagtt ggccgcagtg ttatcactca    6300
tggttatggc agcactgcat aattctctta ctgtcatgcc atccgtaaga tgcttttctg    6360
tgactggtga gtactcaacc aagtcattct gagaatagtg tatgcggcga ccgagttgct    6420
cttgcccggc gtcaatacgg gataataccg cgccacatag cagaacttta aaagtgctca    6480
tcattggaaa acgttcttcg gggcgaaaac tctcaaggat cttaccgctg ttgagatcca    6540
gttcgatgta acccactcgt gcacccaact gatcttcagc atcttttact ttcaccagcg    6600
tttctgggtg agcaaaaaca ggaaggcaaa atgccgcaaa aaagggaata agggcgacac    6660
ggaaatgttg aatactcata ctcttccttt ttcaatcatg attgaagcat ttatcagggt    6720
tattgtctca tgagcggata catatttgaa tgtatttaga aaataaaca aataggtcat    6780 gaccaaaatc ccttaacgtg agttttcgtt ccactgagcg tcagacccog tagaaaagat    6840 caaaggatct tcttgagatc cttttttttct gcgcgtaatc tgctgcttgc aaacaaaaaa    6900
```

```
accaccgcta ccagcggtgg tttgtttgcc ggatcaagag ctaccaactc tttttccgaa    6960
ggtaactggc ttcagcagag cgcagatacc aaatactgtc cttctagtgt agccgtagtt    7020
aggccaccac ttcaagaact ctgtagcacc gcctacatac ctcgctctgc taatcctgtt    7080
accagtggct gctgccagtg gcgataagtc gtgtcttacc gggttggact caagacgata    7140
gttaccggat aaggcgcagc ggtcgggctg aacgggggt tcgtgcacac agcccagctt     7200
ggagcgaacg acctacaccg aactgagata cctacagcgt gagctatgag aaagcgccac    7260
gcttcccgaa gggagaaagg cggacaggta tccggtaagc ggcagggtcg aacaggaga    7320 gcgcacgagg gagcttccag ggggaaacgc ctggtatctt tatagtcctg tcgggtttcg    7380
ccacctctga cttgagcgtc gattttgtg atgctcgtca ggggggcgga gcctatggaa     7440
aaacgccagc aacgcggcct ttttacggtt cctggccttt tgctggcctt ttgctcacat    7500
gttctttcct gcgttatccc ctgattctgt ggataaccgt attaccgcct tgagtgagc    7560 tgataccgct cgccgcagcc gaacgaccga gcgcagcgag tcagtgagcg aggaagcgga    7620
agagcgcctg atgcggtatt ttctccttac gcatctgtgc ggtatttcac accgcatata    7680
tggtgcactc tcagtacaat ctgctctgat gccgcatagt taagccagta tacactccgc    7740
tatcgctacg tgactgggtc atggctgcgc cccgacaccc gccaacaccc gctgacgcgc    7800
cctgacgggc ttgtctgctc ccggcatccg cttacagaca agctgtgacc gtctccggga    7860
gctgcatgtg tcagaggttt tcaccgtcat caccgaaacg cgcgaggcag ctgcggtaaa    7920
gctcatcagc gtggtcgtga agcgattcac agatgtctgc ctgttcatcc gcgtccagct    7980
cgttgagttt ctccagaagc gttaatgtct ggcttctgat aaagcgggcc atgttaaggg    8040
cggttttttc ctgtttggtc actgatgcct ccgtgtaagg gggatttctg ttcatggggg    8100
taatgatacc gatgaaacga gagaggatgc tcacgatacg ggttactgat gatgaacatg    8160
cccggttact ggaacgttgt gagggtaaac aactggcggt atggatgcgg cgggaccaga    8220
gaaaaatcac tcagggtcaa tgccagcgct tcgttaatac agatgtaggt gttccacagg    8280
gtagccagca gcatcctgcg atgcagatcc ggaacataat ggtgcagggc gctgacttcc    8340
gcgtttccag actttacgaa acacggaaac cgaagaccat tcatgttgtt gctcaggtcg    8400
cagacgtttt gcagcagcag tcgcttcacg ttcgctcgcg tatcggtgat tcattctgct    8460
aaccagtaag gcaaccccgc cagcctagcc gggtcctcaa cgacaggagc acgatcatgc    8520
tagtcatgcc ccgcgcccac cggaaggagc tgactgggtt gaaggctctc aagggcatcg    8580
gtcgagatcc ggtgcctaa tgagtgagct aacttacatt aattgcgttg cgctcactgc     8640
ccgctttcca gtcgggaaac ctgtcgtgcc agctgcatta atgaatcggc caacgcgcgg    8700
ggagaggcgg tttgcgtatt gggcgccagg gtggtttttc ttttcaccag tgagacgggc    8760
aacagctgat tgcccttcac cgcctggccc tgagagagtt gcagcaagcg gtccacgctg    8820
gtttgcccca gcaggcgaaa atcctgtttg atggtggtta acggcgggat ataacatgag    8880
ctgtcttcgg tatcgtcgta tcccactacc gagatgtccg caccaacgcg cagcccggac    8940
tcggtaatgg cgcgcattgc gcccagcgcc atctgatcgt tggcaaccag catcgcagtg    9000
ggaacgatgc cctcattcag catttgcatg gtttgttgaa aaccggacat ggcactccag    9060
tcgccttccc gttccgctat cggctgaatt tgattgcgag tgagatattt atgccagcca    9120
gccagacgca gacgcgccga gacagaactt aatgggcccg ctaacagcgc gatttgctgg    9180
tgacccaatg cgaccagatg ctccacgccc agtcgcgtac cgtcttcatg ggagaaaata    9240
```

```
atactgttga tgggtgtctg gtcagagaca tcaagaaata acgccggaac attagtgcag    9300
gcagcttcca cagcaatggc atcctggtca tccagcggat agttaatgat cagcccactg    9360
acgcgttgcg cgagaagatt gtgcaccgcc gctttacagg cttcgacgcc gcttcgttct    9420
accatcgaca ccaccacgct ggcacccagt tgatcggcgc gagatttaat cgccgcgaca    9480
atttgcgacg gcgcgtgcag ggccagactg gaggtggcaa cgccaatcag caacgactgt    9540
ttgcccgcca gttgttgtgc cacgcggttg ggaatgtaat tcagctccgc catcgccgct    9600 tccactttt cccgcgtttt cgcagaaacg tggctggcct ggttcaccac gcgggaaacg    9660
gtctgataag agacaccggc atactctgcg acatcgtata acgttactgg tttcacattc    9720 accacctga attgactctc ttccgggcgc tatcatgcca taccgcgaaa ggttttgcgc    9780
cattcgatgg tgtccgggat ctcgacgctc tcccttatgc gactcctgca ttaggaagca    9840
gcccagtagt aggttgaggc cgttgagcac cgccgccgca aggaatggtg catgcaagga    9900
gatggcgccc aacagtcccc cggccacggg gcctgccacc atacccacgc cgaaacaagc    9960
gctcatgagc ccgaagtggc gagcccgatc ttccccatcg gtgatgtcgg cgatataggc    10020
gccagcaacc gcacctgtgg cgccggtgat gccggccacg atgcgtccgg cgtagaggat    10080
cgagatcgat ctcgatcccg cgaaattaat acgactcact ata                      10123
```

DNA CONSTRUCTS AND BIOLOGICAL DEVICES FOR PRODUCING CARBO SUGARS

CROSS REFERENCE TO RELATED APPLICATIONS

This application claims priority upon U.S. provisional application Ser. No. 62/664,991 filed on May 1, 2018. This application is hereby incorporated by reference in its entirety.

BACKGROUND

Petroleum is a complex mixture of organic compounds that includes alkanes, cycloalkanes, and aromatic compounds, some of which may additionally contain heteroatoms such as nitrogen, oxygen, and sulfur, as well as trace metals. Petroleum is a raw material for many products, including solvents, fertilizers, plastics, and pharmaceuticals; however, the primary use for petroleum is as an energy source. Petroleum accounts for as much as one third of the world's energy use, with demand increasing yearly, particularly in developing countries. As easily accessible supplies of petroleum are exhausted, oil companies are forced to develop and rely upon alternative methods for crude oil extraction.

One method for releasing petroleum for extraction that has become increasingly important is hydraulic fracturing. This technique involves the use of pressurized fluids to propagate cracks in rock layers in hydrocarbon-bearing zones. These cracks become channels through which oil can flow to a wellbore or drill hole from which it can then be recovered. In hydraulic fracturing, the pressurized fluids may include proppants such as sand or other particulate matter; the proppants serve to keep the fractures open to allow for the flow of crude oil. One problem associated with extracting petroleum from various soil environments is the contamination of ground water. Thus, it would be desirable to treat the ground water with an additive that effectively removes the oil from the water.

SUMMARY

Described herein are biological devices and methods for using the same to produce carbo sugars. The biological devices include microbial cells transformed with a DNA construct containing genes for producing a cellulose synthase and galactomannan galactosyltransferase. In some instances, the biological devices also include a gene for lipase. Methods for altering the viscosity of petroleum oil using the carbo sugars are also described herein. Finally, methods for degreasing or decontaminating water mixed with petroleum oil or other fatty substances or a surface coated with petroleum oil or other fatty substances using the carbo sugars are described herein.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 2 is a schematic of a constructed pYES2 plasmid showing the direction, placement, and size of genetic parts used in one aspect of the DNA device.

FIG. 14A shows the initial appearance of the samples. FIGS. 14B, 14C, and 14D show the samples at times 5 minutes, 10 minutes, and 40 minutes after the initial treatment, respectively. As can be seen, the biological devices described herein display better decontamination of the glass Petri dishes than either of the controls.

FIGS. 15A and 15B show degreasing of water contaminated with petroleum oil at the start of treatment (time 0 minutes, FIG. 15A) and after less than one minute (FIG. 15B). FIG. 15A is water contaminated with petroleum and treated with a 0.5% concentration of carbo sugar extract. FIG. 15B displays water contaminated with petroleum and treated with a non-transformed yeast extract control. As can be seen from the images, the carbo sugar extract from the biological devices effects separation of oil from water nearly instantaneously.

FIG. 18A is a control sample and FIG. 18B uses carbo sugar.

DETAILED DESCRIPTION

Figure 1:
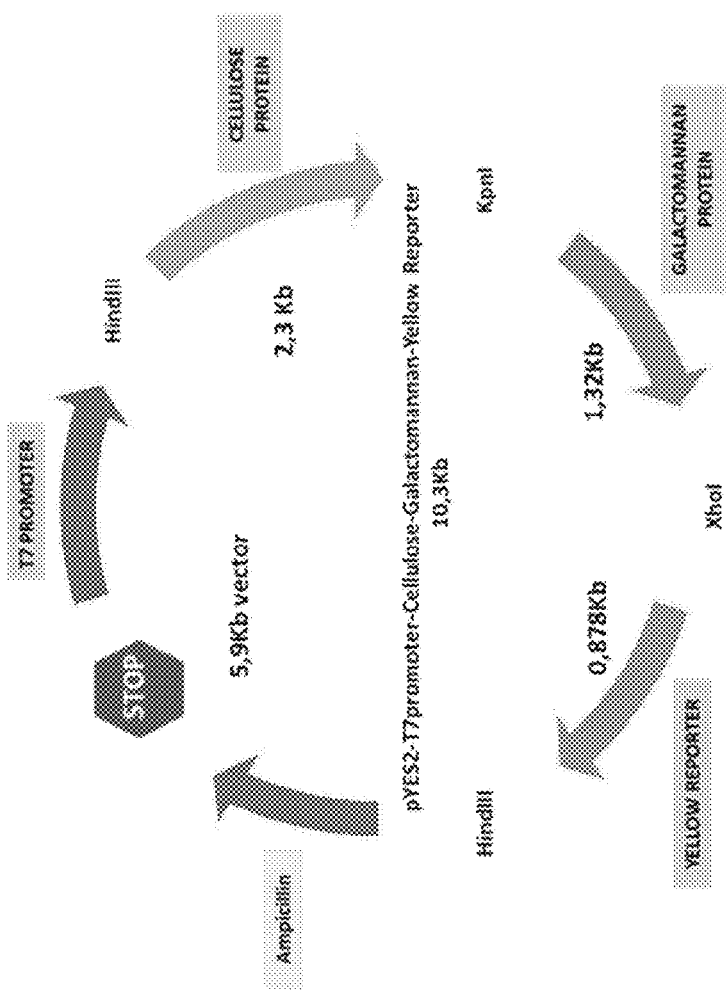
FIG. 1 is a schematic of a constructed pYES2 plasmid showing the direction, placement, and size of genetic parts used in one aspect of the DNA device.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a surfactant" includes mixtures of two or more such surfactants, and the like.

"Optional" or "optionally" means that the subsequently described event or circumstance can or cannot occur, and that the description includes instances where the event or circumstance occurs and instances where it does not. For example, the phrase "optionally includes a reporter protein" means that the reporter protein may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that are possible are specifically contemplated unless specifically indicated to the contrary. For example, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein is a process for producing carbo sugars using microbial cells that includes (a) making a DNA construct containing genes for producing a cellulose synthase protein and galactomannan galactosyltransferase, (b) introducing the DNA construct into host microbial cells via transformation or transfection, and (c) culturing the microbial host cells to produce carbo sugars. Methods for altering the viscosity of petroleum oil using the carbo sugars are also contemplated herein.

I. DNA Constructs

DNA constructs are provided herein for the production of carbo sugars. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed according to published algorithms (see Zuker, M. *Science* 244:48-52, 1989; Jaeger et al. *Proc. Natl. Acad. Sci. USA* 86:7706-7710, 1989; Jaeger et al. *Methods Enzymol.* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, the microorganisms are fungi or bacteria. In one aspect, the fungi are yeasts such as, for example, *Saccharomyces cerevisiae*. In another aspect, the bacteria are *Escherichia coli*. In one aspect, the DNA construct is incorporated as part of a vector for transfection into microbial cells. In a further aspect, the vector is a plasmid, a phagemid, a cosmid, a yeast artificial chromosome, a bacterial artificial chromosome, a virus, a phage, or a transposon.

Vectors capable of high levels of expression of recombinant genes and proteins are well known in the art. Vectors useful for the transformation of a variety of host cells are common and commercially available and include, for example, pWLneo, pSV2cat, pOG44, pXT1, pSG, pSVK3, pBSK, pBR322, pYES, pYES2, pBSKII, pUC, pUC19, and pETDuet-1. The skilled practitioner will be able to choose a plasmid based on such factors as a) the amount of nucleic acid (i.e. number of genes and other elements) to be inserted, b) the host organism, c) culture conditions for the host organism, and other related factors.

In one aspect, provided herein is a DNA construct comprising the following genetic components:
a. a gene that expresses cellulose synthase; and
b. a gene that expresses galactomannan galactosyltransferase.

In another aspect, provided herein is a DNA construct comprising the following genetic components:
a. a gene that expresses cellulose synthase;
b. a gene that expresses galactomannan galactosyltransferase; and
c. a gene that expresses lipase.

Each component of the DNA construct is described in detail below.

In one aspect, the nucleic acids (e.g., genes that expresses cellulose synthase or galactomannan galactosyltransferase) used in the DNA constructs described herein can be amplified using polymerase chain reaction (PCR) prior to being ligated into a plasmid or other vector. Typically, PCR-amplification techniques make use of primers, or short, chemically-synthesized oligonucleotides are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the gene that expresses cellulose synthase is isolated from plants. In a different aspect, the gene that expresses cellulose synthase is isolated from algae. In one aspect, the algal species is a red algal species such as, for example, *Pyropia yezoensis* (also known as *Porphyra yezoensis*) or *Griffithsia monilis*. In a further aspect, the gene that expresses cellulose synthase has SEQ ID NO. 1 or at least 70% homology thereof, at least 75% homology thereof, at least 80% homology thereof, at least 85% homology thereof, at least 90% homology thereof, or at least 95% homology thereof. In a further aspect, the cellulose synthase is able to use mannose as a substrate instead of or in addition to glucose.

Other sequences expressing cellulose synthase or related or homologous genes can be identified in a database such as, for example, GenBank. In one aspect, sequences useful herein include those with the GI numbers listed in Table 1:

TABLE 1

Cellulose Synthase Genes

| Source Organism | Sequence Description | GI Number |
|---|---|---|
| *Porphyra vezoensis* | cellulose synthase | EU279853.1 |
| *Porphyra vezoensis* | cellulose synthase | EU279861.1 |
| *Porphyra vezoensis* | cellulose synthase pseudogene | EU279857.1 |
| *Porphyra vezoensis* | cellulose synthase pseudogene | EU279858.1 |
| *Porphyra vezoensis* | cellulose synthase pseudogene | EU279854.1 |

TABLE 1-continued

Cellulose Synthase Genes

| Source Organism | Sequence Description | GI Number |
|---|---|---|
| *Porphyra vezoensis* | cellulose synthase pseudogene | EU279855.1 |
| *Chondrus crispus* | cellulose synthase family | XM_005715532.1 |
| *Porphyra vezoensis* | cellulose synthase pseudogene | EU279859.1 |
| *Porphyra vezoensis* | cellulose synthase pseudogene | EU279856.1 |
| *Porphyra vezoensis* | cellulose synthase pseudogene | EU279860.1 |
| *Gelidiella liqulata* | cellulose synthase catalytic subunit A | KT920245.1 |
| *Gelidiella acerosa* | cellulose synthase catalytic subunit A | KT920242.1 |
| *Parviphycus albertanoae* | cellulose synthase catalytic subunit A | KT920246.1 |
| *Parviphycus felicinii* | cellulose synthase catalytic subunit A | KT920247.1 |
| *Gelidiella incrassata* | cellulose synthase catalytic subunit A | KT920244.1 |
| *Pterocladiella melanoidea* | cellulose synthase catalytic subunit A | KT920254.1 |
| *Griffithsia monilis* | cellulose synthase A | GU563823.1 |
| *Gelidiella fanii* | cellulose synthase catalytic subunit A | KT920243.1 |
| *Pterocladia rectangularis* | cellulose synthase catalytic subunit A | KT920196.1 |
| *Ptilophora mediterranea* | cellulose synthase catalytic subunit A | KT920238.1 |
| *Gelidium pacificum* | cellulose synthase catalytic subunit A | KT920227.1 |
| *Gelidium microdon* | cellulose synthase catalytic subunit A | KT920223.1 |
| *Gelidium johnstonii* | cellulose synthase catalytic subunit A | KT920222.1 |
| *Pterocladella bartletti* | cellulose synthase catalytic subunit A | KT920250.1 |
| *Pterocladia lucida* | cellulose synthase catalytic subunit A | KT920248.1 |
| *Gelidium declerckii* | cellulose synthase catalytic subunit A | KT920214.1 |
| *Ptilophora pterocladioides* | cellulose synthase catalytic subunit A | KT920240.1 |
| *Pterocladia lucida* | cellulose synthase catalytic subunit A | KT920249.1 |
| *Gelidium madagascariense* | cellulose synthase catalytic subunit A | KT920195.1 |
| *Gelidium sp.* GHB-2012 | cellulose synthase catalytic subunit A | KT920237.1 |
| *Gelidium crinate* | cellulose synthase catalytic subunit A | KT920212.1 |
| *Ptilophora scalaramosa* | cellulose synthase catalytic subunit A | KT920241.1 |
| *Gelidium robustum* | cellulose synthase catalytic subunit A | KT920234.1 |
| *Gelidium purpurascens* | cellulose synthase catalytic subunit A | KT920231.1 |
| *Gelidium pusilium* | cellulose synthase catalytic subunit A | KT920232.1 |
| *Gelidium indonesianum* | cellulose synthase catalytic subunit A | KT920218.1 |
| *Callophyllis japonica* | cellulose synthase catalytic subunit A | KT920257.1 |
| *Gelidium nudifrons* | cellulose synthase catalytic subunit A | KT920225.1 |
| *Gelidium isabelae* | cellulose synthase catalytic subunit A | KT920219.1 |
| *Pterocladiella beachiae* | cellulose synthase catalytic subunit A | KT920251.1 |
| *Gelidium spinosum* | cellulose synthase catalytic subunit A | KT920235.1 |
| *Gelidium prostratum* | cellulose synthase catalytic subunit A | KT920229.1 |
| *Geladium minimum* | cellulose synthase catalytic subunit A | KT920224.1 |

TABLE 1-continued

Cellulose Synthase Genes

| Source Organism | Sequence Description | GI Number |
|---|---|---|
| Gelidium sp. SMB-2011a | cellulose synthase catalytic subunit A | KT920216.1 |
| Gelidium elegans | cellulose synthase catalytic subunit A | KT920215.1 |
| Gelidium coulteri | cellulose synthase catalytic subunit A | KT920211.1 |
| Gracilaria textorii | cellulose synthase catalytic subunit A | KT920258.1 |
| Gelidium corneum | cellulose synthase catalytic subunit A | KT920210.1 |
| Gelidium bernabei | cellulose synthase catalytic subunit A | KT920207.1 |
| Gelidium abbottiorum | cellulose synthase catalytic subunit A | KT920204.1 |
| Grateloupia asiatica | cellulose synthase catalytic subunit A | KT920259.1 |
| Ptilophora prolifera | cellulose synthase catalytic subunit A | KT920239.1 |
| Gelidium crispum | cellulose synthase catalytic subunit A | KT920213.1 |
| Chondrus crispus | cellulose synthase family | XM_005711895.1 |
| Gelidium rex | cellulose synthase catalytic subunit A | KT920233.1 |
| Gelidium pulchellum | cellulose synthase catalytic subunit A | KT920230.1 |
| Gelidium coreanum | cellulose synthase catalytic subunit A | KT920209.1 |
| Gelidium capense | cellulose synthase catalytic subunit A | KT920208.1 |
| Rhodymenia intricata | cellulose synthase catalytic subunit A | KT920260.1 |
| Gelidium asperum | cellulose synthase catalytic subunit A | KT920205.1 |
| Aphanta pachyrrhiza | cellulose synthase catalytic subunit A | KT920193.1 |
| Pterocladella nana | cellulose synthase catalytic subunit A | KT920255.1 |
| Gelidium ornamense | cellulose synthase catalytic subunit A | KT920226.1 |
| Gelidium hommersandii | cellulose synthase catalytic subunit A | KT920217.1 |
| Gelidium australe | cellulose synthase catalytic subunit A | KT920206.1 |
| Pterocladiella caerulescens | cellulose synthase catalytic subunit A | KT920252.1 |
| Gelidium jejuense | cellulose synthase catalytic subunit A | KT920221.1 |
| Gelidium japonicum | cellulose synthase catalytic subunit A | KT920220.1 |
| Acanthopeltis longiramulosa | cellulose synthase catalytic subunit A | KT920200.1 |
| Capreolia implexa | cellulose synthase catalytic subunit A | KT920201.1 |
| Acanthopeltis japonica | cellulose synthase catalytic subunit A | KT920199.1 |
| Acanthopeltis hirsuta | cellulose synthase catalytic subunit A | KT920198.1 |
| Acanthopeltis hirsuta | cellulose synthase catalytic subunit A | KT920197.1 |
| Gelidium vagum | cellulose synthase catalytic subunit A | KT920236.1 |
| Aphanta sp. GHB-2016 | cellulose synthase catalytic subunit A | KT920194.1 |
| Pterocladelia capillacea | cellulose synthase catalytic subunit A | KT920253.1 |
| Gelidium pristoides | cellulose synthase catalytic subunit A | KT920228.1 |
| Pterocladelia tenuis | cellulose synthase catalytic subunit A | KT920256.1 |
| Gelidium divaricatum | cellulose synthase catalytic subunit A | KT920202.1 |
| Aphanomyces astaci | hypothetical protein | XM_009832014.1 |
| Aphanomyces invadans | hypothetical protein | XM_008862896.1 |
| Acanthamoeba castellanii str. Neff | putative cellulose synthase | XM_004335119.1 |

TABLE 1-continued

Cellulose Synthase Genes

| Source Organism | Sequence Description | GI Number |
|---|---|---|
| Phytophthora sojae | hypothetical protein | XM_009526171.1 |
| Phytophthora parasitica | hypothetical protein | XM_008915779.1 |
| Aphanomyces invadans | hypothetical protein | XM_008862899.1 |
| Saprolegnia diclina | hypothetical protein | XM_008616683.1 |
| Phytophthora infestans | putative cellulose synthase catalytic subunit | XM_002897169.1 |
| Phytophthora sojae | cellulose synthase 1 | EF563997.1 |
| Phytophthora infestans | cellulose synthase 3 | EF563995.1 |
| Jatropha curcas | sucrose transport protein | XM_012212213.2 |
| Jatropah curcas | sucrose transport protein | XM_012212212.2 |
| Jatropha curcas | sucrose transport protein | XM_012212211.2 |
| Jatropha curcas | sucrose transport protein | XM_012212210.2 |
| Jatropha curcas | sucrose transport protein | NM_001319920.1 |
| Saprolegnia parasitica | hypothetical protein | XM_012347851.1 |
| Protopolystoma xenopodis | unidentified | LM730806.1 |
| Aphanomyces invadans | hypothetical protein | XM_008869048.1 |
| Uncultured bacterium A1Q1 | unidentified | JX649872.1 |
| Plasmopara viticola | cellulose synthase 1 | GQ258973.1 |
| Pyrus × bretschneideri | H2 finger protein ATL20-like | XM_009348167.2 |

In one aspect, the gene that expresses galactomannan galactosyltransferase is isolated from a plant. In one aspect, the galactomannan galactosyltransferase is able to catalyze the synthesis of bonds between an oligo- or poly-mannose backbone and pendant galactose moieties to produce carbo sugars. In a further aspect, the plant is *Oryza japonica*, *Medicago truncatula*, *Glycine max*, *Trigonella foenum-graecum*, *Lotus japonicus*, *Senna occidentalis*, *Cucumis sativus*, *Fragaria vesca*, or *Cyamopsis tetragonoloba*. In a further aspect, the galactomannan galactosyltransferase has SEQ ID NOs. 2-4 or at least 70% homology thereof. In a further aspect, the gene that expresses galactomannan galactosyltransferase has SEQ ID NO. 4 or at least 70% homology thereof, at least 75% homology thereof, at least 80% homology thereof, at least 85% homology thereof, at least 90% homology thereof, or at least 95% homology thereof.

Other sequences expressing galactomannan galactosyltransferase or related or homologous genes can be identified in a database such as, for example, GenBank. In one aspect, sequences useful herein include those with the GI numbers listed in Table 2:

TABLE 2

Galactomannan Galactosyltransferase Genes

| Source Organism | Sequence Description | GI Number |
|---|---|---|
| Cyamopsis tetragonoloba | galactomannan galactosyltransferase | AJ938067.1 |
| Glycine max | galactomannan galactosyltransferase 1-like | XM_003525821.3 |
| Medicago truncatula | unidentified | AC140720.21 |
| Medicago truncatula | galactosyl transferase | XM_003608493.2 |
| Lotus japonicus | galactomannan galactosyltransferase | AJ567668.1 |
| Lupinus angustifolius | galactomannan galactosyltransferase 1-like | XM_019567307.1 |

TABLE 2-continued

Galactomannan Galactosyltransferase Genes

| Source Organism | Sequence Description | GI Number |
|---|---|---|
| Lupinus angustifolius | galactomannan galactosyltransferase 1-like | XM_019567302.1 |
| Trigonella foenum-graecum | alpha galactosyltransferase | AJ245478.1 |
| Arachis ipaensis | galactomannan galactosyltransferase 1 | XM_016346122.2 |
| Arachis ipaensis | galactomannan galactosyltransferase 1 | XM_016346121.2 |
| Ziziphus jujuba | galactomannan galactosyltransferase 1-like | XM_016034856.1 |
| Ziziphus jujuba | galactomannan galactosyltransferase 1-like | XM_016034855.1 |
| Arachis duranensis | galactomannan galactosyltransferase 1 | XM_016108311.2 |
| Arachis duranensis | galactomannan galactosyltransferase 1 | XM_016108310.2 |
| Glycine max | galactomannan galactosyltransferase 1-like | XM_003539215.3 |
| Glycine max | galactomannan galactosyltransferase 1-like | XM_006590559.2 |
| Glycine max | unidentified | AC235306.1 |
| Glycine max | unidentified | AK245471.1 |
| Senna occidentalis | galactomannan galactosyltransferase | AJ938068.1 |
| Phaseolus vulgaris | hypothetical protein | XM_007156638.1 |
| Glycine max | galactomannan galactosyltransferase | XM_003517306.3 |
| Juglans regia | putative glycosyltransferase 7 | XM_018958015.1 |
| Prunus mume | galactomannan galactosyltransferase 1-like | XM_008239498.2 |
| Prunus mume | galactomannan galactosyltransferase 1-like | XM_008239489.2 |
| Prunus persica | galactomannan galactosyltransferase 1 | XM_007205133.2 |
| Iponoea nil | glycosyltransferase 6-like | XM_019317795.1 |
| Vigna radiata var. radiata | galactomannan galactosyltransferase 1-like | XM_014665934.1 |
| Lupinus angustifolius | galactomannan galactosyltransferase 1-like | XM_019589398.1 |
| Lupinus angustifolius | galactomannan galactosyltransferase 1-like | XM_019589395.1 |
| Lupinus angustifolius | galactomannan galactosyltransferase 1-like | XM_019589394.1 |
| Nelumbo nucifera | putative glycosyltransferase 7 | XM_010274767.2 |
| Vigna angularis | galactomannan galactosyltransferase 1-like | XM_017570547.1 |
| Vigna angularis var. angularis | unidentified | AP015043.1 |
| Pyrus × bretschneideri | galactomannan galactosyltransferase | XM_009364320.2 |
| Vitis vinifera | unidentified | AM447747.2 |
| Morus notabilis | galactomannan galactosyltransferase 1 | XM_010108622.1 |
| Malus domestica | galactomannan galactosyltransferase 1-like | NM_001328775.1 |
| Malus × domestica | galactomannan galactosyltransferase 1-like | XM_008363913.2 |
| Malus × domestica | unidentified | AB627270.1 |
| Malus × domestica | unidentified | HM122522.1 |
| Cucumis sativus | galactomannan galactosyltransferase 1-like | XM_004141806.2 |
| Malus × domestica | galactomannan galactosyltransferase 1-like | XM_008349663.1 |
| Cajanus cajan | galactomannan galactosyltransferase 1-like | XM_020374857.1 |
| Cajanus cajan | galactomannan galactosyltransferase 1-like | XM_020374856.1 |
| Capsicum annum | putative glycosyltransferase 7 | XM_016705445.1 |
| Malus × domestica | unidentified | HM122524.1 |
| Fragaria vesca | galactomannan galactosyltransferase 1-like | XM_004288217.2 |
| Solanum tuberosum | putative glycosyltransferase 7 | XM_006363751.2 |
| Solanum tuberosum | putative glycosyltransferase 7 | XM_006363750.2 |
| Medicago truncatula | galactosyl transferase | XM_003611508.2 |
| Medicago truncatula | unidentified | CT573500.2 |
| Solanum lycopersicum | putative glycosyltransferase 7 | XM_004231889.3 |
| Solanum lycopersicum | unidentified | AC226502.1 |
| Lycopersicon esculentum | unidentified | BT013963.1 |
| Sesamum indicum | glycosyltransferase 6-like | XM_011101097.2 |
| Cucumis melo | galactomannan galactosyltransferase 1-like | XM_008442195.2 |
| Cucumis melo | unidentified | LN713262.1 |
| Cucumis melo | unidentified | LN681875.1 |
| Solanum lycopersicum | unidentified | HG975514.1 |
| Solanum pennellii | putative glycosyltransferase 7 | XM_015208067.1 |
| Solanum pennellii | unidentified | HG975441.1 |
| Sesamum indicum | glycosyltransferase 6 | XM_011075379.2 |
| Coffea arabica | galactomannan galactosyltransferase | EU568117.1 |
| Cicer arietinum | galactomannan galactosyltransferase 1-like | XM_012718954.1 |
| Theobroma cacao | putative glycosyltransferase 7 | XM_007047507.2 |
| Theobroma cacao | unidentified | LT594788.1 |
| Erythranthe guttatus | glycosyltransferase 6-like | XM_012998642.1 |
| Populus trichocarpa | galactosyltransferase family protein | XM_002310854.2 |
| Prunus persica | glycosyltransferase 6 | XM_007208119.2 |
| Nicotiana attenuata | putative glycosyltransferase 7 | XM_019380314.1 |
| Gossypium arboreum | putative glycosyltransferase 7 | XM_017765398.1 |
| Gossypium arboreum | putative glycosyltransferase 7 | XM_017765397.1 |
| Gossypium hirsutum | putative glycosyltransferase 7 | XM_016879483.1 |
| Gossypium hirsutum | putative glycosyltransferase 7 | XM_016879482.1 |
| Gossypium raimondii | putative glycosyltransferase 7 | XM_012581704.1 |
| Gossypium raimondii | putative glycosyltransferase 7 | XM_012581703.1 |
| Nicotiana tomentosiformis | putative glycosyltransferase 7 | XM_009626576.2 |
| Prunus mume | glycosyltransferase 6-like | XM_008239940.2 |
| Populus euphratica | putative glycosyltransferase 7 | XM_011033007.1 |
| Populus euphratica | putative glycosyltransferase 7 | XM_011017963.1 |

TABLE 2-continued

Galactomannan Galactosyltransferase Genes

| Source Organism | Sequence Description | GI Number |
|---|---|---|
| *Musa acuminata* subsp. *malaccensis* | probable glycosyltransferase 7 | XM_009396086.2 |
| *Daucus carota* subsp. *sativus* | putative glycosyltransferase 7 | XM_017387245.1 |
| *Daucus carota* subsp. *sativus* | putative glycosyltransferase 7 | XM_017387244.1 |
| *Gossypium hirsutum* | putative glycosyltransferase 7 | XM_016818092.1 |
| *Gossypium raimondii* | putative glycosyltransferase 7 | XM_012614197.1 |
| *Arabis alpina* | unidentified | LT669794.1 |
| *Eucalyptus grandis* | putative glycosyltransferase 7 | XM_010029779.2 |
| *Nicotiana tabacum* | putative glycosyltransferase 7 | XM_016593700.1 |
| *Nicotiana sylvestris* | putative glycosyltransferase 7 | XM_009763295.1 |
| *Gossypium hirsutum* | putative glycosyltransferase 7 | XM_016864575.1 |
| *Gossypium arboreum* | galactomannan galactosyltransferase 1 | XM_017774502.1 |
| *Gossypium hirsutum* | putative glycosyltransferase 7 | XM_016850999.1 |
| *Gossypium hirsutum* | glycosyltransferase 6-like | XM_016841848.1 |
| *Gossypium raimondii* | glycosyltransferase 6-like | XM_012636540.1 |
| *Gossypium arboreum* | putative glycosyltransferase 7 | XM_017768866.1 |
| *Raphanus sativus* | glycosyltransferase 6-like | XM_018611230.1 |
| *Jatropha curcas* | galactomannan galactosyltransferase 1 | XM_012232035.2 |
| *Ricinus communis* | galactomannan galactosyltransferase 1 | XM_002513376.2 |
| *Raphanus sativus* | glycosyltransferase 6 | XM_018626243.1 |
| *Prunus mume* | putative glycosyltransferase 7 | XM_008227859.1 |

A lipase is an esterase that catalyzes the hydrolysis of fats, oils, and lipids. In one aspect, the gene that expresses lipase is isolated from a bacterium. In a further aspect, the bacterium is a *Micrococcus* species, a *Pseudomonas* species, a *Moraxella* species, or an *Acinetobacter* species. In a further aspect, the gene that expresses lipase has SEQ ID NO. 9 or at least 70% homology thereof, at least 75% homology thereof, at least 80% homology thereof, at least 85% homology thereof, at least 90% homology thereof, or at least 95% homology thereof. In a further aspect, the cellulose synthase is able to use mannose as a substrate instead of or in addition to glucose. In one aspect, the gene that expresses lipase can be positioned anywhere in the DNA construct disclosed herein. In one aspect, the gene that expresses lipase is positioned 5' (i.e., prior) to the gene that expresses cellulose synthase.

Other sequences expressing lipase or related or homologous genes can be identified in a database such as, for example, GenBank. In one aspect, sequences useful herein include those with the GI numbers listed in Table 3:

TABLE 3

Lipase Genes

| Source Organism | Sequence Description | GI Number |
|---|---|---|
| *Micrococcus* sp. HL-2003 | lipase gene | AY268069.1 |
| *Pseudomonas* sp. | esterase gene | M68491.1 |
| *Moraxella* L1 | lipase 1 | X53053.1 |

TABLE 3-continued

Lipase Genes

| Source Organism | Sequence Description | GI Number |
|---|---|---|
| *A. calcoaceticus* | carboxylesterase and peptidyl prolyl-cis-trans-isomerase | X74839.1 |
| *Acinetobacter* sp. ADP1 | genomic DNA | CR543861.1 |
| *A. calcoaceticus* | esterase | X71598.1 |
| *Pseudomonas trivialis* | genomic DNA | CP011507.1 |
| *Pseudomonas azotoformans* | genomic DNA | CP019856.1 |
| *Pseudomonas extremaustralis* | genomic DNA | LT629689.1 |
| *Pseudomonas fluorescens* | genomic DNA | CP005975.1 |
| *Pseudomonas fluorescens* | genomic DNA | CP010896.1 |
| *Pseudomonas fluorescens* | genomic DNA | AF228666.1 |
| *Pseudomonas simiae* | genomic DNA | CP007637.1 |
| *Pseudomonas fluorescens* | genomic DNA | AM181176.4 |
| *Pseudomonas Antarctica* | genomic DNA | CP015600.1 |
| *Pseudomonas fluorescens* | genomic DNA | CP015639.1 |
| *Pseudomonas fluorescens* | genomic DNA | LT907842.1 |
| *Pseudomonas* sp. NS1 | genomic DNA | CP022960.1 |
| *Pseudomonas poae* | genomic DNA | LT629706.1 |
| *Pseudomonas poae* | genomic DNA | CP004045.1 |
| *Pseudomonas rhodesiae* | genomic DNA | LT629801.1 |
| *Pseudomonas trivialis* | genomic DNA | LT629760.1 |
| *Pseudomonas azotoformans* | genomic DNA | LT629702.1 |
| *Pseudomonas Antarctica* | genomic DNA | LT629704.1 |
| *Pseudomonas fluorescens* | genomic DNA | CP012400.1 |
| *Pseudomonas azotoformans* | genomic DNA | CP014546.1 |
| *Pseudomonas yamanorum* | genomic DNA | LT629793.1 |
| *Pseudomonas prosekii* | genomic DNA | LT629762.1 |
| *Pseudomonas koreensis* | genomic DNA | CP014947.1 |
| *Pseudomonas libanensis* | genomic DNA | LT629699.1 |
| *Pseudomonas* sp. GR 6-02 | genomic DNA | CP011567.1 |
| *Pseudomonas fluorescens* | genomic DNA | CP014868.1 |
| *Pseudomonas fluorescens* | genomic DNA | CP011117.1 |
| *Pseudomonas fluorescens* | genomic DNA | S69066.1 |
| *Pseudomonas cedrina* | genomic DNA | LT629753.1 |
| *Pseudomonas* sp. bs2935 | genomic DNA | LT629744.1 |
| *Pseudomonas fluorescens* | genomic DNA | CP017296.1 |
| *Pseudomonas* sp. WCS374 | genomic DNA | CP007638.1 |
| *Pseudomonas fluorescens* | genomic DNA | CP003041.1 |
| *Pseudomonas corrugate* | genomic DNA | LT629798.1 |
| *Pseudomonas corrugate* | genomic DNA | CP014262.1 |
| *Pseudomonas mediterranea* | genomic DNA | LT629790.1 |
| *Pseudomonas tolaasii* | genomic DNA | CP020369.1 |
| *Pseudomonas fluorescens* | genomic DNA | CP015638.1 |
| *Pseudomonas fluorescens* | genomic DNA | CP015637.1 |
| *Pseudomonas* sp. TKP | genomic DNA | CP006852.1 |
| Synthetic construct | carboxylesterase | HM212419.1 |
| Synthetic construct | carboxylesterase | FJ213454.1 |
| *Pseudomonas* sp. FDAARGOS 380 | genomic DNA | CP023969.1 |
| *Pseudomonas synxantha* | genomic DNA | LT629786.1 |
| *Pseudomonas orientalis* | genomic DNA | LT629782.1 |
| *Pseudomonas* sp. URMO17WK12:I11 | genomic DNA | LN854573.1 |

In another aspect, said construct further includes d) a promoter, e) a terminator or stop sequence, f) a gene that confers resistance to an antibiotic (a "selective marker"), g) a reporter protein, or a combination thereof.

In another aspect, the DNA construct has the following genetic components: (1) a promoter, (2) a gene that expresses cellulose synthase, (3) a gene that expresses galactomannan galactosyltransferase, and (4) a terminator or stop sequence.

In an alternative aspect, the DNA construct has the following genetic components: (1) a promoter, (2) a gene that expresses lipase, (3) a gene that expresses cellulose synthase, (4) a gene that expresses galactomannan galactosyltransferase, and (5) a terminator or stop sequence.

In one aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is an operon such as, for example, the LAC operon. As used herein, an "operon" is a segment of DNA containing a group of genes wherein the group is controlled by a single promoter. Genes included in an operon are all transcribed together. In a further aspect, the operon is a LAC operon and can be induced when lactose crosses the cell membrane of the biological device.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In one aspect, the promoter has SEQ ID NO. 5 or at least 70% homology thereof of the plasmid pYES2. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides of a ribosomal binding site. In one aspect, the promoter may be native to the vectors described herein. In another aspect, the promoter is positioned before the gene that expresses lipase, cellulose synthase, galactomannan galactosyltransferase, or a combination thereof.

In one aspect, the promoter is a GAL1 promoter. In another aspect, the GAL1 promoter is native to the plasmid used to create the vector. In another aspect, a GAL1 promoter is positioned before the gene that expresses cellulose synthase and the gene that expresses galactomannan galactosyltransferase. In another aspect, the promoter is a GAL1 promoter obtained from or native to the pYES2 plasmid.

In another aspect, the promoter is a T7 promoter. In a further aspect, the T7 promoter is native to the plasmid used to create the vector. In still another aspect, the GAL1 promoter is positioned before any or all of the genes in the construct, or is positioned before the LAC operon. In yet another aspect, the promoter is a T7 promoter obtained from or native to the pETDuet-1 plasmid.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is a T7 terminator. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the vector contains one or more ribosomal binding sites. As used herein, a "ribosomal binding site" is a sequence of nucleotides located 5' to the start codon of an mRNA that recruits a ribosome to initiate protein translation. In one aspect, the ribosomal binding site can be positioned before any or all genes in a DNA construct, or a before a subset of genes in a DNA construct.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g. amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interested can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, this incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and are commercially available. Such vectors include, but are not limited to, pWLneo, pSV2cat, pOG44, pXT1, pSG (Strategene), pSVK3, pBSK, pBR322, pYES, pYES2, pBSKII, pUC, pUC19, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the skilled artisan to select host cells that have been successfully transfected with the plasmids (for example, by growing the host cells in a medium containing the antibiotic).

In certain aspects, the DNA construct includes a ribosomal binding site. In one aspect, the ribosomal binding site in the DNA construct is AGGAGG or a derivative or variant thereof. In one aspect, the ribosomal binding site is native to the vector used herein. In certain aspects, when the DNA construct further includes a ribosomal switch. In one aspect, the ribosomal switch is SEQ ID NO. 6 or at least 70% homology thereof. The ribosomal binding site and optional ribosomal switch are positioned after the gene for galactomannan galactosyltransferase from 5' to 3'.

In another aspect, the DNA construct includes a terminator. In one aspect, the terminator in the DNA construct is a known stop codon (TAA, TAG, TGA) or a derivative or variant thereof. In a further aspect, the terminator is native to the vector in which the DNA construct is incorporated. The terminator is positioned after the gene for galactomannan galactosyltransferase from 5' to 3'.

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector which confers antibiotic resistance can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 7 or at least 70% homology thereof. The amount of fluorescence that is produced by the biological device can be correlated to the amount of DNA incorporated into the plant cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

FIGS. 1-3, 19A-B, and 22A-B provide non-limiting examples of DNA constructs described herein. In one aspect, the construct is a pYES2 plasmid having from 5' to 3' the following genetic components in the following order: (a) a T7 promoter; (b) a gene that expresses cellulose synthase; (c) a gene that expresses galactomannan galactosyltransferase; (d) a T7 terminator or stop codon. In another aspect, the construct is a pYES2 plasmid having from 5' to 3' the following genetic components in the following order: (a) a Gal1 promoter; (b) a gene that expresses cellulose synthase;

(c) a gene that expresses galactomannan galactosyltransferase; (d) a CYC1 terminator or stop codon.

In another aspect, the construct is a pYES2 plasmid having from 5' to 3' the following genetic components in the following order: (a) a Gal1 promoter; (b) a gene that expresses cellulose synthase; (c) a CYC1 terminator; (d) a Gal1 promoter; (e) a gene that expresses galactomannan galactosyltransferase; and (f) a CYC1 terminator.

In another aspect, the construct is a pYES2 plasmid having from 5' to 3' the following genetic components in the following order: (a) a Gal1 promoter; (b) a gene that expresses lipase; (c) a CYC1 terminator; (d) a Gal1 promoter; (b) a gene that expresses cellulose synthase; (e) a CYC1 terminator; (f) a Gal1 promoter; (g) a gene that expresses galactomannan galactosyltransferase; and (h) a CYC1 terminator.

In still another aspect, the construct is a pETDuet-1 plasmid having from 5' to 3' the following genetic components in the following order: (a) a gene that expresses lipase, (b) a T7 promoter, (c) a LAC operon, (d) a ribosomal binding site, (e) a gene that expresses cellulose synthase, (f) a ribosomal binding site, and (g) a gene that expresses galactomannan galactosyltransferase.

In one aspect, the construct is a pYES2 plasmid having from 5' to 3' the following genetic components in the following order: (a) a T7 promoter; (b) a gene that expresses lipase, (c) a gene that expresses cellulose synthase; (d) a gene that expresses galactomannan galactosyltransferase; (e) a T7 terminator or stop codon. In another aspect, the construct is a pYES2 plasmid having from 5' to 3' the following genetic components in the following order: (a) a Gal1 promoter; (b) a gene that expresses lipase, (c) a gene that expresses cellulose synthase; (d) a gene that expresses galactomannan galactosyltransferase; (e) a CYC1 terminator or stop codon.

In another aspect, the construct is a pYES2 plasmid having from 5' to 3' the following genetic components in the following order: (a) a Gal1 promoter; (b) a gene that expresses lipase, (c) a gene that expresses cellulose synthase; (d) a CYC1 terminator; (e) a Gal1 promoter; (f) a gene that expresses galactomannan galactosyltransferase; and (g) a CYC1 terminator.

In one aspect, the construct comprises from 5' to 3' the following genetic components in the following order: (a) a T7 promoter having SEQ ID NO 5 or at least 70% homology thereof; (b) a gene that expresses cellulose synthase having SEQ ID NO 1 or at least 70% homology thereof; (c) a gene that expresses galactomannan galactosyltransferase having SEQ ID NO 4 or at least 70% homology thereof; (d) a ribosomal binding site; and (e) a terminator or stop codon.

In another aspect, the construct is a plasmid having from 5' to 3' the following genetic components in the following order: (a) a T7 promoter having SEQ ID NO 5 or at least 70% homology thereof; (b) a gene that expresses cellulose synthase having SEQ ID NO 1 or at least 70% homology thereof; (c) a gene that expresses galactomannan galactosyltransferase having SEQ ID NO 4 or at least 70% homology thereof; (d) a ribosomal binding site; and (e) a terminator or stop codon.

In another aspect, the construct is a pYES2 plasmid having from 5' to 3' the following genetic components in the following order: (a) a T7 promoter having SEQ ID NO 5 or at least 70% homology thereof; (b) a gene that expresses cellulose synthase having SEQ ID NO 1 or at least 70% homology thereof; (c) a gene that expresses galactomannan galactosyltransferase having SEQ ID NO 4 or at least 70% homology thereof; (d) a ribosomal binding site; and (e) a terminator or stop codon.

In one aspect, the construct is a plasmid having from 5' to 3' the following genetic components in the following order: (a) a gene that expresses lipase having SEQ ID NO. 9 or at least 70% homology thereto, (b) a T7 promoter, (c) a LAC operon, (d) a ribosomal binding site, (e) a gene that expresses cellulose synthase having SEQ ID NO. 1 or at least 70% homology thereto, (f) a ribosomal binding site, and (g) a gene that expresses galactomannan galactosyltransferase having SEQ ID NO. 4 or at least 70% homology thereto.

In one aspect, the construct is a pETDuet-1 plasmid having from 5' to 3' the following genetic components in the following order: (a) a gene that expresses lipase having SEQ ID NO. 9 or at least 70% homology thereto, (b) a T7 promoter, (c) a LAC operon, (d) a ribosomal binding site, (e) a gene that expresses cellulose synthase having SEQ ID NO. 1 or at least 70% homology thereto, (f) a ribosomal binding site, and (g) a gene that expresses galactomannan galactosyltransferase having SEQ ID NO. 4 or at least 70% homology thereto.

In another aspect, the construct is a pYES2 plasmid having from 5' to 3' the following genetic components in the following order: (a) a Gal1 promoter; (b) a gene that expresses cellulose synthase having SEQ ID NO 1 or at least 70% homology thereof; (c) a gene that expresses galactomannan galactosyltransferase having SEQ ID NO 4 or at least 70% homology thereof; (d) a ribosomal binding site; and (e) a terminator or stop codon.

In one aspect, the construct comprises from 5' to 3' the following genetic components in the following order: (a) a T7 promoter having SEQ ID NO 5 or at least 70% homology thereof; (b) a gene that expresses lipase having SEQ ID NO. 9 or at least 70% homology thereof, (c) a gene that expresses cellulose synthase having SEQ ID NO 1 or at least 70% homology thereof; (d) a gene that expresses galactomannan galactosyltransferase having SEQ ID NO 4 or at least 70% homology thereof; (e) a ribosomal binding site; and (f) a terminator or stop codon.

In another aspect, the construct is a plasmid having from 5' to 3' the following genetic components in the following order: (a) a T7 promoter having SEQ ID NO 5 or at least 70% homology thereof; (b) a gene that expresses lipase having SEQ ID NO. 9 or at least 70% homology thereof; (c) a gene that expresses cellulose synthase having SEQ ID NO 1 or at least 70% homology thereof; (d) a gene that expresses galactomannan galactosyltransferase having SEQ ID NO 4 or at least 70% homology thereof; (e) a ribosomal binding site; and (f) a terminator or stop codon.

In another aspect, the construct is a pYES2 plasmid having from 5' to 3' the following genetic components in the following order: (a) a T7 promoter having SEQ ID NO 5 or at least 70% homology thereof; (b) a gene that expresses lipase having SEQ ID NO. 9 or at least 70% homology thereof; (c) a gene that expresses cellulose synthase having SEQ ID NO 1 or at least 70% homology thereof; (d) a gene that expresses galactomannan galactosyltransferase having SEQ ID NO 4 or at least 70% homology thereof; (e) a ribosomal binding site; and (f) a terminator or stop codon.

In another aspect, the construct is a pYES2 plasmid having from 5' to 3' the following genetic components in the following order: (a) a Gal1 promoter; (b) a gene that expresses lipase having SEQ ID NO. 9 or at least 70% homology thereto; (c) a gene that expresses cellulose synthase having SEQ ID NO 1 or at least 70% homology thereof; (d) a gene that expresses galactomannan galactosyltransferase having SEQ ID NO 4 or at least 70% homology thereof; (e) a ribosomal binding site; and (f) a terminator or stop codon.

In another aspect, the construct includes from 5' to 3' the following genetic components in the following order: (a) a gene that expresses cellulose synthase and (b) a gene that expresses galactomannan galactosyltransferase.

In another aspect, the construct includes from 5' to 3' the following genetic components in the following order: (a) a Gal1 promoter; (b) a gene that expresses cellulose synthase; (c) a gene that expresses galactomannan galactosyltransferase; and (d) a CYC1 terminator or stop codon.

In another aspect, the construct includes from 5' to 3' the following genetic components in the following order: (a) a gene that expresses lipase, (b) a gene that expresses cellulose synthase, and (c) a gene that expresses galactomannan galactosyltransferase.

In another aspect, the construct includes from 5' to 3' the following genetic components in the following order: (a) a Gal1 promoter; (b) a gene that expresses lipase, (c) a gene that expresses cellulose synthase; (d) a gene that expresses galactomannan galactosyltransferase; and (e) a CYC1 terminator or stop codon.

In still another aspect, the construct includes from 5' to 3' the following genetic components in the following order: (a) a gene that expresses lipase, (b) a T7 promoter, (c) a LAC operon, (d) a ribosomal binding site, (e) a gene that expresses cellulose synthase, (f) a ribosomal binding site, and (g) a gene that expresses galactomannan galactosyltransferase.

In another aspect, the construct includes from 5' to 3' the following genetic components in the following order: (a) a Gal1 promoter; (b) a gene that expresses cellulose synthase; (c) a CYC1 terminator; (d) a Gal1 promoter; (e) a gene that expresses galactomannan galactosyltransferase; and (f) a CYC1 terminator.

In another aspect, the construct includes the following genetic components: (a) a T7 promoter; (b) a gene that expresses cellulose synthase having SEQ ID NO. 1 or at least 70% homology thereof; and (c) a gene that expresses galactomannan galactosyltransferase having SEQ ID NO. 4 or at least 70% homology thereof.

In another aspect, the construct includes the following genetic components: (a) a Gal1 promoter; (b) a gene that expresses cellulose synthase having SEQ ID NO. 1 or at least 70% homology thereof, and (c) a gene that expresses galactomannan galactosyltransferase having SEQ ID NO. 4 or at least 70% homology thereof.

In another aspect, the construct includes from 5' to 3' the following genetic components in the following order: (a) a Gal1 promoter; (b) a gene that expresses cellulose synthase having SEQ ID NO. 1 or at least 70% homology thereof, and (c) a gene that expresses galactomannan galactosyltransferase having SEQ ID NO. 4 or at least 70% homology thereof.

In another aspect, the construct includes from 5' to 3' the following genetic components in the following order: (a) a Gal1 promoter; (b) a gene that expresses cellulose synthase; (c) a CYC1 terminator; (d) a Gal1 promoter; (e) a gene that expresses galactomannan galactosyltransferase; and (f) a CYC1 terminator.

In another aspect, the construct includes from 5' to 3' the following genetic components in the following order: (a) a Gal1 promoter; (b) a gene that expresses cellulose synthase having SEQ ID NO. 4 or at least 70% homology thereof, (c) a CYC1 terminator; (d) a Gal1 promoter; (e) a gene that expresses galactomannan galactosyltransferase having SEQ ID NO. 1 or at least 70% homology thereof, and (f) a CYC1 terminator.

In another aspect, the construct is a pYES2 plasmid having from 5' to 3' the following genetic components in the following order: (a) a Gal1 promoter; (b) a gene that expresses cellulose synthase or at least 70% homology thereof; (c) a CYC1 terminator; (d) a Gal1 promoter; (e) a gene that expresses galactomannan galactosyltransferase or at least 70% homology thereof, and (f) a CYC1 terminator.

In another aspect, the construct includes from 5' to 3' the following genetic components in the following order: (a) a Gal1 promoter; (b) a gene that expresses cellulose synthase; (c) a CYC1 terminator; (d) a Gal1 promoter; (e) a gene that expresses galactomannan galactosyltransferase; and (f) a CYC1 terminator.

In another aspect, the construct includes the following genetic components: (a) a T7 promoter; (b) a gene that expresses cellulose synthase having SEQ ID NO. 1 or at least 70% homology thereof; and (c) a gene that expresses galactomannan galactosyltransferase having SEQ ID NO. 4 or at least 70% homology thereof.

In another aspect, the construct includes the following genetic components: (a) a Gal1 promoter; (b) a gene that expresses lipase having SEQ ID NO 9 or at least 70% homology thereof, (c) a gene that expresses cellulose synthase having SEQ ID NO. 1 or at least 70% homology thereof; and (d) a gene that expresses galactomannan galactosyltransferase having SEQ ID NO. 4 or at least 70% homology thereof.

In another aspect, the construct includes from 5' to 3' the following genetic components in the following order: (a) a Gal1 promoter; (b) a gene that expresses lipase having SEQ ID NO. 9 or at least 70% homology thereof, (c) a gene that expresses cellulose synthase having SEQ ID NO. 1 or at least 70% homology thereof, and (d) a gene that expresses galactomannan galactosyltransferase having SEQ ID NO. 4 or at least 70% homology thereof.

In another aspect, the construct includes from 5' to 3' the following genetic components in the following order: (a) a Gal1 promoter; (b) a gene that expresses lipase, (c) a gene that expresses cellulose synthase; (d) a CYC1 terminator; (e) a Gal1 promoter; (f) a gene that expresses galactomannan galactosyltransferase; and (g) a CYC1 terminator.

In another aspect, the construct includes from 5' to 3' the following genetic components in the following order: (a) a Gal1 promoter; (b) a gene that expresses lipase having SEQ ID NO. 9 or at least 70% homology thereof; (c) a gene that expresses cellulose synthase having SEQ ID NO. 4 or at least 70% homology thereof; (d) a CYC1 terminator; (e) a Gal1 promoter; (f) a gene that expresses galactomannan galactosyltransferase having SEQ ID NO. 1 or at least 70% homology thereof; and (g) a CYC1 terminator.

In still another aspect, the construct includes from 5' to 3' the following genetic components in the following order: (a) a gene that expresses lipase having SEQ ID NO. 9 or at least 70% homology thereto; (b) a T7 promoter; (c) a LAC operon; (d) a ribosomal binding site; (e) a gene that expresses cellulose synthase having SEQ ID NO. 4 or at least 70% homology thereto; (f) a ribosomal binding site; and (g) a gene that expresses galactomannan galactosyltransferase having SEQ ID NO. 1 or at least 70% homology thereto.

In another aspect, the construct is a pYES2 plasmid having from 5' to 3' the following genetic components in the following order: (a) a Gal1 promoter; (b) a gene that expresses lipase or at least 70% homology thereof; (c) a gene that expresses cellulose synthase or at least 70% homology thereof; (d) a CYC1 terminator; (e) a Gal1 promoter; (f) a gene that expresses galactomannan galactosyltransferase or at least 70% homology thereof; and (g) a CYC1 terminator.

In still another aspect, the construct is a pETDuet-1 plasmid having from 5' to 3' the following genetic components in the following order: (a) a gene that expresses lipase having SEQ ID NO. 9 or at least 70% homology thereto; (b) a T7 promoter; (c) a LAC operon; (d) a ribosomal binding site; (e) a gene that expresses cellulose synthase having SEQ ID NO. 4 or at least 70% homology thereto; (f) a ribosomal binding site; and (g) a gene that expresses galactomannan galactosyltransferase having SEQ ID NO. 1 or at least 70% homology thereto.

Figure 3A:
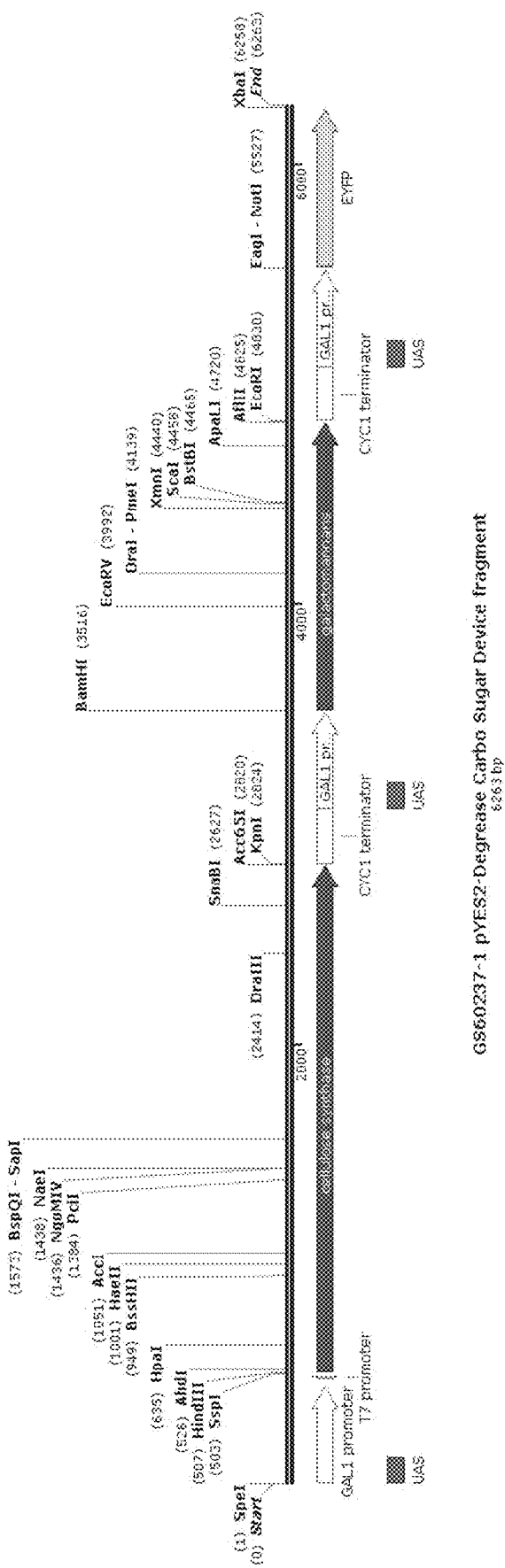
FIGS. 3A and 3B show, respectively, a linear and circular schematic of a constructed pYES2 plasmid showing the direction, placement, and size of genetic parts used of an exemplary DNA device described herein.
Figure 3B:
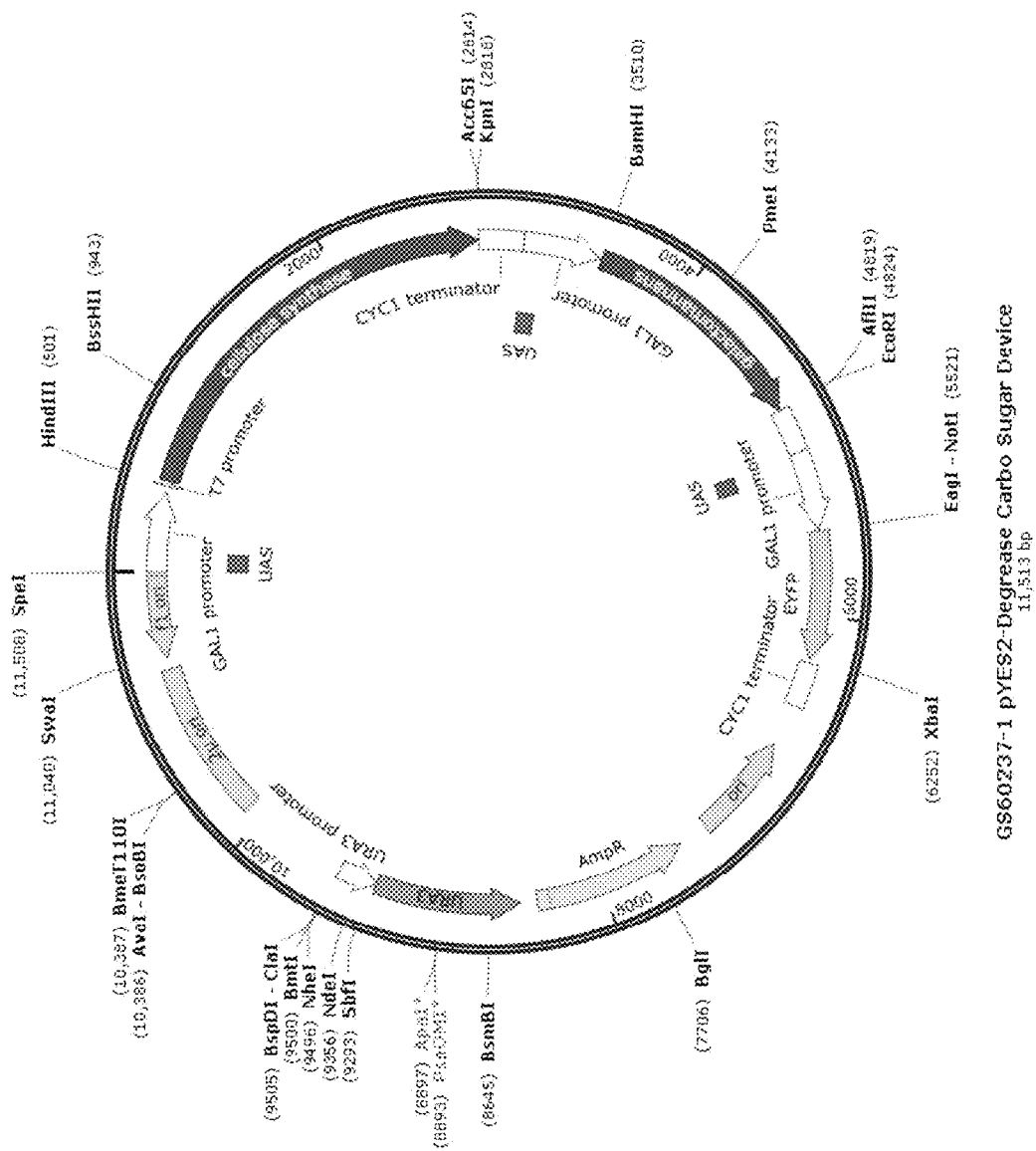
Figure 19A:
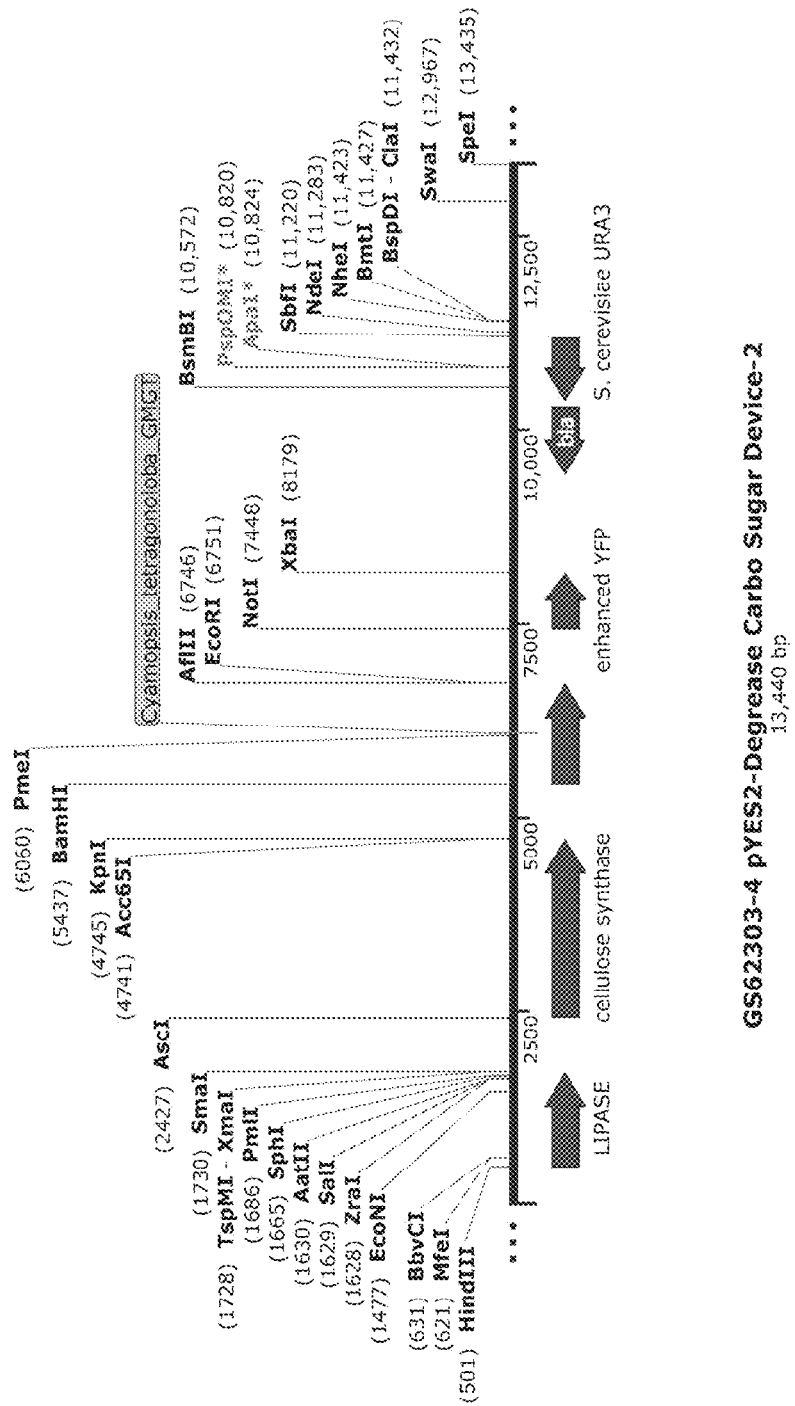
FIGS. 19A and 19B show, respectively, a linear and circular schematic of a constructed pYES2 plasmid showing the direction, placement, and size of genetic parts used of a second exemplary DNA device described herein.
Figure 19B:
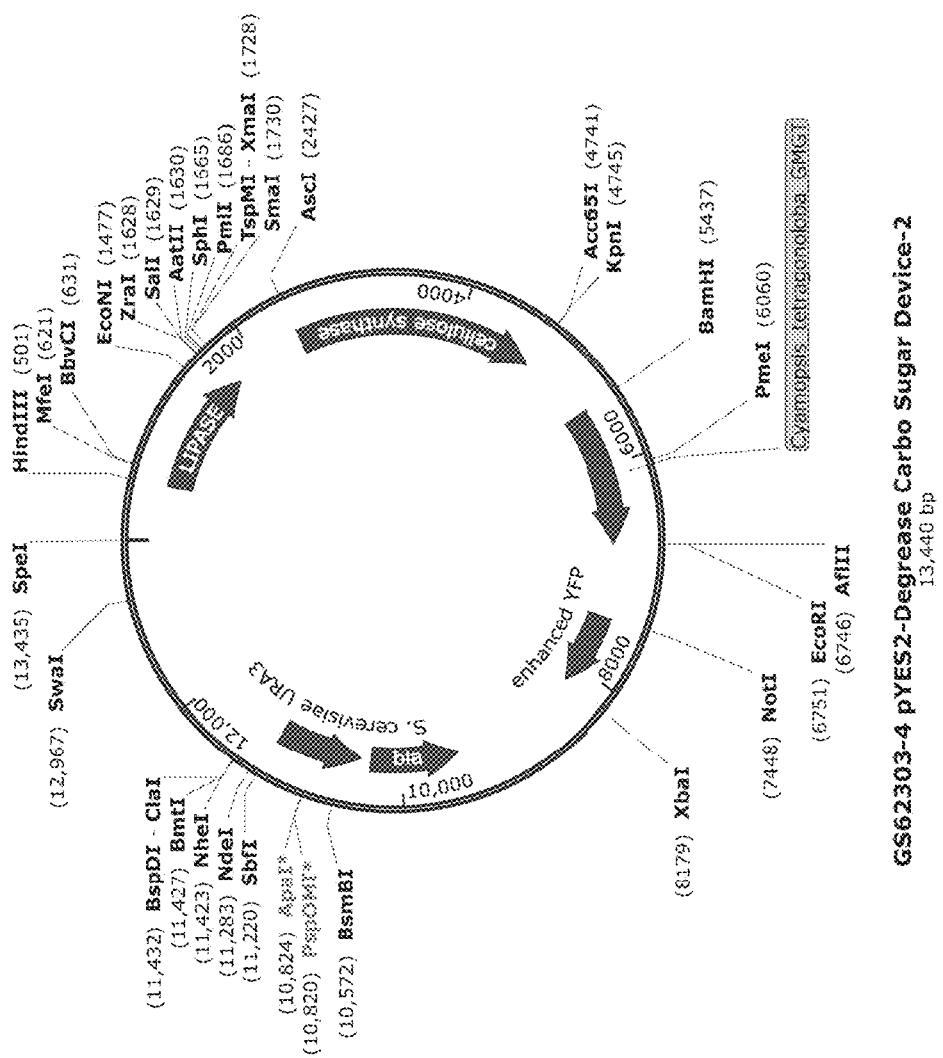
Figure 20A:
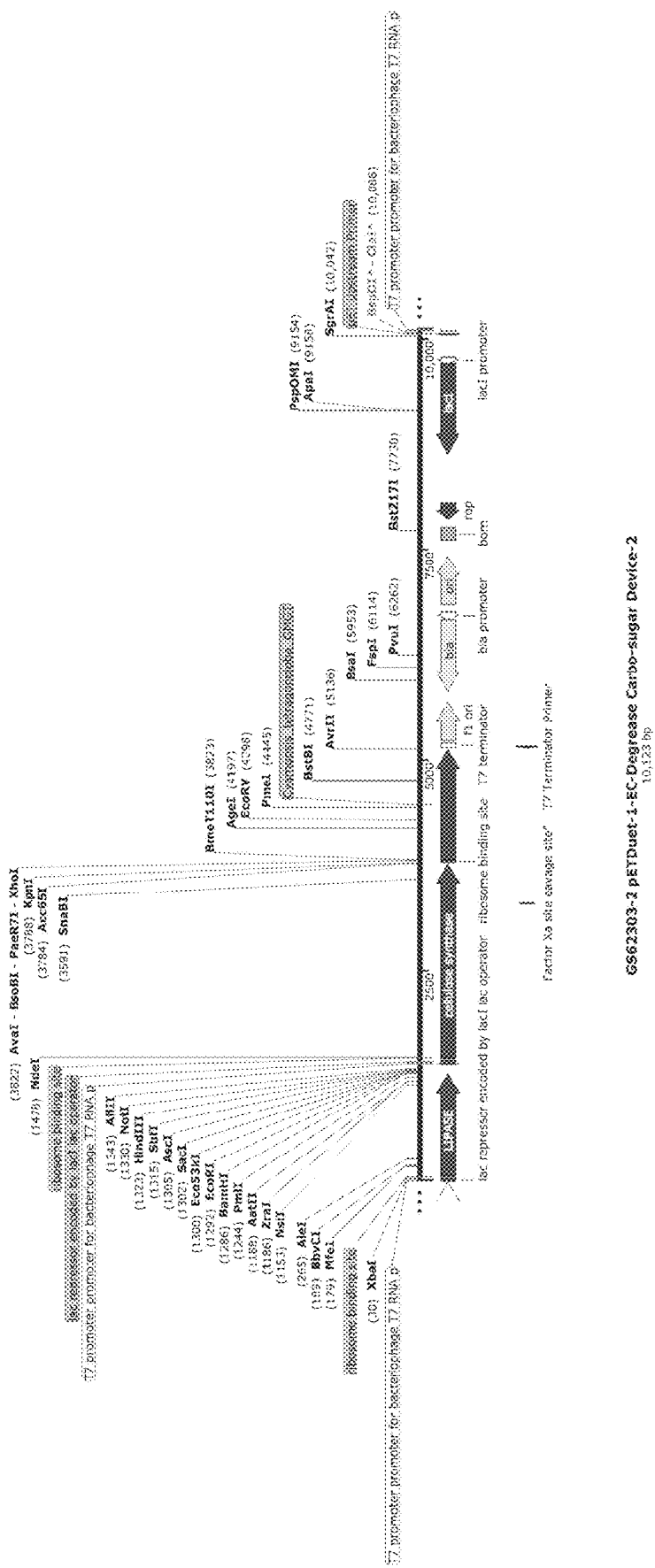
FIGS. 20A and 20B show, respectively, a linear and circular schematic of a constructed pETDuet-1 plasmid showing the direction, placement, and size of genetic parts used of a second exemplary DNA device described herein.
Figure 20B:
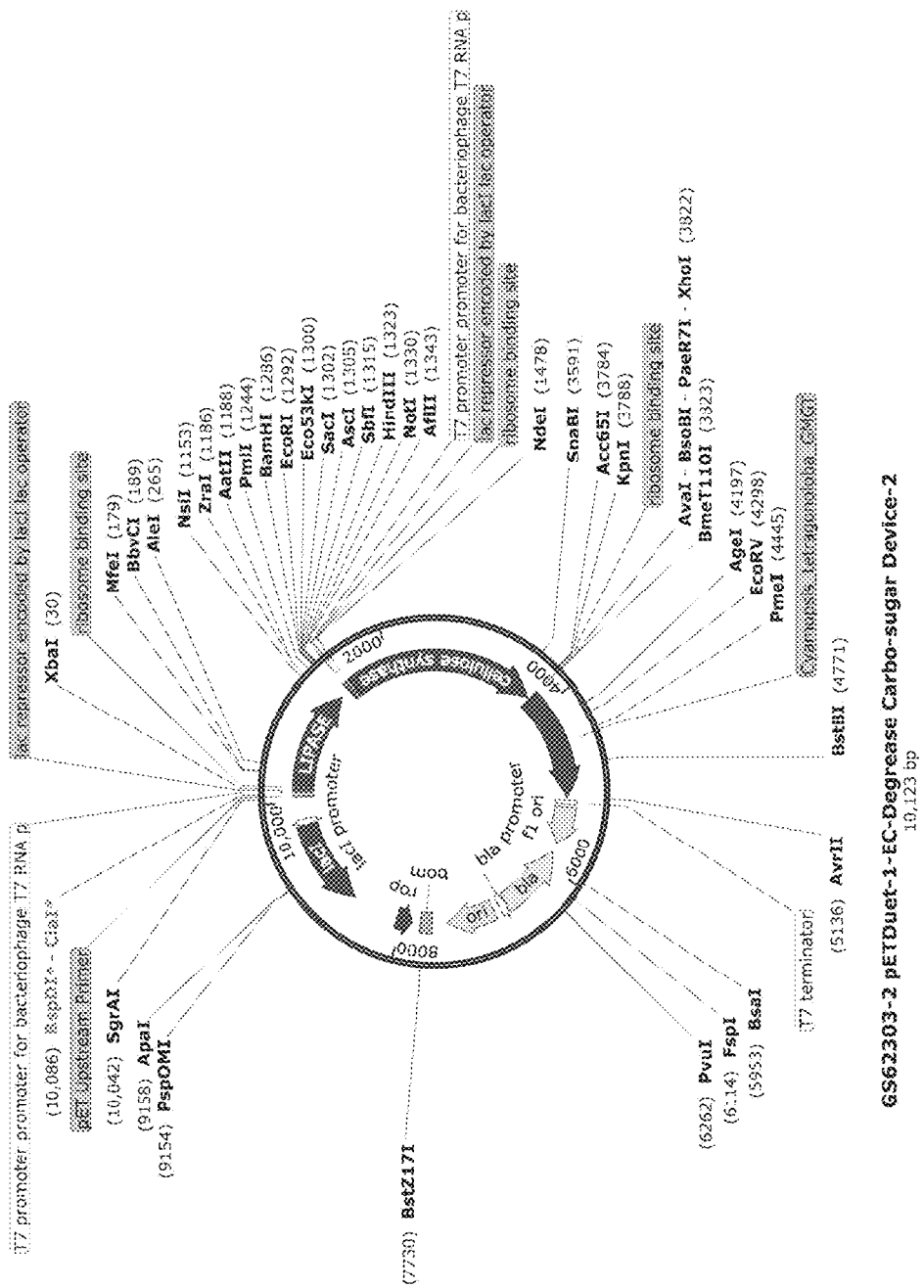

In one aspect, the construct has SEQ ID NO. 8, which is depicted in FIGS. 3A and 3B. In another aspect, the construct has SEQ ID NO. 10, which is depicted in FIGS. 19A and 19B. In still another aspect, the construct has SEQ ID NO. 11, which is depicted in FIGS. 20A and 20B.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce carbo sugars. "Heterologous" genes and proteins are genes and proteins that have been experimentally inserted into a cell that are not normally expressed by that cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Carbo Sugars

The biological devices described herein are useful in the production of carbo sugars. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at a stationary phase. Minimal media results in slow growth and low final cell densities. Efficient agitation and aeration increase final cell densities.

In one aspect, host cells may be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated and include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Culturing or fermenting of host cells may be accomplished by any technique known in the art. In one aspect, batch fermentation may be conducted. In batch fermentation, the composition of the culture medium is set at the beginning and the system is closed to future artificial alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods which are non-fermentative.

In one aspect, the method involves growing the biological devices described herein for a sufficient time to produce carbo sugars. The ordinary artisan will be able to choose a culture medium and optimum culture conditions based on the biological identity of the host cells. In a further aspect, a salt or electrolyte can optionally be added to the culture medium. Without wishing to be bound by theory, the salt can help to solubilize the carbo sugar as it is produced. In one aspect, the salt is present in solution at about a 0.1%, 0.2%, 0.5%, 1%, 1.5%, 2%, 2.5%, 3%, or 5% concentration. In a still further aspect, the salt is KCl. In this aspect, the presence of KCl can cause the appearance of a transient, transparent blue color when placed in solution with the carbo sugar. Exemplary procedures for producing carbo sugars using the biological devices described herein are provided in the Examples. In one aspect, the amount of carbo sugar produced by the microbial host cells as described above is from 1.1 to 10-fold greater than the amount of carbo sugar produced by nontransformed (control) microbial cells of the same species and strain. In a further aspect, the carbo sugar produced by the microbial host cells as described above is free from lignin.

In certain aspects, after culturing the biological device to produce the carbo sugar, the host cells of the device can be lysed with one or more enzymes. For example, when the host cells are yeast, the yeast cells can be lysed with lyticase. In one aspect, the lyticase concentration can be 500, 600, 700, 800, 900, or 1000 µL per liter of culture, where any value can be the lower and upper end-point of a range (e.g., 500 to 900 µL, 600 to 800 µL, etc.). In other aspects, the biological device is sonicated and/or autoclaved to disrupt the host cells.

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, chitosan can be added until a concentration of 0.0015, 0.0025, 0.0050, 0.0075, 0.01, 0.015, 0.02, 0.03, 0.04, or 0.05, where any value can be a lower and upper end-point of a range (e.g., 0.005 to 0.02, 0.0075 to 0.015, etc.) is achieved in the culture. Still further in this aspect, the chitosan is present at a concentration of 0.01%.

In a further aspect, the carbo sugar can be collected, separated from the microbial cells (lysed or intact), and/or purified through any technique known in the art such as, for example, precipitation, centrifugation, filtration, and the like. In one aspect, the carbo sugar can be purified via microfiltration to remove impurities. In one aspect, the microfilter has a pore size of 0.3 µm, 0.35 µm, 0.4 µm, 0.45 µm, 0.35 µm, 0.55 µm, 0.6 µm, 0.65 µm, 0.7 µm, or 0.8 µm, where any value can be a lower and upper end-point of a range (e.g., 0.3 µm to 0.5 µm). The Examples provide an exemplary procedure for producing and purifying the carbo sugars described herein.

In another aspect, the carbo sugar can be chemically-modified to produce additional desirable properties. Alternatively compositions composed of the carbo sugar with lysed and/or intact host cells (e.g., yeast) can be used herein, where it is not necessary to separate the host cells and other components from the carbo sugar.

In one aspect, the carbo sugars can be produced in 24-48 hours from transformed host cells at a cost of approximately $0.50 per kilogram. In another aspect, the carbo sugar is provided in solution. In an alternative aspect, the carbo sugar is provided in powdered or dried form.

IV. Applications of the Carbo Sugars

In certain aspects, the carbo sugars can be dissolved in an aqueous electrolyte solution. The electrolyte solution can be, for example, aqueous potassium chloride, sodium chloride, or calcium chloride. In one aspect, the electrolyte solution is a 2% solution of potassium chloride in water at pH 7-8. The pH of the electrolyte solution may be adjusted using any of a variety of acids, bases, or buffer systems known in the art.

In other aspects, the presence of metal ions, crosslinking, temperature, solution pH, and polymer concentration can also affect the viscosity of solutions containing the carbo sugars described herein. In one aspect, crosslinking reactions can be performed to link the side chains of the carbo sugars to one another.

In one aspect, the carbo sugars disclosed herein are free from impurities such as soy impurities and pesticide residues that are known to cause adverse reactions such as allergies or illnesses in some human subjects.

In one aspect, the carbo sugars disclosed herein can be used in the petroleum industry. In a further aspect, the carbo sugars can be included as a component of a hydraulic fracturing fluid, as a component of a drilling fluid, or to alter the viscosity of a crude petroleum product. For example, the carbo sugar as an aqueous solution can be used alone or in combination with other components as a fracturing fluid typically used in hydraulic fracturing.

In another aspect, the carbo sugars disclosed herein can be used in thickening textile and carpet dyes, facilitating paper processing, waterproofing and/or gelling in explosive compositions, binding pharmaceutical tablets, thickening cosmetics and toiletry preparations, controlling the viscosity of fire retardants, drug delivery, flocculating and/or flotation in metallurgy and/or mining applications, or as an additive in the food industry. In a further aspect, the carbo sugars disclosed herein can be used as a thickener, stabilizer, binder, or texturizing agent in food products such as baked goods, dairy products, meat, condiments, canned goods, ice cream, hot cereals, and the like.

In some aspects, compositions including carbo sugars can include other ingredients such as, for example, electrolyte solutions, fillers, particulates, surfactants, and the like. In certain aspects, compositions including the carbo sugars can be used as fluids for hydraulic fracturing. In some aspects, the carbo sugars used for hydraulic fracturing can further include petroleum oil.

In one aspect, surfactants can act in concert with the carbo sugar to alter the viscosity and friction properties of petroleum samples and compositions. The surfactant can be of any type including, for example, a cationic surfactant, an anionic surfactant, a nonionic surfactant, an amphiphilic surfactant, a zwitterionic surfactant, or a combination thereof. In one aspect, the surfactant is a nonionic surfactant such as, for example, ethoxylated alcohols, polysorbate 20, or polysorbate 80. In another aspect, the surfactant is a zwitterionic surfactant such as, for example, soy lecithin. In another aspect, the fillers and particulates can be used as proppants during hydraulic fracturing. As used herein, "proppant" refers to any material that can keep a hydraulic fracture open. Proppants may exert their effects either during or after hydraulic fracturing. Proppants include materials such as sand, ceramic particles, glass, bauxite, and combinations thereof.

In certain aspects, the carbo sugars described and disclosed herein can be used to alter the viscosity of petroleum oil. In one aspect, the carbo sugars can be directly mixed with petroleum oil. In another aspect, the carbo sugars can first be diluted with a solution of an electrolyte, then mixed with petroleum oil. In another aspect, the carbo sugars can be mixed with guar derived from plant-based sources prior to being placed into contact with petroleum oil. In a further aspect, compositions composed of the carbo sugars described herein can additionally include a surfactant.

In one aspect, contacting petroleum oil with carbo sugar compositions disclosed herein can alter the API gravity of the petroleum oil. "API gravity" as used herein refers to a set of standards developed by the American Petroleum Institute to classify the density of petroleum liquids compared to water. API gravity corresponds to grades of oil; light crude oil typically has API gravity of 31.1° API, medium crude oil between 22.3 and 31.1° API, and heavy crude oil below 22.3° API. API gravity can be derived from density which can be measured by methods such as, for example, ASTM D1298 or ASTM D4052.

In a further aspect, the altered API gravity can be increased; that is, the viscosity of the petroleum oil is reduced through contact with the carbo sugar compositions. In certain aspects, alteration of the viscosity of the petroleum oil facilitates downstream processing of the petroleum oil.

In another aspect, the carbo sugars described herein can be used for the bioremediation of polluted water and soil. For example, the carbo sugars can be used for the biodegradation of petroleum products that have contaminated the environment. In another aspect, the carbo sugars described herein can be used for the biodegradation of petroleum products present in soil and the surface water as well as for the bioremediation and enhancement of soil condition to support healthy plant growth.

Pollution of the environment, particularly contamination of water and soil, results in extraordinary damage to the environment and loss of vitality and productivity. Such pollution and general degradation also causes enormous economic loss to fishing, farming and tourist industries. The occurrence of large scale petroleum pollution is a frequent occurrence, and a number of potential solutions for bioremediation of petroleum pollution have been tried or proposed. For example, current cleanup practices include: 1) physical removal of the polluting petroleum by use of absorption media, 2) dispersal using detergents, 3) burning, 4) microbial degradation under ideal certain conditions, 5) agglomeration of oil on water and sinking to the floor of the water body, and 6) use of organic chemicals, such as kerosene based dispersants, to dissolve and disperse the oil. All of these methodologies are expensive to implement and have very limited usefulness. Further, even under ideal conditions these methods are often hazardous to carry out and extremely difficult to use to effectively clean up the pollution. In general therefore, bioremediation of soil and water are extremely difficult and expensive tasks. The carbo sugars described herein provide a viable alternative for the bioremediation of environmental contaminants.

In one aspect, the carbo sugars described herein can be used to degrease water mixed with petroleum oil or another fatty substance. In another aspect, the carbo sugars described herein can be used to degrease a surface coated with petroleum oil or another fatty substance. The term "degrease" as used herein is the ability of the carbo sugars described herein to remove petroleum oil or fatty substances from water or a surface. In one aspect, the carbo sugar removes up to 50%, up to 60%, up to 70%, up to 80%, up to 90%, up to 95%, or up to 99% of the petroleum oil or fatty substances from water or the surface. In one aspect, biological devices expressing lipase can catalyze the hydrolysis of fatty substances contaminating water or a surface.

In one aspect, the carbo sugar as an aqueous solution is added to the petroleum-containing water. In one aspect, the concentration of the carbo sugar is 0.1, 0.5%, 0.75%, 1%, 2%, 3%, 4%, or 5% by weight, where any value can be the lower and upper end-point of a range (e.g., 0.1 to 3%, 0.5 to 2%, etc.). In another aspect, the volume ratio of petroleum-containing water to carbo sugar (1% concentration) is 1:1, 1:2, 1:3, 1:4, or 1:5, where any ratio can be the lower and upper end-point of a range (e.g., 1:1 to 1:4, 1:2 to 1:3, etc.). As demonstrated in the examples, the carbo sugar when added to the petroleum-containing water separates the oil from the water, which then can be easily removed from the water using techniques known in the art.

In one aspect, the water to be decontaminated is from the ocean, ground water, a lake, a river, a stream, or another natural water supply. In an alternative aspect, the water to be treated is waste water from a petroleum drilling operation or is from a reservoir or municipal water supply.

In another aspect, the surface to be degreased is a natural surface such as stone, wood, compacted dirt, animal fur or feathers or skin, or the like. In still another aspect, the surface to be degreased is a manmade surface such as, for example, glass or glassware, metal, concrete, asphalt, a building, a vehicle, oil drilling equipment, a road or path, a household object, or the like. In a further aspect, the fatty substance to be removed from the water or surface is petroleum or petroleum derived, is a plant fat or animal fat such as, for example, food waste or cooking oil. In the food industry, the carbo sugars produced herein can be used to degrease surfaces coated with cooking oils and fats. For example, frying pans and other utensils coated with cooking oils and grease can be degreased with the carbo sugars. In other aspects, grease traps for collecting and storing cooking oil and grease can be degreased with the carbo sugars herein.

In another aspect, the carbo sugars produced herein can be used to produce polyurethane compositions that have numerous applications.

In one aspect, the polyurethane composition is produced by:
a. admixing the carbo sugar produced herein and a natural oil polyol to produce a first admixture; and
b. reacting the first admixture with a polyisocyanate to produce the polyurethane composition.

A "natural oil" as used herein is any oil extracted from a living organism. In one aspect, the living organism is a plant or alga. In a further aspect, the plant is the castor bean or castor oil plant (*Ricinus communis*). In another aspect, the living organism is an animal. In an alternative aspect, the living organism is a fungus. Natural oils can additionally contain triglycerides, fatty acids, fatty acid esters, sterols, isoprenoid or terpenoid compounds, alkaloids, phenols, and other metabolites.

"Natural oil polyols" are compounds derived from or present in natural oils that include at least one free hydroxyl group. A natural oil polyol may be naturally occurring, as with the ricinoleic acid in castor oil, or it may be chemically synthesized from an oil or fat containing one or more carbon-carbon double bonds. In one aspect, a natural fatty acid or triglyceride containing a carbon-carbon double bond is subjected to ozonolysis to cleave the double bond, followed by treatment with another molecule such as, for example, ethylene glycol, to form an alcohol. In another aspect, a natural fatty acid or triglyceride containing a carbon-carbon double bond can be epoxidized and treated with a nucleophile to generate an alcohol. In still another aspect, a natural fatty acid or triglyceride containing a carbon-carbon double bond can be formylated in the presence of carbon monoxide and hydrogen gas, followed by hydrogenation to generate a hydroxyl group. Other methods of producing natural oil polyols are also contemplated. Natural oils can be used as extracted or can optionally be purified. In one aspect, the natural oil polyol is or is derived from soy, a chemically-modified vegetable oil, a carbohydrate, lignin, cork, cashew nutshell liquid, *Lesquerella* oil, or a combination thereof. In one aspect, the natural oil polyol is castor oil. In another aspect, the natural oil polyol is ricinoleic acid. In still another aspect, the natural oil polyol is coriolic acid or a chemically-modified fatty acid.

"Castor oil" can optionally be extracted from the seeds of the castor oil plant. The primary component of castor oil is ricinoleic acid; minor components include oleic acid, linoleic acid, linolenic acid, stearic acid, palmitic acid, dihydroxystearic acid, and other trace fatty acids.

In one aspect, the natural polyol can include one or more hydroxy fatty acids, which is defined herein as a fatty acid having at least at least one free hydroxyl group. The hydroxy fatty acid has the general formula R'C(O)OH, wherein R' is a saturated or unsaturated hydrocarbon chain having from 10 to 25 carbon atoms, and at least one hydroxyl group is covalently attached to a carbon atom of the hydrocarbon chain. The hydrocarbon can be linear or branched. In the case when the hydrocarbon is unsaturated, the hydrocarbon can have one carbon-carbon double bond or multiple carbon-carbon double bonds. Examples of monohydroxy fatty acids (i.e., one hydroxyl group present on the fatty acid) include, but are not limited to, hydroxynervonic acid, cerebronic acid, 10-hydroxy-20 decenoic acid, hydrox-2-decenoic acid 10-phosphate, strophantus acid, lesquerolic acid, densipolic acid, auricolic acid, α-dimorphecolic acid, kamlolenic acid, 8-hydroxyoctadeca-9,11-diynoic acid, 8-hydroxyoctadeca-17-en-9.11-diynoic acid (isanolic), or 8-hydroxyoctadeca-13.17-dien-9.11-diynoic acid. Examples of polyhydroxy fatty acids (i.e., two or more hydroxyl groups) include, but are not limited to, axillarenic acid, tetrapedic acids, byrsonic acid, 9,10-dihydroxyoctadecanoic acid, phaseolic acid, phloionolic acid, Resolvin D1, 10,17S-docosatriene, or Resolvin E1. The hydroxy fatty acids can be sued as is in the natural oil (e.g., castor oil), isolated from a natural oil, or synthesized accordingly.

In certain aspects, chitosan can be used to produce the polyurethane compositions described herein, where it is admixed with the carbo sugar and a natural oil polyol to produce the first admixture. "Chitosan" as used herein is a linear polymer of randomly-distributed GlcN and NAG residues. Chitosan may be obtained from chitin using alkali extraction or by any other technique known in the art. In one aspect, chitin is "deacetylated" using alkali to produce chitosan. In one aspect, deacetylation can remove some or all of the acetyl groups from the NAG residues of chitin. In one aspect, the chitin is from about 50% to about 100% acetylated. In a further aspect, the chitin is from about 50% to about 80% acetylated, 60% to about 80% acetylated, or 70% to about 80% acetylated. In a still further aspect, the chitosan is about 50% acetylated, about 60% acetylated, or about 77% acetylated. The molecular weight of the chitosan can vary. For example, the chitosan can contain about 3, 4, 5, 6, 7, 8, 9, 10, 11, 12, 13, 14, 15, 16, 17, 18, 19, 20, or any range thereof, of GlcN and/or NAG units. In another aspect, the chitosan can include 5 to 7 GlcN and/or NAG units. In certain aspects, the inclusion of chitosan can impart antimicrobial properties to the polyurethane composition.

In certain aspects, a surfactant can be used to produce the polyurethane compositions described herein, where it is admixed with the carbo sugar and a natural oil polyol to produce the first admixture. A "surfactant" is an organic compound that may be derived from a natural product, or may result from chemical modification of a natural product, or may be completely chemically synthesized. Surfactants typically contain hydrophilic head groups and hydrophobic tails. In one aspect, the head group is anionic, cationic, non-ionic, or zwitterionic. In another aspect, the tail is composed of a hydrocarbon or a glucoside. Surfactants alter the surface tension of liquids and may form micelles or bilayers in aqueous solution. Many applications of surfactants are known in the art. Surfactants are, for example, commonly employed as emulsifiers, detergents, wetting agents, and in other related uses.

Numerous cationic surfactants can be used in the compositions described herein. In one aspect, the cationic surfactant can be a quaternary ammonium salt.

Numerous zwitterionic surfactants can be used in the compositions described herein. In one aspect, the zwitterionic surfactant can be a lecithin such as soy lecithin; in another aspect, the zwitterionic surfactant can be a hydroxysultaine, a betaine, a sulfobetaine, or a mixture thereof. Among betaines, surfactants may be selected from the group comprising high alkyl betaines such as cetyl dimethyl carboxymethyl betaine, cocamidopropyl betaine, cocobetaine, coco dimethyl carboxymethyl betaine, lauryl amidopropyl betaine, lauryl bis-(2-hydroxyethyl) carboxymethyl betaine, lauryl bis-(2-hydroxypropyl)alpha-carboxyethyl betaine, lauryl dimethyl alphacarboxyethyl betaine, lauryl dimethyl carboxymethyl betaine, oleyl betaine, oleyl dimethyl gamma-carboxypropyl betaine, stearyl bis-(2-hydroxypropyl) carboxymethyl betaine, and mixtures thereof. Among sulfobetaines, surfactants may be selected from the group comprising coco dimethyl sulfopropyl betaine, lauryl bis-(2-hydroxyethyl) sulfopropyl betaine, lauryl dimethyl sulfoethyl betaine, stearyl dimethyl sulfopropyl betaine, and mixtures thereof. Amidobetaines and amidosulfobetaines are also contemplated.

Numerous nonionic surfactants can be used in the compositions described herein. Nonionic surfactants useful in the compositions described herein include alkoxylated fatty acid esters, alkyl glucosides, alkyl polyglucosides, amine oxides, alcohol ethoxylates, cocoamine oxide, glyceryl monohydroxystearate, glyceryl stearate, hydroxy stearic acid, lauramine oxide, laureth-2, polyhydroxy fatty acid amides, polyoxyalkylene stearates, propylene glycol stearate, sorbitan monostearate, sucrose cocoate, sucrose esters, sucrose laurate, steareth-2, PEG-40 hydrogenated castor oil, and mixtures thereof. Preferred nonionic surfactants include those based on polyethoxylated sorbitan and oleic acid such as, for example, polysorbate 80 and polysorbate 20, both of which are available under a variety of trade names.

Further nonionic surfactants contemplated herein include, in one aspect, the nonionic surfactants include the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij® surfactants from ICI. Tergitol™ 15-S Surfactants include $C_{11}$-$C_{15}$ secondary alcohol polyethylene glycol ethers. Brij™97 surfactant is Polyoxyethylene(10) oleyl ether; Brij™58 surfactant is polyoxyethylene (20) cetyl ether; and Brij™ 76 surfactant is polyoxyethylene (10) stearyl ether.

In another aspect, a useful class of nonionic surfactants includes the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy)ethanols. Igepal™ CA surfactants include octylphenoxy poly(ethyleneoxy)ethanols. Still another useful class of hydrocarbon nonionic surfactants includes block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. In other aspects, the nonionic surfactants include sorbitan fatty acid esters, polyoxyethylene sorbitan fatty acid esters and polyoxyethylene stearates having HLBs of about 6 to about 19, about 9 to about 18, and about 10 to about 16. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates. In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Numerous anionic surfactants can be used herein. In one aspect, the anionic surfactant can be selected from the group comprising alcohol phosphates and phosphonates, alkyl alkoxy carboxylates, alkyl aryl sulfates, alkyl aryl sulfonates, alkyl carboxylates, alkyl ether carboxylates, alkyl ether sulfates, alkyl ether sulfonates, alkyl phosphates, alkyl polyethoxy carboxylates, alkyl polyglucosides, alkyl polyglucoside sulfates, alkyl polyglucoside sulfonates, alkyl succinamates, alkyl sulfates, alkyl sulfonates, aryl sulfates, aryl sulfonates, fatty taurides, isethionates, N-acyl taurates, nonoxynol phosphates, octoxynol phosphates, sarcosinates, sulfated fatty acid esters, taurates, and mixtures thereof. Useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8) N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt. Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the trade name AEROSOL OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and/or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates. Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340KL from Clariant Corp., as well as PPG-5 cetyl 10 phosphate available under the trade designation CRODAPHOS™ SG from Croda Inc., Parsipanny, N.J. Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, a surfactant is chosen based on its ability to form a stable emulsion containing an acidic aqueous solution of a polysaccharide and a natural oil polyol. In a further aspect, the concentration of surfactant can be from 0.001% to 1% (v/v), or is about 0.001%, 0.005%, 0.01%, 0.05%, 0.1%, 0.35%, 0.5%, or 1% (v/v) with respect to the final emulsion volume. In another aspect, 0.35% of polysorbate 80 is used. In a further aspect, emulsion formation can be evaluated as function of stirring time (e.g., about 1 minute, about 2 minutes, about 4 minutes, about 6 minutes, about 8 minutes, or about 10 minutes) and/or stirring speed (e.g., about 2,000 rpm, about 5,000 rpm, about 10,000 rpm, or about 20,000 rpm).

The order in which the carbo sugar and natural oil polyol can be admixed with one another to produce the first admixture can vary. In one aspect, the natural oil polyol can be added to a solution of the carbo sugar. In one aspect, the natural oil polyol is added over time (e.g., 2 minutes, 4 minutes, 5 minutes, 6 minutes, 8 minutes, or 10 minutes) with stirring (2,000 rpm, 5,000 rpm, 10,000 rpm, or 20,000 rpm) to create a final admixture that also incorporates the carbo sugar. In one aspect, the natural oil polyol is castor oil and stirring is conducted at 10,000 rpm for 5 minutes.

In one aspect, wherein the carbo sugar is from 0.1 to 1% by weight of the first admixture. In another aspect, the amount of carbo sugar is 0.1, 0.2, 0.3, 0.4, 0.5, 0.6, 0.7, 0.8, 0.9, or 1 wt % of the first admixture, where any value can be a lower or upper endpoint of a range (e.g., 0.2 to 0.7, etc.). In another aspect, the carbo sugar can be prepared and used as a solution. In one aspect, the carbo sugar is an aqueous solution of 1 to 5% w/v, where the first admixture includes 20% to 80% (v/v) of the aqueous solution of carbo sugar.

In one aspect, the natural oil polyol is from 20% to 80% (v/v) of the first admixture. In another aspect, the natural oil polyol is from 20%, 25%, 30%, 35%, 40%, 45%, 50%, 55%, 60%, 65%, 70%, 75%, or 80% (v/v) of the first admixture, where any value can be a lower or upper endpoint of a range (e.g., 40% to 60%, etc.).

Prior to the addition of the polyisocyanate, additional components can be added to the first admixture of carbo sugar and natural oil polyol. In one aspect, a catalyst can be added to the first admixture. A "catalyst" as used herein is any substance that can increase the rate of a chemical reaction. In one aspect, the catalyst is not consumed in the reaction. A single molecule of a catalyst can assist with multiple chemical reactions. Catalysts useful herein include, but are not limited to, tertiary amines such as dimethylethanolamine (DMAE), triethylenediamine (DABCO), 3-aminopropyldimethylamine (DMAPA), dimethylcyclohexylamine (DMCHA); compounds containing hydroxyl groups or secondary amines such as, for example, propylene glycol; metallic compounds including metal carboxylates such as, for example, dibutyltin dilaurate (DBTDL) as well as mercury, lead, bismuth, and zinc carboxylates; and other alkyl tin carboxylates, oxides, and mercaptides. In one aspect, the catalyst is added to an emulsion containing the carbo sugar and natural oil polyol at from about 0.05% to about 2% (v/v) with respect to the volume of the emulsion. In another aspect, about 0.05%, 0.1%, 0.15%, 0.2%, 0.25%, 0.4%, 0.6%, 0.7%, 0.8%, 1%, 1.2%, 1.5%, or 2% catalyst is used. In some aspects, a combination of catalysts is used. In one aspect, 0.5% (v/v) dibutyltin dilaurate and 1% (v/v) dimethylethanolamine were used in combination. In a further aspect, stirring is used to incorporate the catalyst throughout an emulsion containing the carbo sugar and natural oil polyol. In one aspect, different stirring times (e.g. about 1 minute, about 2 minutes, about 3 minutes, about 4 minutes, about 5 minutes, about 8 minutes, or about 10 minutes) and different stirring speeds (about 100 rpm, about 200 rpm, about 300 rpm, about 400 rpm, about 500 rpm, about 600 rpm, or about 700 rpm) are evaluated to determine the minimum stirring time and speed required to fully incorporate the catalyst into the emulsion. In one aspect, the emulsion and added catalyst are stirred at 300 rpm for 3 minutes.

In another aspect, a clay can be added to the first admixture. "Clay" and "clay minerals" as used herein refer to hydrous aluminum phylosilicates. Clays can optionally include oxides and/or chelates of other metals and semimetals such as, for example, silicon, iron, calcium, magnesium, sodium, potassium, and other alkali and alkaline earth metals. "Bentonite" is a category of impure clay that can consist of montmorillonite, kaolinite, and other species; and that can include potassium, sodium, calcium, aluminum, as well as other metals. "Zeolites" are microporous aluminosilicates that can accommodate a variety of cations, including, but not limited to, sodium, potassium, calcium, and magnesium. The cations in zeolites can be exchanged in aqueous solutions. Clays, bentonites, and zeolites can be used as sources of trace oxides and/or ions in the practice of the present invention. An "oxide" as used herein refers to a molecule, a network solid, or an ionic compound containing at least one oxygen atom and one other element. In one aspect, clays, bentonites, and zeolites contain chelated metal and semimetal ions. Not wishing to be bound by theory, the inclusion of the clay can be used to vary the pore size of the final biofoam product produced.

In one aspect, a metal or semimetal oxide or a chelated metal ion can be incorporated into the first admixture. In one aspect, the metal or semimetal oxide includes, for example, $Al_2O_3$, $Fe_2O_3$, MgO, CaO, $Na_2O$, $K_2O$, $SiO_2$, or a combination thereof. In this aspect, the metal or semimetal oxide can be introduced into the polyurethane compositions as a pure compound. In an alternative aspect, ions such as, for example, aluminum, iron (III), magnesium, calcium, sodium, potassium, silicon, and combinations thereof, can be incorporated into the polyurethane compositions described herein through the inclusion of clays or clay minerals. In one aspect, the metal or semimetal oxides or chelated metals are incorporated at concentrations of from about 0.02 nM to about 1.2 mM, or at 0.2 nM, 0.04 nM, 0.06 nM, 0.08 nM, 0.1 nM, 0.15 nM, 0.2 nM, 0.25 nM, 0.3 nM, 0.35 nM, 0.4 nM, 0.45 nM, 0.5 nM, 0.55 nM, 0.2 mM, 0.4 mM, 0.6 mM, 0.8 mM, or 1.2 mM.

In another aspect, one or more water-soluble metal salts can be incorporated into the first admixture. In one aspect, the water-soluble metal salts can include, for example, gallium (III) nitrate hydrate, zinc sulfate, zinc acetate, or a combination thereof. In one aspect, 50 mg/L of gallium (III) nitrate hydrate is incorporated into the emulsion containing the carbo sugar and natural oil polyol. In another aspect, 100 mg/L of zinc sulfate is incorporated into the emulsion containing the carbo sugar and natural oil polyol.

After preparation of the first admixture as described above, a polyisocyanate is added to the first admixture. "Polyisocyanates" as used herein are compounds with two or more —N=C=O groups. In one aspect, the polyisocyanate is an aliphatic diisocyanate, a cycloaliphatic diisocyanate, an aromatic diisocyanate, or an isomer thereof. In another aspect, the isocyanate or polyisocyanate is 2,4-toluenediisocyanate, 2,6-toluenediisocyanate, 4,4'-methylene diphenyl diisocyanate (MDI), 4,4'-methylenebis(cyclohexylisocyanate) (H12-MDI), 1-isocyanato-3-isocyanatomethyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, xylylene diisocyanate, dichlorohexamethylene diisocyanate, dicyclohexyl-4,4'-diisocyanate, 1-methyl-2,4-diisocyanato-cyclohexane, 1-methyl-2,6-diisocyanato-cyclohexane, naphthalene-1,5-diisocyanate, p-phenylendiisocyanate, tetramethyl-xylylenediisocyanate (TMXDI), or any combination thereof. The isocyanate or polyisocyanate can exist as one or more structural isomers. Alternatively, the isocyanate or polyisocyanate can be a dimer, trimer, or oligomer. In other aspects, the isocyanate or polyisocyanate can exist as one or more positional isomers. For example, the polyisocyanate can be a mixture of 2,4-toluenediisocyanate and 2,6-toluenediisocyanate. In a further aspect, the polyisocyanate can be a 65:35 mixture of 2,4-TDI and 2,6-TDI (i.e., TDI 65). In a different aspect, the polyisocyanate can be an 80:20 mixture of 2,4-TDI and 2,6-TDI (i.e., TDI 80). In an alternative aspect, the polyisocyanate is a modified MDI or polyphenylmethane polyisocyanate such as one of those sold by Yantai Wanhua Polyurethanes Co. under the trade name WANNATE®.

In one aspect, the polyisocyanate is added to the first admixture at different ratios such as, for example, about 1:1, about 1:2, about 1:3, about 1:4, about 1:5, about 1:6, about 1:7, or about 1:8 with respect to the total emulsion volume, or any range thereof (e.g., 1: to 1:8, 1:3 to 1:5, etc.). In this aspect, polymerization reactions can then be carried out. Different reaction times (e.g. 8 minutes, 10 minutes, 12 minutes, 15 minutes, or 20 minutes) and stirring speeds (e.g., 500 rpm, 600 rpm, 700 rpm, 800 rpm, 900 rpm, or 1000 rpm) can be evaluated to determine the optimum reaction time and stirring speed. In one aspect, the first admixture is admixed with the polyisocyanate for 10 minutes at 500 rpm. In another aspect, the reaction is conducted at room temperature.

Upon admixing the components in the first admixture with the polyisocyanate, isocyanate-reactive functional groups present on the carbo sugar and/or natural oil polyol react with the isocyanate groups on the polyisocyanate to produce a polyurethane. Here, a polymer composed of organic residues joined by urethane linkages is produced. Although the components in the first admixture include hydroxyl groups, other components may be present that include other isocyanate-reactive functional groups an amine groups, a thiol groups, or other nucleophilic groups capable of reacting with isocyanate groups.

The amount of the carbo sugar present in the final biofoam product can vary. In one the amount of carbo sugar present in the biofoam is from 0.005% to 0.1% by weight of the biofoam. In another aspect, the amount of carbo sugar present in the biofoam is from 0.005%, 0.01%, 0.02%, 0.03%, 0.04%, 0.05%, 0.06%, 0.07%, 0.08%, 0.09%, or 0.1% by weight of the biofoam, where any value can be a lower and upper end-point of a range (e.g., 0.01% to 0.05%). When used to prepare the biofoams, the carbo sugar can be prepared as a stock solution. For example, the carbo sugar in powder form (0.05 g, 0.1 g, 0.2 g, 0.3 g, 0.4 g, 0.5 g, 0.6 g, 0.7 g, 0.8 g, 0.9 g or 1 g) can be added to water (100 mL to 1 L) to produce a stock solution. The pH of the stock solution can be adjusted accordingly. In one aspect, the pH of the carbo sugar stock solution is from 1 to 5, 1.5 to 4, or 2 to 3.

The polyurethane compositions produced herein can be used to produce biofoams that have numerous applications. The term "biofoam" as used herein is any substance formed when pockets of gas have been trapped in a solid or liquid. In one aspect, the biofoams produced herein can exist as an emulsion or dispersion at room temperature. In other aspects, he biofoams produced herein are solid materials at room temperature.

The selection and amounts of reactants as well as processing conditions will determine the physical state of the biofoams. For example, the density of the biofoam can be modulated by varying the relative amount of the components used to produce the biofoam. In one aspect, the density of the biofoam is from 0.1 to 05 $g/cm^3$. In another aspect, the density of the biofoam is from 0.1, 0.15, 0.2, 0.25, 0.3, 0.35, 0.4, 0.45, or 05 $g/cm^3$, where any value can be a lower or upper end-point of a range (e.g., 0.1 to 0.3 $g/cm^3$.

In one aspect, when the polyisocyanate is admixed with the first admixture, a solid biofoam is produced. In one aspect, the biofoams produced herein are solid, rigid materials that have numerous applications in the construction and building industry. The polyurethane compositions produced herein can be poured into a mold of any desired shape. If necessary, the mold containing the polyurethane composition can be placed in an oven to remove residual solvent and produce the final biofoam.

In other aspects, one or more blowing agents can be incorporated into the polyurethane compositions to produce the biofoams. A blowing agent can be physical or chemical in nature. A "physical blowing agent" is a gas or low boiling point liquid which expands due to heat generated by the polyurethane-forming reaction, thus forming bubbles and creating foam. A "chemical blowing agent" is a compound or substance that reacts to form a gas. In one aspect, the blowing agent is a physical blowing agent. Physical blowing agents include compounds such as, for example, hydrofluorocarbons (HFCs), hydrocarbons (HCs), hydrofluoroolefins, liquid $CO_2$, and other low boiling point liquids. In one aspect, the physical blowing agent is HFC-134a (1,1,1,2-tetrafluoroethane), HFC-245fa (pentafluoropropane), HFC-365mfc (1,1,1,3,3-pentafluorobutane), HFC-152a (1,1-difluoroethane), formic acid, methyl formate, HFO-1234ze (1,3,3,3-tetrafluoropropene), cyclopentane, n-pentane, iso-pentane, iso-butane, acetone, dichloromethane, or a mixture thereof. In another aspect, the blowing agent is a chemical blowing agent. In one aspect, the chemical blowing agent is carbon dioxide produced by the reaction of isocyanate groups with water. In a further aspect, both chemical and physical blowing agents can be used.

In other aspects, the biofoams include additional additives not already described above such as, for example, flame retardants, color additives, release agents, biocides, other additives, or a combination thereof. The additional components can be admixed with a dispersion or emulsion of polyurethane composition in order incorporate the additives throughout the biofoam. In the alternative, the additives can be applied to the surface of the solid biofoam.

In another aspect, after the preparation of the biofoam, the biofoam can contain residual solvent (e.g., water). In certain aspects, it is desirable to remove all or substantially all (e.g., greater than 70%, greater than 80%, greater than 90%, greater than 95%, greater than 99%, or 100%) of the solvent in the biofoam. In one aspect, drying of the biofoams can be accomplished in an oven at about 20° C., 30° C., 40° C., 50° C., 60° C., or about 70° C. In one aspect, the biofoams are dried in an oven at 50° C. In a further aspect, the biofoams can be dried for from about 0.5 to about 100 hours, or for about 72 hours. In one aspect, removal of water from biofoams is assessed by periodically removing the biofoams from the oven and weighing them. When the biofoams have the same weight at, for example, at least 2 or 3 successive weighings separated by several hours, the biofoams can be considered to be dry and can be removed from the oven.

In one aspect, the biofoams disclosed herein can be used in the construction industry in applications such as, for example, extruded building materials of any size (e.g., 2 by 4, etc.), alternatives to gypsum wall boarding, alternatives to gypsum wall "mud," substitutes for wall paneling, substitutes for 4 by 8 plywood sheets, rigid precast structures such as columns, as a substitute for Gunnite in swimming pools, bulletproofing for walls in homes, insulation, poured flooring, roofing tiles, I-beams, trusses, rebar, and the like. In an alternative aspect, the biofoams disclosed herein can be used in the transportation industry in applications such as, for example, as a substitute for fiberglass in boat hulls or bulletproofing for cars. In still another aspect, additional uses for the biofoams disclosed herein are contemplated including, but not limited to, ammunition (e.g., pelletized biofoams as shotgun shell shot or rifle ammunition slugs), silverware or cutlery, lead-free microwave safe dishware, conical antenna dishes, aircraft drone propellers, and related applications.

In another aspect, the biofoams disclosed herein can be used in the medical industry. In one aspect, the biofoam can be used where it is desirable to reduce or minimize blunt force or trauma to a subject. For example, the polyurethane composition can be injected between the skin of the subject and a cast to produce a biofoam that can further prevent any applied force to the broken bone of the subject. In certain aspects, the polyurethane composition can include antimicrobial agents in order to prevent odor. In other aspects, the biofoams can be used to manufacture casts, braces, helmets, or any other medical article that can be used to reduce or prevent applied force or trauma to a subject.

In other aspects, the polyurethane compositions described herein can be used as adhesives. For example, the polyurethane composition can be in a sufficient amount of solvent so that is can readily be applied to the surface of a substrate (e.g., spray coating, dipping, brushing). Upon removal of the solvent a biofoam is produced, which results in the formation of a strong bond between to substrates. In other aspects, the polyurethane compositions can be used to seal cracks and holes. Here, the polyurethane composition is sprayed in a hole or crack then forms a biofoam.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

Preparation of DNA Construct for Production of Carbo Sugars

The following DNA sequences were synthesized: a gene for expressing galactomannan galactosyltransferase gene from *Cyamopsis tetragonoloba* (SEQ ID NO. 4), a gene for expressing cellulose synthase from *Pyropia yezoensis* (SEQ ID NO. 1), a gene for expressing lipase from *Micrococcus* sp. HL-2003 (SEQ ID NO. 9), and yellow fluorescent reporter protein (SEQ ID NO. 7). Lipase was included in some constructs and was functional at any position in the construct. However, a position 5' of the gene for expressing cellulose synthase was preferable when the lipase gene was included.

A pYES2 plasmid vector was used to assemble a DNA construct, which also contained a T7 promoter, and a terminator. The cloning of the DNA construct into the biological devices was performed as follows. Overlapping oligonucleotides were amplified by polymerase chain reaction. These oligonucleotides were then ligated using standard protocols to form an insert. The insert was cloned into cloning vector pBSK. Individual clones were sequenced and site-directed mutagenesis was used to correct mutations in the clones. Following site-directed mutagenesis, clones were sequenced again to verify the DNA sequence of the insert. A pYES2 plasmid was then digested with HindIII restriction enzyme according to directions provided by the enzyme's supplier (Promega). The complete insert, containing HindIII recognition sites on each end, was then excised from the cloning vector and ligated into the pYES2 plasmid using the protocol described below. Successful construction of the insert and ligation of the insert into the plasmid were confirmed using gel electrophoresis. Backbone plasmids at different ratios ranging from 1:1, 1:2, 1:3, 1:4, and up to 1:5 were evaluated.

In some instances, pETDuet-1 plasmids (Novagen, Inc.) were used in competent *Escherichia coli* cells (BL21(DE3), Novagen, Inc.)

Ligation of the insert occurred in one pot and was carried out using a kit and enzymes from Promega (Madison, Wis.). A 1:2 molar ratio of vector/insert was used for most ligation reactions; a typical ligation reaction used 100-200 ng of vector DNA. To this mixture were added 8 µL of T4 DNA ligase and 124 of ligase buffer. In some reactions, the ligation mixture was incubated at room temperature for 5 minutes. In other reactions, the ligation mixture was introduced into an electromagnetic chamber for 15 minutes.

Figure 4:
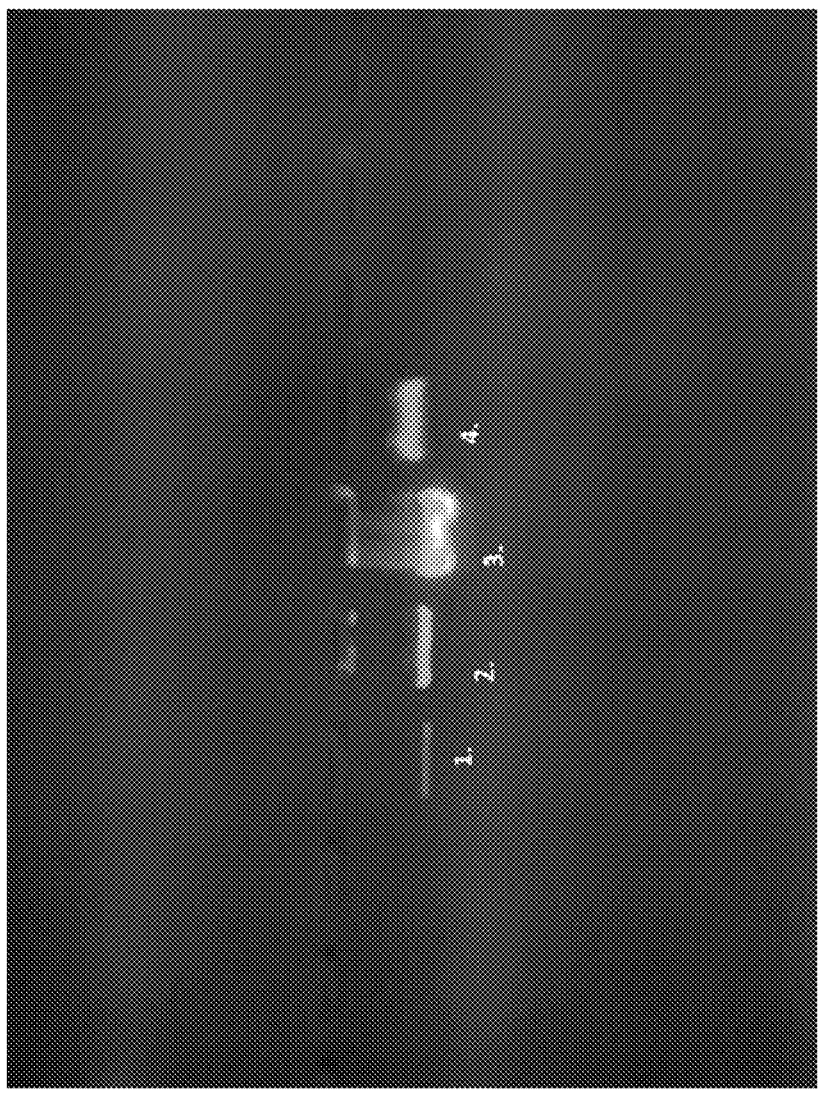
FIG. 4 is a photograph of DNA fragments that have been separated by gel electrophoresis. Lane 1 is the gene for yellow fluorescent reporter protein (0.878 kb), lane 2 is the gene for cellulose synthase (2.3 kb), lane 3 is purified galactomannan galactosyltransferase (1.23 kb), and lane 4 is the final ligation of these three genes in a pYES2 plasmid (10.3 kb). Samples in all lanes were purified prior to loading in the gel. DNA in lanes 1, 2, and 3 was obtained from digesting the ligated plasmid.
Figure 5:
FIG. 5 shows Petri dishes containing colonies of a negative control (competent yeast with no added plasmid). After undergoing a transformation protocol wherein nuclease-free water was added instead of plasmid, cell cultures were incubated overnight at 30° C. and diluted in two stages to determine the optimum concentration for further experiments. Colonies are growing in yeast malt medium with added ampicillin and are shown after 30 h of incubation. The left plate was inoculated with a 10× dilution of the negative control yeast culture and contains an uncountable number of colonies. The right plate was inoculated with a 1000× dilution of the negative control yeast culture and contains approximately 120 colonies.
Figure 6:
FIG. 6 shows Petri dishes containing colonies of a positive control (competent yeast with unmodified pYES2 plasmid added). After undergoing a transformation protocol wherein unmodified pYES2 plasmid was added, cell cultures were incubated overnight at 30° C. and diluted in two stages to determine the optimum concentration for further experiments. Colonies are growing in yeast malt medium with added ampicillin and are shown after 30 h of incubation. The left plate was inoculated with a 10× dilution of the positive control yeast culture and contains an uncountable number of colonies. The right plate was inoculated with a 1000× dilution of the positive control yeast culture and contains approximately 200 colonies.
Figure 7:
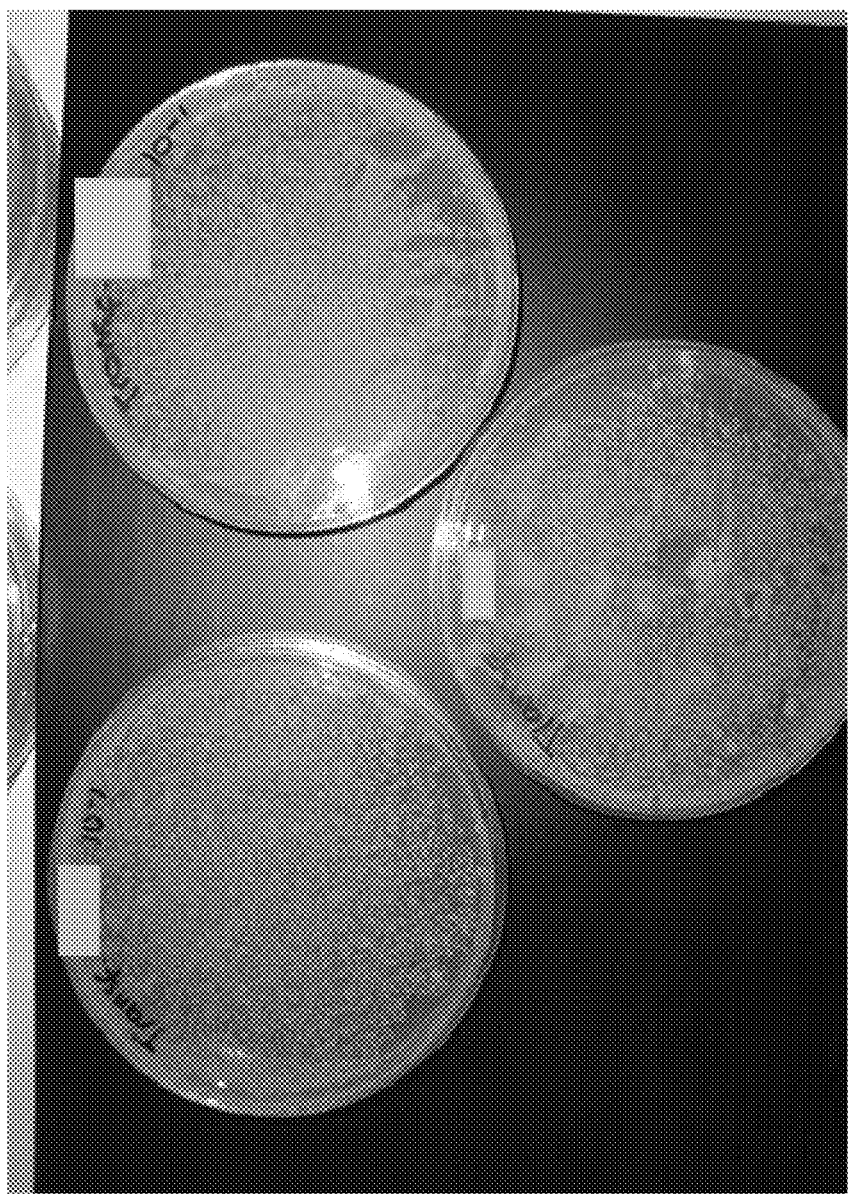
FIG. 7 shows Petri dishes containing colonies of yeast transformed with a constructed plasmid vector. After undergoing a transformation protocol wherein pYES2 plasmid modified with the DNA construct described herein was added, cell cultures were incubated overnight at 30° C. and diluted in two stages to determine the optimum concentration for further experiments. Colonies are growing in yeast malt medium with added ampicillin and are shown after 30 h of incubation. All plates represent a 10× dilution of the transformed yeast culture and contain uncountable numbers of colonies.
Figure 8:
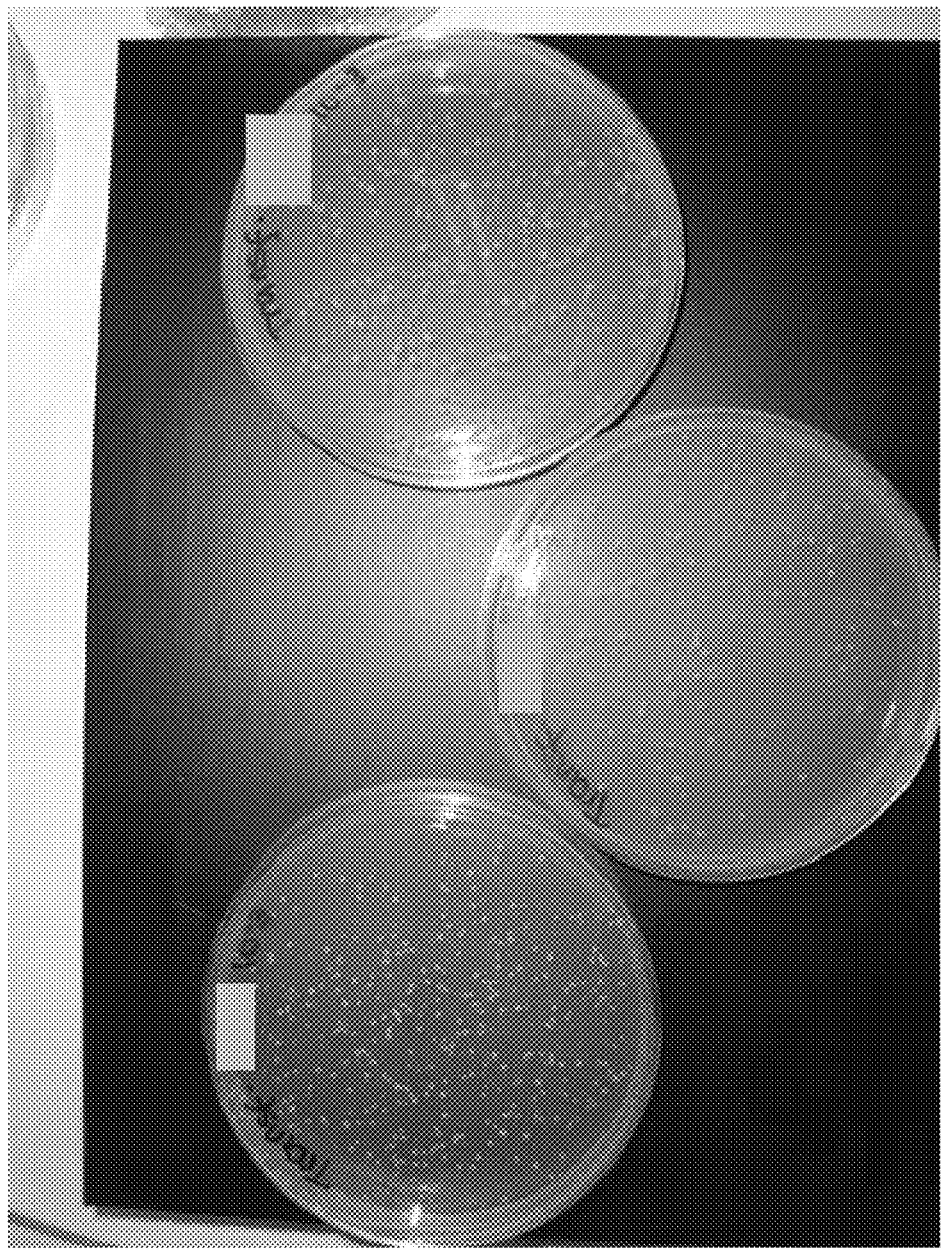
FIG. 8 shows Petri dishes containing colonies of yeast transformed with a constructed plasmid vector. After undergoing a transformation protocol wherein pYES2 plasmid modified with the DNA construct described herein was added, cell cultures were incubated overnight at 30° C. and diluted in two stages to determine the optimum concentration for further experiments. Colonies are growing in yeast malt medium with added ampicillin and are shown after 30 h of incubation. All plates represent a 1000× dilution of the transformed yeast culture and contain an average of 220 colonies.
Figure 9:
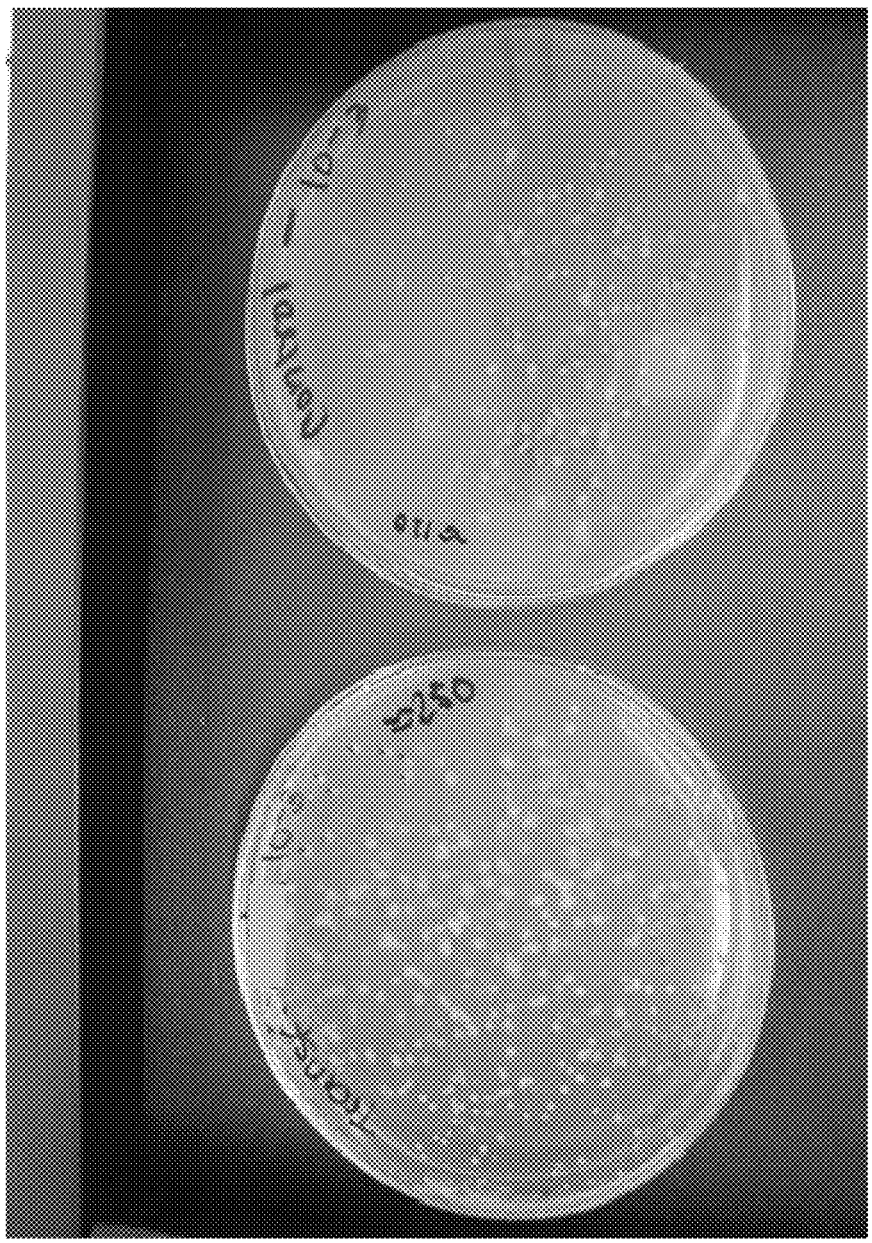
FIG. 9 shows Petri dishes containing colonies of competent yeast. Colonies are growing in yeast malt medium with added ampicillin and are shown after 30 h of incubation. The left plate was inoculated with a 1000× dilution of transformed yeast culture and contains approximately 250 colonies. The right plate was inoculated with untransformed competent yeast and contains approximately 120 colonies.

A schematic of the DNA construct is depicted in FIGS. 3A and 3B. DNA quantification was performed using a UV-Vis spectrophotometer and recording the ratio of the absorbance at 260 nm to the absorbance at 280 nm. Plasmids were then electrophoresed to verify the insertion of genes (FIG. 4), then purified prior to further use. Alternative DNA constructs are depicted in FIGS. 19A and 19B as well as 22A and 22B.

Selection of Microorganisms

Carbo sugars were produced using transfected yeasts (*Saccharomyces cerevisiae*, ATCC® 200892™) and/or bacteria (*Escherichia coli*, ONESHOT® Top10 competent cells from Life Technologies™; DH5α and BL21(DE3) strains were also used for some experiments).

Development of Competent Yeast Cells

Yeast cells were made competent by subjecting them to an electrochemical process adapted from Gietz and Schiestl (*Nature Protocols,* 2007, 2:35-37). Briefly, a single yeast colony was inoculated into 100 mL YPD (yeast extract peptone dextrose) growth media. Yeast was grown overnight on a shaker at 30° C. to $OD_{600}$=1.0. (Acceptable results were obtained with $OD_{600}$ values ranging from 0.6 to 1.8.) Cells were centrifuged at 2,000 rpm in a tabletop centrifuge and resuspended in 10 mL TEL buffer (10 mM Tris-HCl, 1 mM EDTA, 0.1 M LiAc, pH=7.5) and shaken vigorously overnight at room temperature. Cells were again centrifuged and resuspended in 1 mL TEL buffer. Cells prepared in this manner could be stored in the refrigerator for up to one month.

Transformation of Yeast Cells to Produce Carbo Sugar Device

Competent cells were stored in the freezer until needed. Cells were thawed on ice and 100 µL of competent cells in TEL buffer were placed in a sterile 1.5 mL microcentrifuge tube. To this was added 5 µL of a 10 mg/mL solution of salmon sperm DNA (carrier DNA). Transforming DNA (construct depicted in FIGS. 3A and 3B) was added in various amounts. From 1 to 5 µg was sufficient for plasmids from commercial sources, but more DNA was required when transforming yeast with artificial DNA constructs. 10 µL of the DNA device were added to the microcentrifuge tube containing the competent yeast cells and the contents of the tube were mixed. The DNA-yeast suspension was incubated for 30 min at room temperature.

A PLATE solution (consisting of 40% PEG-3350 in 1×TEL buffer) was prepared. 0.7 mL of PLATE solution was added to the DNA-yeast suspension and the contents were mixed thoroughly and incubated for 1 h at room temperature. The mixture was placed in an electromagnetic chamber for 30 minutes. Cells were then heated at 42° C. for 5-10 minutes and 250 µL aliquots were plated on yeast malt agar to which selective growth compounds had been added. Plates were incubated overnight at 30° C.

DNA expression and effectiveness of transformation were determined by fluorescence of the transformed cells expressed in fluorescence units (FSUs) using a 20/20 Luminometer (Promega) according to a protocol provided by the manufacturer. Plasmid DNA extraction, purification, PCR, and gel electrophoresis were also used to confirm transformation. Different transformed devices were obtained. Different types of fluorescent reporter proteins were used (e.g., yellow, red, green, and blue) for all transformed cells and/or constructs. However, the yellow fluorescent protein was preferred. When no fluorescent reporter protein was assembled, no fluorescence was observed.

*S. cerevisiae* cells were subjected to transformation with the modified pYES2 plasmid depicted in FIGS. 3A and 3B and FIGS. 19A and 19B. Transformed yeast cells were incubated for 30 min at 28-30° C. Colonies of transformed yeast cells were selected, their DNA isolated and subjected to PCR amplification. Two control treatments were also carried out: (1) a negative control involving competent yeast and nuclease free water instead of plasmid and (2) a positive control involving competent yeast with unmodified pYES2 plasmid.

Bacterial cells were transformed with the modified pETDuet-1 device depicted in FIGS. 20A and 20B using a standard heat shock protocol. Cells were plated and cultured. Four clones were selected and processed for full-length DNA sequencing. A clone with 100% DNA sequence accuracy for the target sequence was selected for further processing. This clone was used to obtain a high concentration of plasmid construct at the mid-scale plasmid purification level.

Example 1

The carbo sugar device described above (*S. cerevisiae* cells transformed with the modified pYES2 plasmid depicted in FIGS. 3A and 3B) was grown in yeast malt agar with 100 µg/mL ampicillin and incubated for 18 h at 28-30° C. After incubation, colonies were counted and the average number of colonies was determined for each plate (FIGS. 5-9). The average number of colonies per plate for each treatment is provided in Table 3. "Dilution" refers to a dilution of the transformed or control yeast culture prior to plating.

TABLE 3

Number of Colonies Per Treatment, 1000 × Dilution

| Treatment | Number of Colonies |
| --- | --- |
| Transformed Yeast | 220 ± 36.1 |
| Negative Control (Competent Yeast Alone) | 122 ± 7.6 |
| Positive Control (Yeast Transformed with Unmodified Plasmid) | 197 ± 15.3 |

The best colony (in terms of growth) was selected from each plate and was independently transferred into 3 mL yeast malt broth and mixed thoroughly. The $OD_{600}$ was determined. Solutions with different optical densities were tested (0.01, 0.02, 0.05, 0.1, 0.2, etc.); however, solutions having $OD_{600}$ of 0.1 gave the best results. A 1 mL aliquot of this yeast dilution was mixed with 40 mL of yeast malt broth.

Example 2

Figure 10:
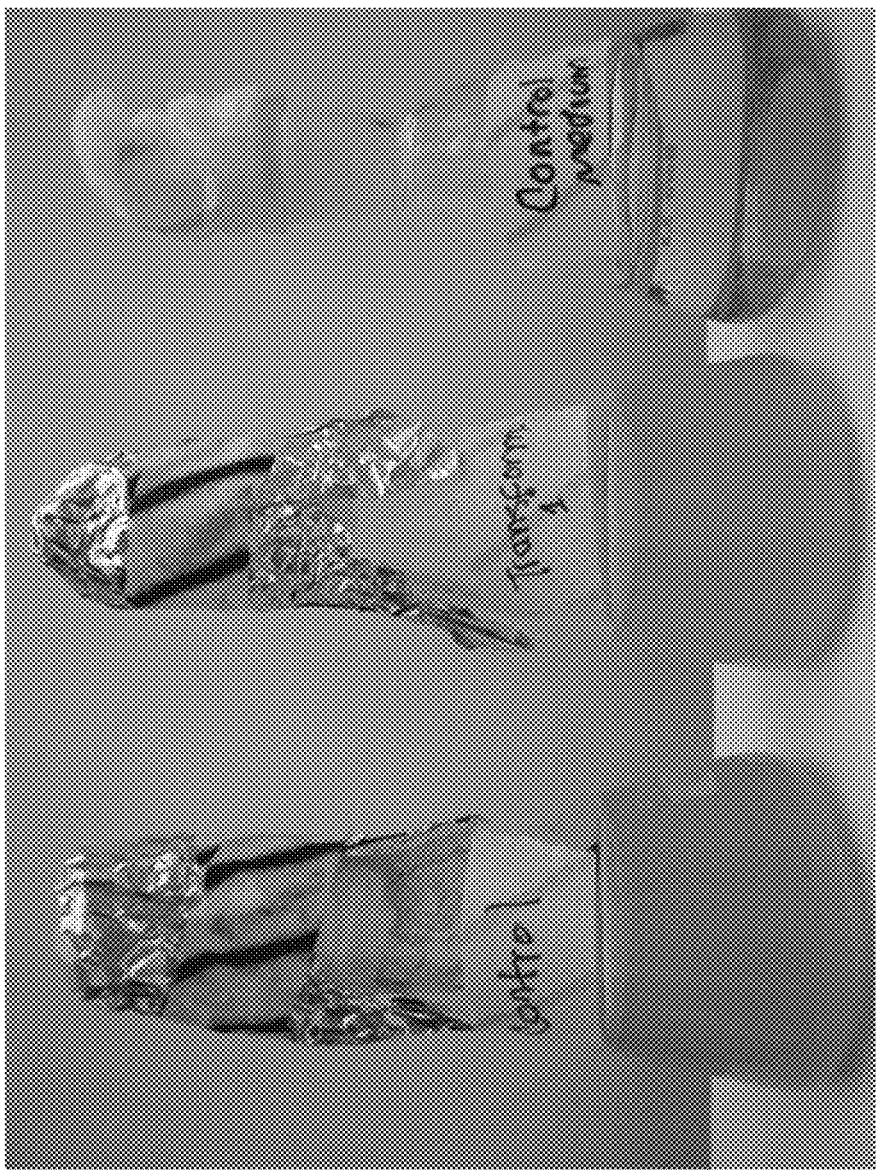
FIG. 10 shows yeast cultures in yeast malt medium with added ampicillin after 18 hours of incubation. Left flask: negative control (untransformed competent yeast). Center flask: transformed yeast. Right flask: Yeast malt liquid medium alone.
Figure 11:
FIG. 11 shows guar samples diluted in 2% KCl. Left flask: Commercial guar diluted in 2% KCl. Center flask: Carbo sugar diluted in 2% KCl. Right flask: Carbo sugar prior to dilution in KCl solution.

The final transfected yeast solution in Example 1 was incubated for 18-22 hours at 28-30° C. After incubation, the culture was tested for carbo sugar production by diluting the yeast culture solution in 2% KCl. 1 part transformed broth (e.g., 10 mL) was diluted with 8 parts KCl (e.g. 80 mL) for a final KCl concentration of 1.7%. This was compared to 0.05% commercial plant guar mixed with 2% KCl. The same reaction occurred in both samples (indicated by a transient clear blue color and a similar appearance, FIGS. 10-11). The pH of the carbo sugar solution was 6.2. Growth of yeast in liquid medium was measured spectrophotometrically after 18 hours of incubation (Table 4).

TABLE 4

Growth of Yeast in Liquid Medium

| Treatment | $OD_{600}$ |
|---|---|
| Transformed Yeast | 2.15 ± 0.037 |
| Negative Control (Competent Yeast Alone) | 1.6 ± 0.207 |

An alternative procedure for growth and induction of the biological devices described herein is as follows: a small sample of transformed yeasts or bacteria were taken into 3-5 mL of an appropriate medium (for example, yeast malt) and grown at 30° C. overnight. 1 mL of incubated solution was diluted in 1 L of appropriate medium containing 2% raffinose (v/v) and incubated at 30° C. for 2-4 hours or until the culture reached an optical density of 0.6-0.8. Galactose sugar (1% v/v) was added to the above culture, which was incubated at 30° C. for at least 48 hours.

Following this culture and induction procedure, the culture was treated with lyticase (240 µL/L) for 24 hours. The culture was centrifuged at 9000 rpm for 15 minutes to obtain a pellet. The pellet was mixed with distilled water (100 mL per 1 g pellet) and sonicated at 30 seconds on, 15 seconds off for 2 minutes at 60% of wavelength amplitude using a QSONICA Sonicator (Newtown, Conn.); this procedure was repeated twice. The supernatant from the above centrifugation was again centrifuged to discard dead cells and/or debris, then filtered using a 0.45 µm pore size filter. Some cultures and extracts were autoclaved and some were used without autoclave treatment. The filtrate was then employed for various applications.

Example 3: Modifying Petroleum Viscosity by Carbo Sugar

The effects of commercial guar versus carbo sugar on petroleum viscosity were tested. 10 mL aliquots of petroleum oil with an API gravity of 20 were mixed with 5 mL of the following individual treatments: (1) 0.05% commercial guar diluted with a 2% KCl solution, (2) carbo sugar produced from transfected yeast produced according to the methods described above in Example 1, (3) carbo sugar from transfected yeast produced according to the methods described above in Example 1 diluted with a 2% KCl solution, (4) a 1:1 mixture of commercial guar and carbo sugar diluted with a 2% KCl solution, and (5) a 1:1 mixture of commercial guar and carbo sugar with an added surfactant. 1% (v/v) of a 2M solution of ethoxylated alcohol was used as the surfactant in most cases. Soy lecithin, polysorbate 20, and polysorbate 80 were also tested at 1% (v/v) concentrations. A control of untreated petroleum oil was also measured.

Oil+treatment samples were prepared by mixing 50 mL of petroleum oil and 25 mL of each treatment (a 2:1 proportion). These were shaken at 120 rpm for 30 min and viscosity was measured. Preliminary results are presented in Table 5.

TABLE 5

Reduction of Petroleum Viscosity Using Carbo Sugar Preparations

| Treatment | API Gravity |
|---|---|
| Control: Pure Oil | 20 |
| Commercial Guar | 24 |
| Carbo Sugar | 24 |
| Carbo Sugar (diluted with 2% KCl) | 26 |
| Commercial Guar + Carbo Sugar (diluted in 2% KCl) | 30 |

As seen in Table 5, even without further optimization, carbo sugar preparations perform similarly to commercial guar preparations.

Figure 12:
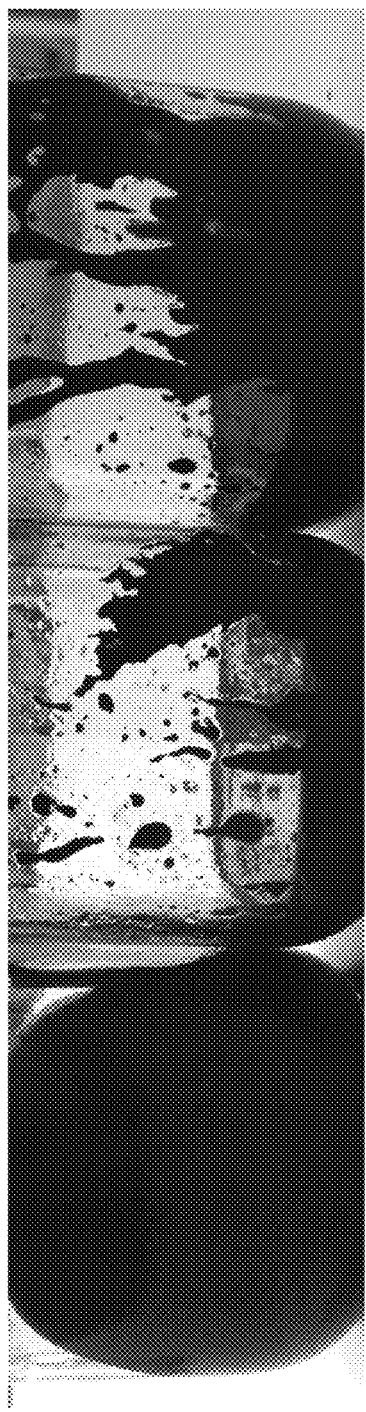
FIG. 12 shows petroleum samples treated with guar. Left jar: Control (petroleum+no guar). Center jar: Petroleum sample+commercial guar. Right jar: Petroleum sample+ carbo sugar.
Figure 13:
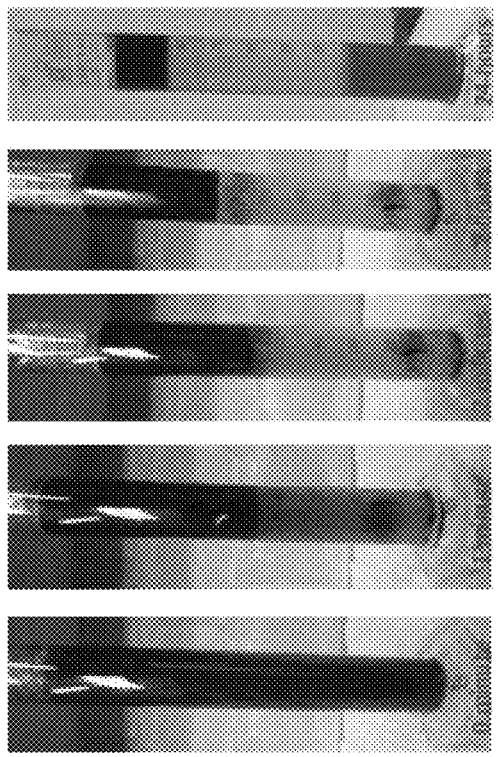
FIG. 13 shows the result of treating an emulsified petroleum solution with the biological devices described herein. From left to right, the sample at the initial time, at 1 minute, at 2 minutes, at 2 hours, and at 24 hours are shown. By 24 hours, the petroleum is completely separated from the water.
Figure 14A:
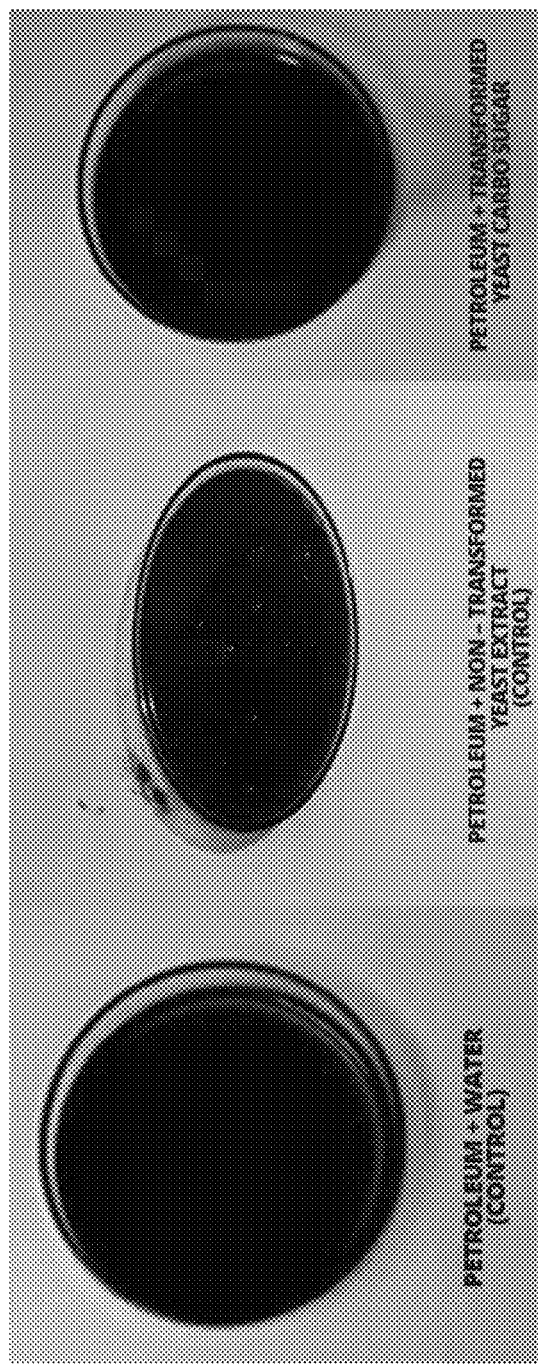
FIGS. 14A-14D show decontamination of glass surfaces coated with petroleum oil. In each of 14A, 14B, 14C, and 14D, the leftmost photo is a control where a petroleum oil coated Petri dish is treated with only water. The center photo is petroleum oil treated with a non-transformed yeast extract. The right most photo is petroleum oil treated with the biological devices described herein.
Figure 14B:
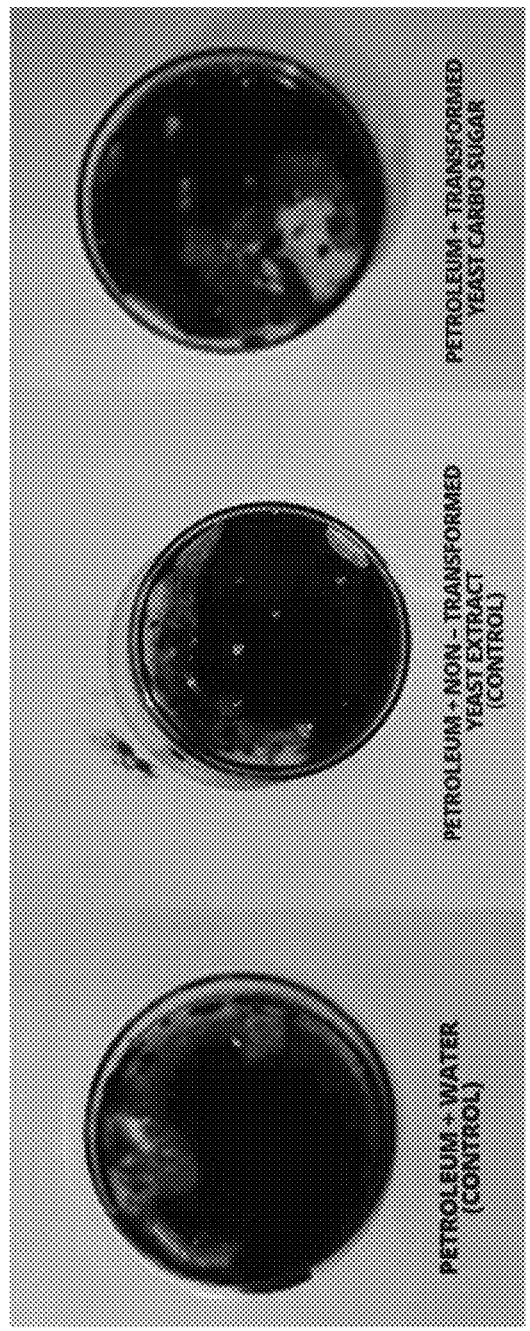
Figure 14C:
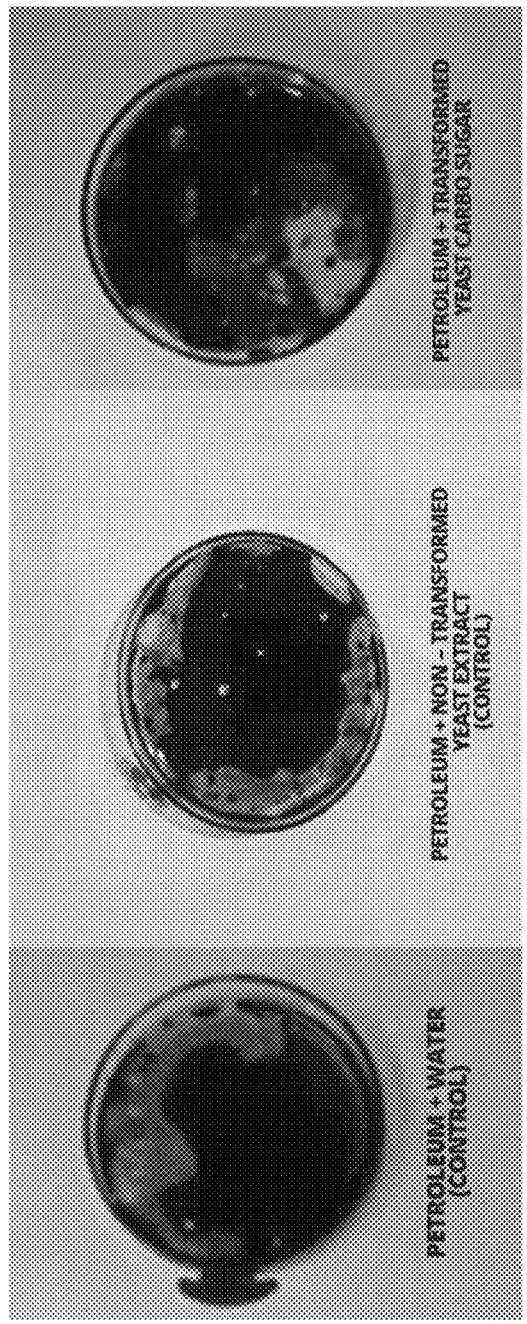
Figure 14D:
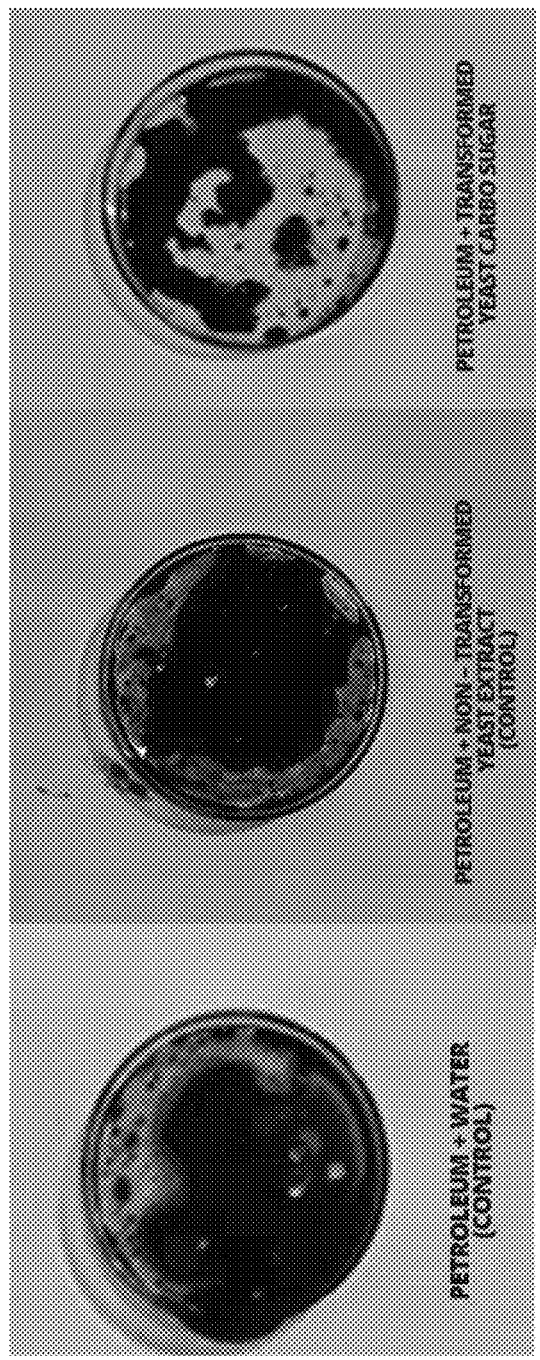

Oil+treatment samples were prepared by mixing 10 mL of petroleum oil and 5 mL of each treatment (a 2:1 proportion). These were shaken at 120 rpm for 30 min and viscosity was measured. Photographs of representative samples can be seen in FIG. 12 (11A control with 12 API petroleum; 11B oil treated with commercial guar; 11C oil treated with carbo sugar). Results obtained after optimization of the treatment protocol are presented in Table 6.

TABLE 6

Reduction of Petroleum Viscosity Using Carbo Sugar Preparations

| Treatment | API Gravity |
|---|---|
| Control: Pure Oil | 14.6 |
| Commercial Guar (diluted with 2% KCl) | 15.4 |
| Carbo Sugar | 31.3 |
| Carbo Sugar (diluted with 2% KCl) | 22.6 |
| Commercial Guar + Carbo Sugar (diluted in 2% KCl) | 23.6 |
| Commercial Guar + Carbo Sugar + Ethoxylated Alcohol | 17.3 |

As can be seen in Table 6, for the optimized treatment protocol, carbo sugar produced herein outperforms commercial guar in side-by-side tests of reduction of petroleum viscosity.

Example 4: Degreasing of Water by Carbo Sugar

The effects of the biological devices described herein on degreasing water contaminated with petroleum oil were tested. Transformed yeast cells were grown on conventional media. Growth was determined using a spectrophotometer at between 30 and 48 hours to measure optical density ($OD_{600}$) with a target of between 0.5 and 1.5. When desired growth was achieved, the yeast culture was treated with a lyticase enzyme (7004 per 1 L of culture), followed by treatment with chitosan (0.01%) in order to break up yeast cell walls and release the carbo sugar compounds. The resulting solution was stirred under sonication and/or vacuum conditions for 3-5 minutes and filtered through a 0.8 µm filter. The filtrate of the carbo sugar with lysed yeast was then centrifuged at 9000 rpm at 4° C. two times, for 10 minutes each time. A pellet was obtained.

One gram of pellet was mixed with 100 mL of sterilized distilled water. The solution obtained from the pellet was used to treat varying types of petroleum solutions (e.g., heavy or light oil, oil with varied API values). These treatments were carried out in glass Petri dishes, beakers, or flasks, with different ratios of petroleum to carbo sugar being employed in order to determine optimum concentrations for various elements of the treatments. It was found that a 1:2 or 1:3 ratio of petroleum to carbo sugar was preferable and that a 0.5% or 1% concentration of carbo sugar. Various controls were also performed including untreated samples and samples treated with non-transformed yeast.

Apparent clearance or disappearance of petroleum oil in the container (beaker, flask, or Petri dish) was used to measure the degreasing effect of the carbo sugar treatment, which was evaluated at different times ranging from 0 minutes to 60 minutes.

FIGS. 13, 14A-14D, and 15A and 15B show the ability of the carbo sugar disclosed herein to degrease surfaces and decontaminate water that has been emulsified with petroleum oil versus non-transformed yeast controls and untreated samples.

In another series of experiments, 5 mL of petroleum (either heavy or light) were mixed with 10 mL of extract produced by the biological devices as described in Example 2. The petroleum was mixed with (A) autoclaved culture extracts from transformed yeasts, (B) non-autoclaved culture extracts from transformed yeasts, and (C) water. Mixtures were shaken for at least 15 sec, then Petri dishes containing the mixture were incubated at room temperature (approximately 24-26° C.). Observations were made at the starting time, at 30 minutes, and at 24 hours.

Figure 21:
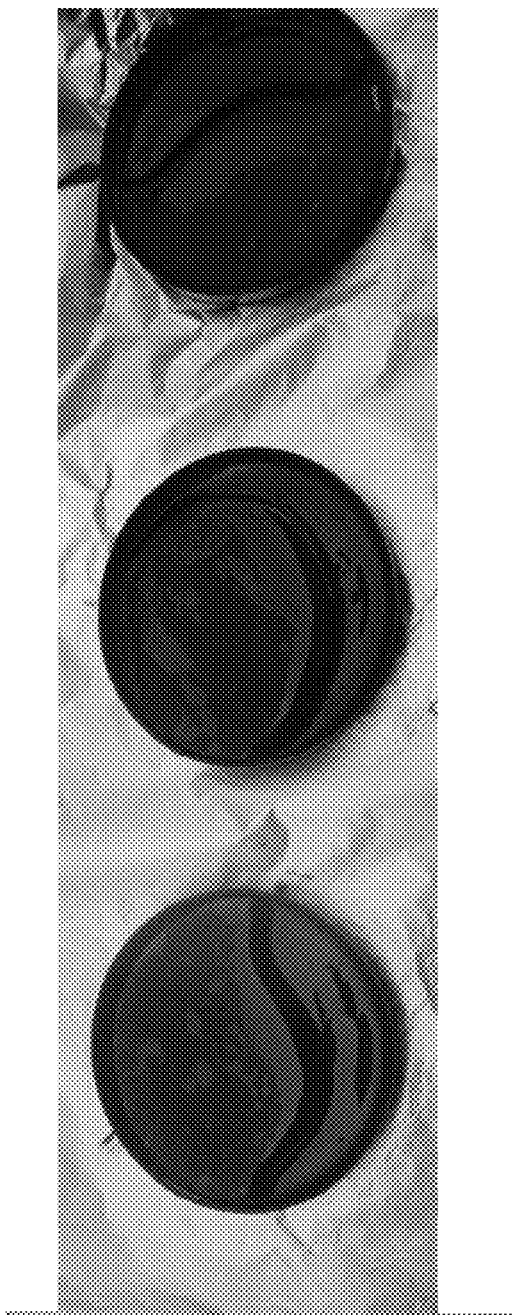
FIG. 21 shows the use of an extract described herein in the degreasing of surfaces contaminated with petroleum at time 0.
Figure 22:
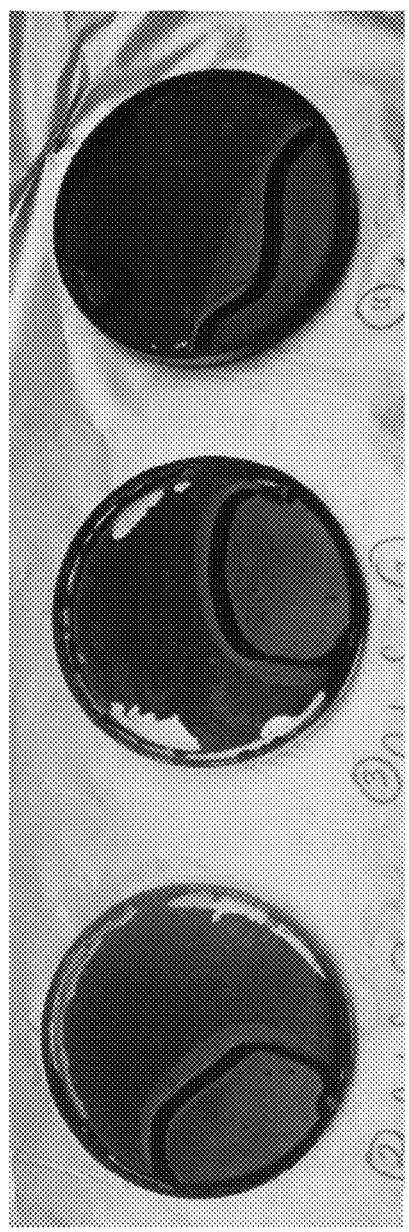
FIG. 22 shows the use of an extract described herein in the degreasing of surfaces contaminated with petroleum after 30 minutes.
Figure 23:
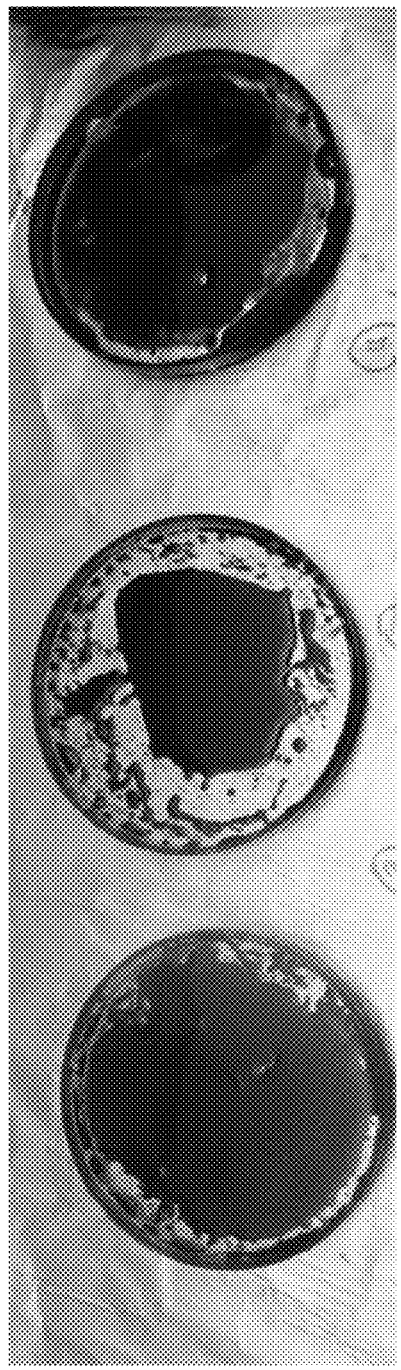
FIG. 23 shows the use of an extract described herein in the degreasing of surfaces contaminated with petroleum after 24 hours.

The results of these degreasing experiments can be seen in FIGS. 21-23. No degreasing occurred immediately upon mixing in samples A-C (FIG. 21). At 30 minutes, slight degreasing was observed in the non-autoclaved culture extract (FIG. 22, sample B) when compared to samples A and C. After 24 hours, the most effective degreasing was observed in sample B, while the autoclaved culture extract (sample A) was less effective at degreasing (FIG. 23).

Example 5: Fracking by Carbo Sugar

Figures 18A, 18B:
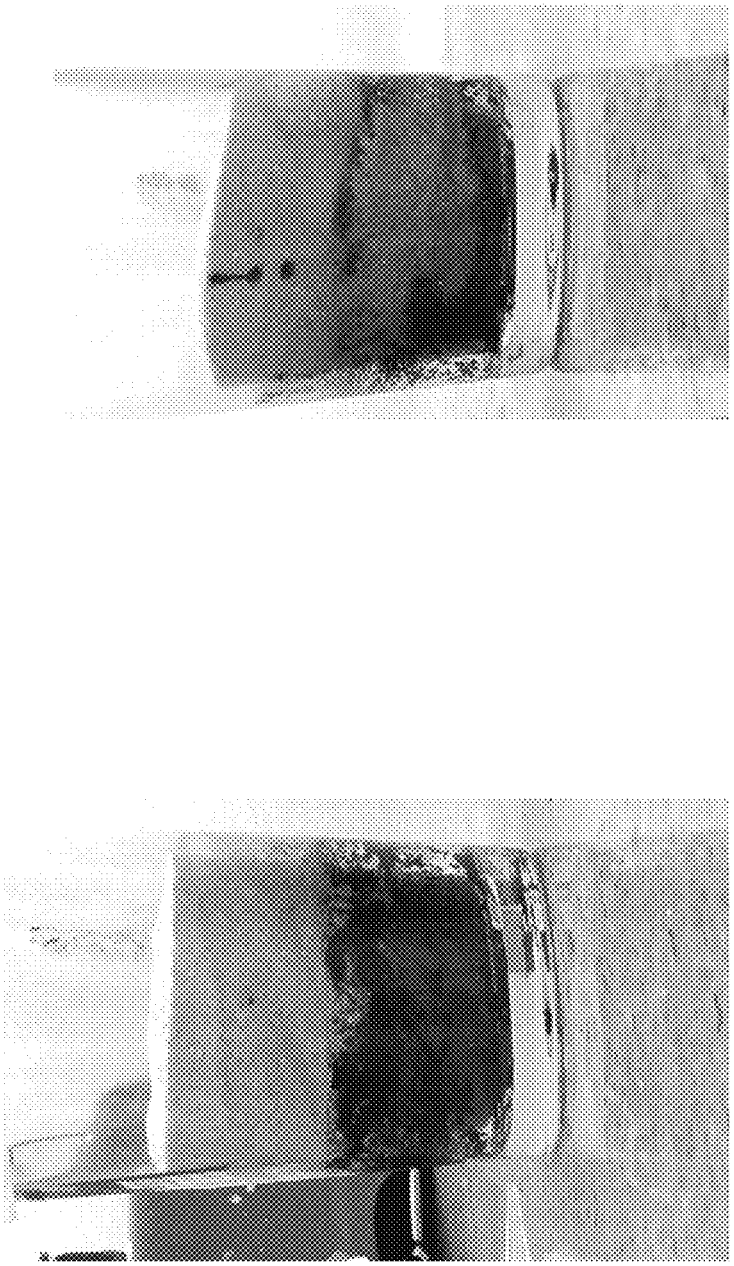
FIGS. 18A and 18B show the ability of the carbo sugar produced herein to disperse petroleum through sand.

A solution of carbo sugar produced in Example 2 was mixed with a petroleum sample. The petroleum sample was then added to sand in a glass container. In a control experiment, a second petroleum sample was prepared by mixing petroleum with water. The control sample was added to a separate glass container with sand. After two minutes, the petroleum sample with the carbo sugar began being absorbed by the sand and after five minutes, this sample had dispersed throughout the sand (FIG. 18B). Conversely, the petroleum sample with just water stayed localized in the sand (FIG. 18A).

In another series of experiments, culture extracts of yeasts transformed with the devices disclosed herein as described in Example 2 were evaluated for their abilities to entrap petroleum in sand as follows. 10 mL of petroleum (either heavy or light) were mixed with 10 mL of various treatments and 1 g of small grain sand in 100 mL glass bottles. The bottles were incubated at 60° C. in a water bath for 15 min and then allowed to sit at room temperature (approximately 25-27° C.) until the end of the experiment. Samples were evaluated for the degree of mixing of petroleum with sand and presence of layers of petroleum above or below the sand layer. Results are provided in FIGS. 24 and 25.

Figure 24:
FIG. 24 shows the entrapment of petroleum in sand at time 0 using an extract described herein.
Figure 25:
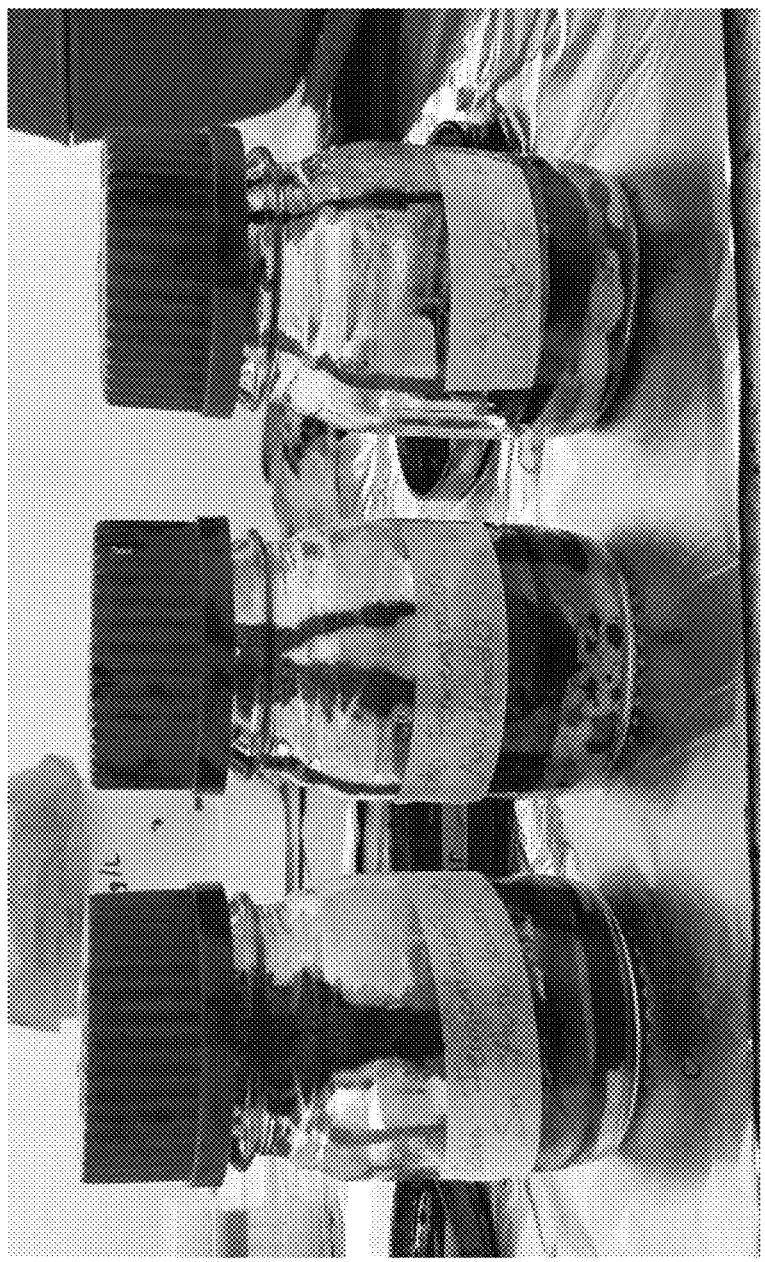
FIG. 25 shows the entrapment of petroleum in sand after 24 hors using an extract described herein.

After the initial mixing, no mixing among petroleum, sand, and any treatment occurred (FIG. 24). After 24 hours, petroleum with water and sand (sample A) showed less presence of petroleum in the sand than samples treated with either autoclaved and sonicated extract (sample B) or non-autoclaved/non-sonicated culture extract (sample C) (FIG. 25). Thus, treatment with culture extracts disclosed herein are better able to draw petroleum out of water and into sand in a model fracking process.

Example 6: Isolation and Production of Powder Form of Carbo Sugar

Figure 16A:
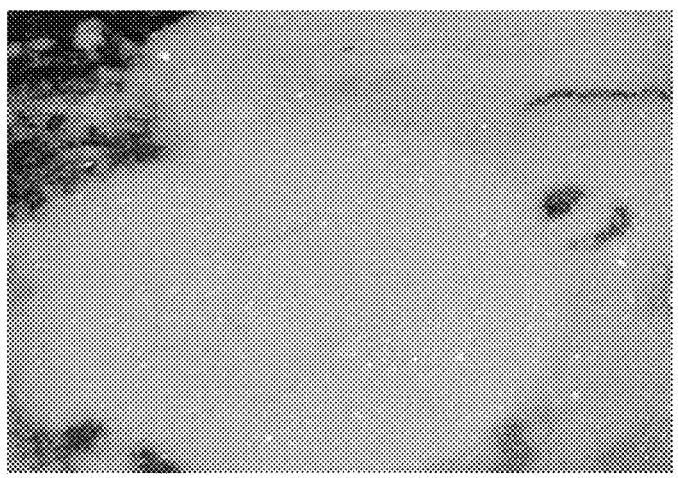
FIGS. 16A and 16B show the carbo sugar in powder and crystalline form.
Figure 16B:
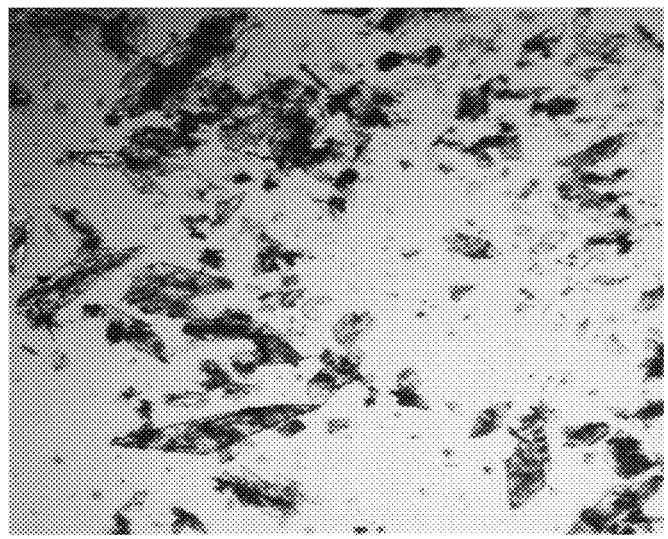

The following procedure was used to produce the carbo sugar in powder form. The carbo sugar device (yeast at $10^9$ cells) was fermented in yeast malt at 30° C. for 72 hours. At 48 hours, lyticase (24 µL/L) was added to the culture. The carbo sugar device was autoclaved for 30 minutes at 121° C. The autoclaved culture medium was filtered through an 8 micron filter. Water was removed by lyophilization to produce the carbo sugar as a crystalline powder (FIG. 16).

Example 7: Preparation of Biofoams

The carbo sugars described herein were used to prepare hard biofoams. A typical biofoam was prepared by admixing a biopolyol solution and an isocyanate.

Figure 17:
FIG. 17 shows that a hard biofoam described herein is resistant to water.

A first hard biofoam was prepared using the following procedure. A solution of carbo sugar (0.5 g of carbo sugar produced in Example 6 was mixed with 59 mL of water) was produced. To the carbo sugar solution was added 1 mL of polysorbate 80 followed by the addition of castor oil (40 mL). The solution was stirred for 5 minutes. Next 0.5 g of bentonite was added and the solution was stirred for 5 minutes to produce a biopolyol solution. To the biopolyol solution was added 25 mL of polymeric MDI 253 (4,4'-methylene diphenyl diisocyanate) at a v/v ratio of 4:1 biopolyol solution to diisocyanate and mixed for 10 minutes. The biofoam formed approximately 10 minutes after mixing biopolyol solution and isocyanate and exhibited a total drying time of approximately 24 hours. The biofoam had a weight of 63.83 g, dimensions of 7 cm×7 cm×7 cm, and a density of 0.1860 g/cm$^3$. The biofoam is resistant to water even after several days (FIG. 17).

In a comparative experiment, a biopolyol solution was prepared without the carbo sugar (i.e., just 59 mL of water). The use of this solution did not result in the formation of a biofoam.

Throughout this application, various publications are referenced. The disclosures of these publications in their entireties are hereby incorporated by reference into this application in order to more fully describe the compounds, compositions and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A biological device comprising host cells transformed with a vector, wherein the vector comprises a DNA construct comprising the following genetic components:
   a. a gene having SEQ ID NO: 1 that encodes cellulose synthase;
   b. a gene having SEQ ID NO: 4 that encodes galactomannan galactosyltransferase; and
   c. a gene having SEQ ID NO: 9 that encodes lipase.

2. The biological device of claim 1, wherein the construct further comprises at least one promoter, at least one terminator or stop codon, a LAC operon, at least one ribosomal binding site, or any combination thereof.

3. The biological device of claim 1, wherein the construct comprises from 5' to 3' the following genetic components in the following order: (a) the gene that encodes lipase, (b) the gene that encodes cellulose synthase, and (c) the gene that encodes galactomannan galactosyltransferase.

4. The biological device of claim 2, wherein the promoter is a Gal1 promoter, the terminator is a CYC1 terminator, and the construct comprises from 5' to 3' the following genetic components in the following order: (a) the Gal1 promoter; (b) the gene that encodes lipase, (c) the gene that encodes cellulose synthase; (d) the gene that encodes galactomannan galactosyltransferase; and (e) the CYC1 terminator or stop codon.

5. The biological device of claim 2, wherein the promoter is a Gal1 promoter, the terminator is a CYC1 terminator, and the construct comprises from 5' to 3' the following genetic components in the following order: (a) the gene that encodes lipase, (b) the Gal1 promoter; (c) the gene that encodes cellulose synthase; (d) the CYC1 terminator; (e) the Gal1 promoter; (f) the gene that encodes galactomannan galactosyltransferase; and (g) the CYC1 terminator.

6. The biological device of claim 2, wherein the promoter is a T7 promoter and the construct comprises the following genetic components: (a) the gene that encodes lipase wherein the gene has SEQ ID NO: 9; (b) the T7 promoter, (c) the LAC operon, (d) the ribosomal binding site, (e) the gene that encodes cellulose synthase wherein the gene has SEQ ID NO: 1, (f) the ribosomal binding site, and (g) the gene that encodes galactomannan galactosyltransferase wherein the gene has SEQ ID NO: 4.

7. The biological device of claim 2, wherein the promoter is a Gal1 promoter and the construct comprises from 5' to 3' the following genetic components in the following order: (a) the Gal1 promoter; (b) the gene that encodes lipase wherein the gene has SEQ ID NO: 9; (c) the gene that encodes cellulose synthase wherein the gene has SEQ ID NO: 1; and (d) the gene that encodes galactomannan galactosyltransferase wherein the gene has SEQ ID NO: 4.

8. The biological device of claim 1, wherein the vector is a plasmid.

9. The biological device of claim 8, wherein the vector is pWLneo, pSV2cat, pOG44, pXT1, pSG, pSVK3, pBSK, pBSKII, pYES, pYES2, pUC, pUC19, or pETDuet-1.

10. The biological device of claim 8, wherein the vector is pYES2.

11. The biological device of claim 8, wherein the vector is pETDuet-1.

12. The biological device of claim 1, wherein the host cells comprise fungi or bacteria.

13. The biological device of claim 12, wherein the bacteria comprises *E. coli*.

14. The biological device of claim 12, wherein the fungus comprises *S. cerevisiae*.

15. The biological device of claim 1, wherein the host cells comprise yeast.

16. A method for producing a carbo sugar comprising growing the biological device of claim 1 for a sufficient time to produce the carbo sugar.

17. The method of claim 16, wherein after growing the biological device to produce a carbo sugar composition, (1) lysing the host cells in the carbo sugar composition to produce a lysed composition, and (2) separating the carbo sugar from the lysed composition.

* * * * *